United States Patent
Beeson et al.

(10) Patent No.: US 10,370,328 B2
(45) Date of Patent: *Aug. 6, 2019

(54) OXINDOLE COMPOUNDS AND PHARMACEUTICAL COMPOSITIONS THEREOF

(71) Applicants: MUSC FOUNDATION FOR RESEARCH DEVELOPMENT, Charleston, SC (US); U.S. DEPARTMENT OF VETERANS AFFAIRS, NW Washington, DC (US)

(72) Inventors: Craig C. Beeson, Charleston, SC (US); Christopher C. Lindsey, Wadmalaw Island, SC (US); Baerbel Rohrer, Charleston, SC (US); Yuri Karl Peterson, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/565,820

(22) PCT Filed: Apr. 28, 2016

(86) PCT No.: PCT/US2016/029726
§ 371 (c)(1),
(2) Date: Oct. 11, 2017

(87) PCT Pub. No.: WO2016/176420
PCT Pub. Date: Nov. 3, 2016

(65) Prior Publication Data
US 2018/0134659 A1    May 17, 2018

Related U.S. Application Data

(60) Provisional application No. 62/155,019, filed on Apr. 30, 2015.

(51) Int. Cl.
| | | |
|---|---|---|
| C07D 209/38 | (2006.01) |
| C07D 401/06 | (2006.01) |
| C07D 403/06 | (2006.01) |
| C07D 209/36 | (2006.01) |
| C07D 403/12 | (2006.01) |
| C07D 401/14 | (2006.01) |
| C07D 401/12 | (2006.01) |
| C07D 403/14 | (2006.01) |
| C07D 405/06 | (2006.01) |
| C07D 413/06 | (2006.01) |
| C07D 498/04 | (2006.01) |
| A61P 27/02 | (2006.01) |
| C07D 209/34 | (2006.01) |
| C07D 405/12 | (2006.01) |
| C07F 9/572 | (2006.01) |

(52) U.S. Cl.
CPC ............ *C07D 209/38* (2013.01); *A61P 27/02* (2018.01); *C07D 209/34* (2013.01); *C07D 209/36* (2013.01); *C07D 401/06* (2013.01); *C07D 401/12* (2013.01); *C07D 401/14* (2013.01); *C07D 403/06* (2013.01); *C07D 403/12* (2013.01); *C07D 403/14* (2013.01); *C07D 405/06* (2013.01); *C07D 405/12* (2013.01); *C07D 413/06* (2013.01); *C07D 498/04* (2013.01); *C07F 9/5728* (2013.01)

(58) Field of Classification Search
CPC ..................................... C07D 209/38
USPC ....................................... 514/323
See application file for complete search history.

(56) References Cited

U.S. PATENT DOCUMENTS

| | | | | |
|---|---|---|---|---|
| 7,799,782 B2* | 9/2010 | Munson | ............... | C07D 231/56 514/234.5 |
| 9,079,853 B2* | 7/2015 | Beeson | ............... | C07D 401/04 |
| 9,920,029 B2* | 3/2018 | Beeson | ............... | C07D 401/04 |
| 2007/0167488 A1* | 7/2007 | Bouerat Duvold | .. | A61K 31/404 514/323 |
| 2013/0137728 A1 | 5/2013 | Beeson et al. | | |
| 2014/0275075 A1 | 9/2014 | Beeson et al. | | |
| 2014/0275178 A1 | 9/2014 | Beeson et al. | | |

FOREIGN PATENT DOCUMENTS

| | | |
|---|---|---|
| CN | 1365972 A | 8/2002 |
| WO | 2006032164 A1 | 3/2006 |
| WO | 2006105795 A1 | 10/2006 |
| WO | WO2011119869 * | 9/2011 |
| WO | 2014074976 A1 | 5/2014 |

OTHER PUBLICATIONS

The International Search Report and Written Opinion, dated Jul. 7, 2016, in the corresponding PCT Appl. No. PCT/US2016/029726.
(Continued)

*Primary Examiner* — Rei Tsang Shiao

(57) ABSTRACT

Provided herein are compounds of the formula (I) as well as pharmaceutically acceptable salts thereof, wherein the substituents are as those disclosed in the specification. These compounds, and the pharmaceutical compositions containing them, are useful for the treatment of degenerative diseases and disorders.

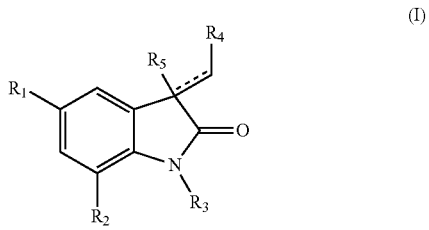

(I)

2 Claims, No Drawings

(56) References Cited

OTHER PUBLICATIONS

The English translation of the Japanese Office Action, dated Oct. 1, 2018, in the related Japanese Appl. No. 2017-557113.
Mulla, Shafeek A. R. et al., "A novel and efficient synthesis of azaarene-substituted 3-hydroxy-2-oxindoles via sp3 C—H functionalization of 2-methyl azaarenes and (2-azaaryl)methanes over a heterogeneous, reusable silica-supported dodecatungstophosphoric acid catalyst," RSC Advances, 2013, 3(43), 20281-20286.
Niu, Rui et al., "Yb(OTf)3-catalyzed addition of 2-methyl azaarenes to isatins via C—H functionalization," Cuihua Xuebao, 2012, 33(10), 1636-1641.
Raghu, M. et al., "Polyethylene glycol (PEG-400): a mild and efficient reaction medium for one-pot synthesis of 3-hydroxy-3-(pyridin-2-ylmethyl)indolin-2-ones," Tetrahedron Letters, 2013, 54(27), 3503-3506.
Ghandi, Mehdi et al., "Solvent-dependent Baylis-Hillman reactions for the synthesis of 3-benzyl-3-hydroxyoxindoles and benzo-δ-sultams," Tetrahedron, 2014, 70(15), 2563-2569.
Yang, Xu-Heng et al., Room-Temperature Palladium-Catalyzed Intramolecular Oxidative Aminocarbonylation of Vinylic C(sp2)—H Bonds with Amines and CO,European Journal of Organic Chemistry, 2014, 2014(3), 616-623.
Su, Shikuan et al, Tandem Diels-Alder/Coupling Reaction Involving Two Arynes: Highly Stereoselective Synthesis of Dihydronaphtho-Fused Oxindole, Asian Journal of Organic Chemistry, 2014, 3(3), 269-272.

\* cited by examiner

OXINDOLE COMPOUNDS AND PHARMACEUTICAL COMPOSITIONS THEREOF

CROSS-REFERENCE TO RELATED APPLICATIONS

This application is a National Stage Application of PCT/US2016/029726 filed on Apr. 28, 2016, which claims priority from U.S. Provisional Patent Application No. 62/155,019 filed on Apr. 30, 2015. Each of prior mentioned applications is hereby expressly incorporated by reference herein in its entirety.

FIELD OF THE INVENTION

The invention is directed to compounds of formula (I):

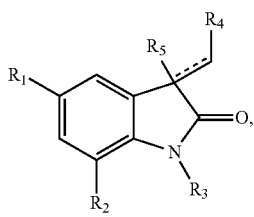

to pharmaceutical compositions comprising the compounds and to methods of using the compounds. The compounds and compositions disclosed herein protect against calcium- and oxidative-stress mediated damage to mitochondrial functions and are useful for the treatment of degenerative diseases and disorders.

All documents cited or relied upon below are expressly incorporated herein by reference.

BACKGROUND OF THE INVENTION

Mitochondria are cellular organelles present in most eukaryotic cells. One of their primary functions is oxidative phosphorylation, a process through which energy derived from metabolism of fuels like glucose or fatty acids is converted to ATP, which is then used to drive various energy-requiring biosynthetic reactions and other metabolic activities. Mitochondria have their own genomes, separate from nuclear DNA, comprising rings of DNA with about 16,000 base pairs in human cells. Each mitochondrion may have multiple copies of its genome, and individual cells may have hundreds of mitochondria. In addition to supplying cellular energy, mitochondria are involved in a range of other processes, such as signaling, cellular differentiation, cell death, as well as the control of the cell cycle and cell growth (McBride et al., Curr. Biol., 2006, 16 (14): R551).

As mitochondria produce ATP, they simultaneously yield reactive oxygen species (ROS), which are harmful free radicals that circulate throughout the cell, the mitochondria, and the body, causing more damage. The circulation of ROS leads to the activation of reactive nitrogen compounds, which in turn induce, or activate, genes in the DNA that are associated with many degenerative diseases. The DNA for each mitochondrion (mtDNA) remains unprotected within the membrane of the mitochondrion itself. In comparison to the DNA in the nucleus of the cell (nDNA), mtDNA is easily damaged by free radicals and the ROS that it produces. Freely floating mtDNA lacks protective measures associated with nDNA, and therefore suffers from multiple mutations. It has been estimated that the lack of protective measures results in mutations to mtDNA occurring 10 to 20 times more frequently than mutations to nDNA.

Mitochondrial damage and/or dysfunction contribute to various disease states. Some diseases are due to mutations or deletions in the mitochondrial genome. Mitochondria divide and proliferate with a faster turnover rate than their host cells, and their replication is under control of the nuclear genome. If a threshold proportion of mitochondria in a cell is defective, and if a threshold proportion of such cells within a tissue have defective mitochondria, symptoms of tissue or organ dysfunction can result. Practically any tissue can be affected, and a large variety of symptoms can be present, depending on the extent to which different tissues are involved.

A fertilized ovum might contain both normal and genetically defective mitochondria. The segregation of defective mitochondria into different tissues during division of this ovum is a stochastic process, as will be the ratio of defective to normal mitochondria within a given tissue or cell (although there can be positive or negative selection for defective mitochondrial genomes during mitochondrial turnover within cells). Thus, a variety of different pathologic phenotypes can emerge out of a particular point mutation in mitochondrial DNA. Conversely, similar phenotypes can emerge from mutations or deletions affecting different genes within mitochondrial DNA. Clinical symptoms in congenital mitochondrial diseases often manifest in postmitotic tissues with high energy demands like brain, muscle, optic nerve, and myocardium, but other tissues including endocrine glands, liver, gastrointestinal tract, kidney, and hematopoietic tissue are also involved, again depending in part on the segregation of mitochondria during development and on the dynamics of mitochondrial turnover over time.

In addition to congenital disorders involving inherited defective mitochondria, acquired mitochondrial damage and/or dysfunction contribute to diseases, particularly neurodegenerative disorders associated with aging like Parkinson's, Alzheimer's, Huntington's Diseases. The incidence of somatic mutations in mitochondrial DNA rises exponentially with age; and diminished respiratory chain activity is found universally in aging people. Mitochondrial dysfunction is also implicated in excitotoxic neuronal injury, such as that associated with seizures or ischemia.

Other pathologies with etiology involving mitochondrial damage and/or dysfunction include schizophrenia, bipolar disorder, dementia, epilepsy, stroke, cardiovascular disease, retinal degenerative disease (e.g., age-related macular degeneration, Stargardt's disease, glaucoma, retinitis pigmentosa, and optic nerve degeneration), and diabetes mellitus. A common thread thought to link these seemingly-unrelated conditions is cellular damage causing oxidative stress. Oxidative stress is caused by an imbalance between the production of reactive oxygen and a biological system's ability to readily detoxify the reactive intermediates or easily repair the resulting damage. All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids, and DNA.

Mitochondrial damage and/or dysfunction particularly contribute to degenerative diseases. Degenerative diseases are diseases in which the function or structure of the affected tissues or organs will progressively deteriorate over time. Some examples of degenerative diseases are retinal degenerative disease, e.g., age-related macular degeneration, Stargardt's disease, glaucoma, retinitis pigmentosa, and optic nerve degeneration; Amyotrophic Lateral Sclerosis (ALS), e.g., Lou Gehrig's Disease; Alzheimer's disease; Parkinson's Disease; Multiple system atrophy; Niemann Pick disease; Atherosclerosis; Progressive supranuclear palsy; Cancer; Tay-Sachs Disease; Diabetes; Heart Disease; Keratoconus; Inflammatory Bowel Disease (IBD); Prostatitis; Osteoarthritis; Osteoporosis; Rheumatoid Arthritis; and Huntington's Disease.

Treatment of degenerative diseases involving mitochondrial damage and/or dysfunction has heretofore involved administration of vitamins and cofactors used by particular elements of the mitochondrial respiratory chain. Coenzyme Q (ubiquinone), nicotinamide, riboflavin, carnitine, biotin, and lipoic acid are used in patients with occasional benefit, especially in disorders directly stemming from primary deficiencies of one of these cofactors. However, while useful in isolated cases, no such metabolic cofactors or vitamins have been shown to have general utility in clinical practice in treating degenerative diseases involving mitochondrial damage and/or dysfunction.

Therefore, a need exists for new drug therapies for the treatment of subjects suffering from or susceptible to the above disorders or conditions associated with mitochondrial damage and/or dysfunction. In particular, a need exists for new drugs having one or more improved properties (such as safety profile, efficacy or physical properties) relative to those currently available.

SUMMARY OF THE INVENTION

The present invention is directed to a compound of formula (I):

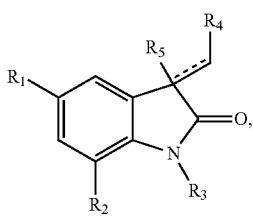

wherein:
$R_1$ and $R_2$ are, independently of each other, hydrogen, lower alkyl or halogen;
$R_3$ is lower alkyl, branched or unbranched, optionally substituted with —$CF_3$ or piperidine;
$R_4$ is: (i) phenyl, optionally mono-, bi- or tri-substituted independently with alkoxy, hydroxy, —OC(O)$CH_3$, —OC(O)$CH_2$O$CH_3$, —OC(O)-lower alkyl, —OC(O)NHCH$_2$CH$_2$OCH$_2$CH$_2$OH, —OSO$_2$N(CH$_3$)$_2$ or —OC(O)N(CH$_3$)$_2$;
(ii) methyl-1H-indazolyl,
(iii) benzo[d][1,3]dioxolyl,
(iv) benzo[d]imidazolyl,
(v) benzoyl-1H-indolyl,
(vi) benzo[d]oxazolyl,
(vii) oxazolo[4,5-b]pyridinyl or
(viii) a 6-membered heteroaryl group having one or more ring carbons replaced by N;

$R_5$ is hydrogen, hydroxyl, —$CH_2$-pyridazinyl, —$OR_6$, —$NHR_6$ or absent;
$R_6$ is —C(O)-pyridinyl, —P(O)(OCH$_2$CH$_3$)$_2$, —C(O)CH$_2$OCH$_3$, —C(O)N(CH$_3$)$_2$, —C(O)—O-1,3-dioxolan-4-yl)methyl, —SO$_2$-phenylmethyl or —C(O)-phenyl; and
the symbol $\doteq$ indicates a single or double bond,
or a pharmaceutically acceptable salt thereof.

The present invention is also directed to pharmaceutical compositions containing the above compounds and to methods of treating degenerative diseases and disorders.

DETAILED DESCRIPTION OF THE INVENTION

It is to be understood that the terminology employed herein is for the purpose of describing particular embodiments, and is not intended to be limiting. Further, although any methods, devices and materials similar or equivalent to those described herein can be used in the practice or testing of the invention, certain methods, devices and materials are now described.

As used herein, the term "alkyl", alone or in combination with other groups, refers to a branched or straight-chain monovalent saturated aliphatic hydrocarbon radical of one to twenty carbon atoms, in one embodiment one to sixteen carbon atoms, in another embodiment one to ten carbon atoms.

As used herein, the term "alkenyl", alone or in combination with other groups, refers to a straight-chain or branched hydrocarbon residue having an olefinic bond.

The term "cycloalkyl" refers to a monovalent mono- or polycarbocyclic radical of three to ten, in one embodiment three to six, carbon atoms. This term is further exemplified by radicals such as cyclopropyl, cyclobutyl, cyclopentyl, cyclohexyl, cycloheptyl, norbornyl, adamantyl, indanyl and the like. In one embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate.

The term "lower alkyl", alone or in combination with other groups, refers to a branched or straight-chain alkyl radical of one to nine carbon atoms, in another embodiment one to six carbon atoms, in a further embodiment one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, in another embodiment, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, aryl sulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkyl sulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups.

As used herein, the term "halogen" means a fluorine, chlorine, bromine or iodine radical, in another embodiment a fluorine, chlorine or bromine radical, and in a further embodiment a bromine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Representative embodiments include fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In one embodiment of the invention, provided is a compound of formula (I):

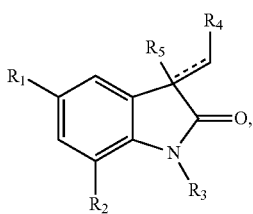 (I)

wherein:

R$_1$ and R$_2$ are, independently of each other, hydrogen, lower alkyl or halogen;

R$_3$ is lower alkyl, branched or unbranched, optionally substituted with —CF$_3$ or piperidine;

R$_4$ is: (i) phenyl, optionally mono-, bi- or tri-substituted independently with alkoxy, hydroxy, —OC(O)CH$_3$, —OC(O)CH$_2$OCH$_3$, —OC(O)-lower alkyl, —OC(O)NHCH$_2$CH$_2$OCH$_2$CH$_2$OH, —OSO$_2$N(CH$_3$)$_2$ or —OC(O)N(CH$_3$)$_2$;
  (ii) methyl-1H-indazolyl,
  (iii) benzo[d][1,3]dioxolyl,
  (iv) benzo[d]imidazolyl,
  (v) benzoyl-1H-indolyl,
  (vi) benzo[d]oxazolyl,
  (vii) oxazolo[4,5-b]pyridinyl or
  (viii) a 6-membered heteroaryl group having one or more ring carbons replaced by N;

R$_5$ is hydrogen, hydroxyl, —CH$_2$-pyridazinyl, —OR$_6$, —NHR$_6$ or absent;

R$_6$ is —C(O)-pyridinyl, —P(O)(OCH$_2$CH$_3$)$_2$, —C(O)CH$_2$OCH$_3$, —C(O)N(CH$_3$)$_2$, —C(O)—O-1,3-dioxolan-4-yl)methyl, —SO$_2$-phenylmethyl or —C(O)-phenyl; and the symbol ═ indicates a single or double bond, or a pharmaceutically acceptable salt thereof.

In another embodiment of the invention, provided is a compound of formula I wherein R$_1$ is hydrogen.

In another embodiment of the invention, provided is a compound of formula I wherein R$_1$ is lower alkyl or halogen.

In another embodiment of the invention, provided is a compound of formula I wherein R$_1$ is methyl or chlorine.

In another embodiment of the invention, provided is a compound of formula I wherein R$_2$ is hydrogen.

In another embodiment of the invention, provided is a compound of formula I wherein R$_3$ is unsubstituted lower alkyl.

In another embodiment of the invention, provided is a compound of formula I wherein R$_3$ is methyl, ethyl, pentyl, butyl, isobutyl, isopentyl or methylpentyl.

In another embodiment of the invention, provided is a compound of formula I wherein R$_3$ is trifluoroethyl.

In another embodiment of the invention, provided is a compound of formula I wherein R$_4$ is unsubstituted phenyl.

In another embodiment of the invention, provided is a compound of formula I wherein R$_4$ is phenyl mono-, bi or trisubstituted independently with alkoxy or hydroxy.

In another embodiment of the invention, provided is a compound of formula I wherein R$_4$ is phenyl bisubstituted independently with alkoxy, hydroxy, —OC(O)CH$_3$, —OC(O)CH$_2$OCH$_3$, —OC(O)-lower alkyl, —OC(O)NHCH$_2$CH$_2$OCH$_2$CH$_2$OH, —OSO$_2$N(CH$_3$)$_2$ or —OC(O)N(CH$_3$)$_2$.

In another embodiment of the invention, provided is a compound of formula I wherein R$_4$ is methyl-1H-indazolyl, benzo[d][1,3]dioxolyl, benzo[d]imidazolyl, benzoyl-1H-indolyl, benzo[d]oxazolyl or oxazolo[4,5-b]pyridinyl.

In another embodiment of the invention, provided is a compound of formula I wherein R$_4$ is a 6-membered heteroaryl group having one or more ring carbons replaced by N.

In another embodiment of the invention, provided is a compound of formula I wherein R$_4$ is pyrimidinyl, pyrazinyl, pyridazinyl or pyridinyl.

In another embodiment of the invention, provided is a compound of formula I wherein R$_5$ is hydrogen or hydroxy.

In another embodiment of the invention, provided is a compound of formula I wherein R$_5$ is —OR$_6$ or —NHR$_6$.

In another embodiment of the invention, provided is a compound of formula I wherein R$_6$ is —C(O)-pyridinyl or —C(O)-phenyl.

In another embodiment of the invention, provided is a compound of formula I wherein R$_6$ is —C(O)CH$_2$OCH$_3$, —C(O)N(CH$_3$)$_2$ or —C(O)—O-1,3-dioxolan-4-yl)methyl.

In another embodiment of the invention, provided is a compound of formula I wherein R$_6$ is —P(o)(OCH$_2$CH$_3$)$_2$.

In another embodiment of the invention, provided is a compound of formula I wherein the compound is:

3-hydroxy-5-methyl-1-(2,2,2-trifluoroethyl)-3-(3,4,5-trimethoxybenzyl)indolin-2-one;

2-((3-hydroxy-5-methyl-1-(4-methylpentyl)-2-oxoindolin-3-yl)methyl)-5-methoxyphenyl isonicotinate;

2-((3-hydroxy-5-methyl-1-(4-methylpentyl)-2-oxoindolin-3-yl)methyl)-5-methoxyphenyl acetate;

2-((3-hydroxy-5-methyl-1-(4-methylpentyl)-2-oxoindolin-3-yl)methyl)-5-methoxyphenyl 2-methoxyacetate;

5-chloro-1-ethyl-3-(2-hydroxy-3-methoxybenzyl)-2-oxoindolin-3-yl isonicotinate;

5-chloro-1-ethyl-3-(2-hydroxy-3-methoxybenzyl)-2-oxoindolin-3-yl picolinate;

5-chloro-1-ethyl-3-(2-hydroxy-3-methoxybenzyl)-2-oxoindolin-3-yl diethyl phosphate;

2-((5-chloro-1-ethyl-3-hydroxy-2-oxoindolin-3-yl)methyl)-6-methoxyphenyl 2-methoxyacetate;

2-((5-chloro-1-ethyl-3-hydroxy-2-oxoindolin-3-yl)methyl)-6-methoxyphenyl butyrate;

5-chloro-1-ethyl-3-(2-hydroxy-3-methoxybenzyl)-2-oxoindolin-3-yl dimethylcarbamate;

(1,3-dioxolan-4-yl)methyl (5-chloro-1-ethyl-3-(2-hydroxy-3-methoxybenzyl)-2-oxoindolin-3-yl) carbonate;

5-chloro-1-ethyl-3-(2-(((2-(2-hydroxyethoxy)ethyl)carbamoyl)oxy)-3-methoxybenzyl)-2-oxoindolin-3-yl benzoate;

2-((5-chloro-1-ethyl-2-oxoindolin-3-yl)methyl)-6-methoxyphenyl dimethylcarbamate;

3-hydroxy-1,5-dimethyl-3-((1-methyl-1H-indazol-4-yl)methyl)indolin-2-one;

1-butyl-3-((1-methyl-1H-indazol-4-yl)methyl)-2-oxoindolin-3-yl benzoate;

3-(benzo[d][1,3]dioxol-4-ylmethyl)-5-chloro-2-oxo-1-propylindolin-3-yl benzoate;

3-(benzo[d][1,3]dioxol-4-ylmethyl)-1-ethyl-3-hydroxy-5-methylindolin-2-one;

3-(benzo[d][1,3]dioxol-4-ylmethyl)-1-butyl-3-hydroxyindolin-2-one;

3-(benzo[d][1,3]dioxol-4-ylmethyl)-3-hydroxy-1-isobutylindolin-2-one;

3-(benzo[d][1,3]dioxol-4-ylmethyl)-1-isopentyl-2-oxoindolin-3-yl benzoate;

3-(benzo[d][1,3]dioxol-4-ylmethyl)-1-isobutyl-5-methyl-2-oxoindolin-3-yl benzoate;

3-(benzo[d][1,3]dioxol-4-ylmethyl)-1-isopentyl-5-methyl-2-oxoindolin-3-yl benzoate;

3-((1H-benzo[d]imidazol-4-yl)methyl)-5-chloro-1-ethyl-3-hydroxyindolin-2-one,
1-ethyl-3-(2-hydroxy-3,4-dimethoxybenzyl)-5-methyl-2-oxoindolin-3-yl dimethylcarbamate;
3-((1-benzoyl-1H-indol-3-yl)methyl)-2-oxo-1-propylindolin-3-yl dimethylcarbamate;
3-((1H-benzo[d]imidazol-4-yl)methyl)-5-chloro-1-methyl-2-oxoindolin-3-yl dimethylcarbamate;
5-chloro-1-ethyl-3-(pyrimidin-4-ylmethyl)indolin-2-one;
5-methyl-1-ethyl-3-(pyrimidin-4-ylmethylene)indolin-2-one;
5-chloro-1-ethyl-3-hydroxy-3-(pyrazin-2-ylmethyl)indolin-2-one;
1-ethyl-5-methyl-3-(pyrazin-2-ylmethylene)indolin-2-one;
1-propyl-3-(pyridazin-3-ylmethylene)indolin-2-one;
1-propyl-3-(pyridazin-3-ylmethyl)indolin-2-one;
1,5-dimethyl-3-(pyridazin-3-ylmethyl)indolin-2-one;
N-(5-chloro-2-oxo-1-propyl-3-(pyridazin-3-ylmethyl)indolin-3-yl)nicotinamide;
1-methyl-3-(pyridazin-3-ylmethylene)indolin-2-one;
3-((1H-benzo[d]imidazol-2-yl)methylene)-5-chloro-1-ethylindolin-2-one;
5-chloro-3-hydroxy-1-propyl-3-(pyrazin-2-ylmethyl)indolin-2-one;
5-chloro-3-hydroxy-1-methyl-3-(pyridin-4-ylmethyl)indolin-2-one;
5-chloro-3-hydroxy-1-propyl-3-(pyridazin-4-ylmethyl)indolin-2-one;
3-hydroxy-1-methyl-3-(pyridin-4-ylmethyl)indolin-2-one;
(E)-3-((1H-benzo[d]imidazol-2-yl)methylene)-5-chloro-1-methylindolin-2-one;
N-(3-((1H-benzo[d]imidazol-2-yl)methyl)-1-methyl-2-oxoindolin-3-yl)nicotinamide;
1-ethyl-3-hydroxy-3-(pyridazin-3-ylmethyl)indolin-2-one;
1-ethyl-5-methyl-3,3-bis(pyridazin-4-ylmethyl)indolin-2-one;
1-propyl-3,3-bis(pyridazin-4-ylmethyl)indolin-2-one;
1-ethyl-3-hydroxy-5-methyl-3-(pyridazin-3-ylmethyl)indolin-2-one;
N-(3-((1H-benzo[d]imidazol-2-yl)methyl)-5-chloro-1-ethyl-2-oxoindolin-3-yl)isonicotinamide;
3-(benzo[d]oxazol-2-ylmethylene)-5-chloro-1-methylindolin-2-one;
N-(3-((1H-benzo[d]imidazol-2-yl)methyl)-5-chloro-2-oxo-1-propylindolin-3-yl)benzamide;
1-methyl-3-(oxazolo[4,5-b]pyridin-2-ylmethylene)indolin-2-one;
5-chloro-2-oxo-1-(2-(piperidin-1-yl)ethyl)-3-(pyridin-2-ylmethyl)indolin-3-yl dimethylcarbamate;
N-(3-((3-methoxypyridin-2-yl)methyl)-2-oxo-1-propylindolin-3-yl)benzamide;
N-(5-chloro-1-ethyl-2-oxo-3-(pyridin-2-ylmethyl)indolin-3-yl)-4-methylbenzenesulfonamide;
3-(1-ethyl-5-methyl-3-((1-methyl-1H-indazol-4-yl)methyl)-2-oxoindolin-3-yl)-1,1-dimethylurea;
1,1-dimethyl-3-(3-((1-methyl-1H-indazol-4-yl)methyl)-2-oxo-1-propylindolin-3-yl)urea;
3-(3-(benzo[d][1,3]dioxol-4-ylmethyl)-2-oxo-1-propylindolin-3-yl)-1,1-dimethylurea;
3-(3-(benzo[d][1,3]dioxol-4-ylmethyl)-5-chloro-1-methyl-2-oxoindolin-3-yl)-1,1-dimethylurea;
3-(3-(benzo[d][1,3]dioxol-4-ylmethyl)-5-chloro-2-oxo-1-propylindolin-3-yl)-1,1-dimethylurea;
3-(1,5-dimethyl-2-oxo-3-(3,4,5-trimethoxybenzyl)indolin-3-yl)-1,1-dimethylurea;
3-(1-ethyl-2-oxo-3-(3,4,5-trimethoxybenzyl)indolin-3-yl)-1,1-dimethylurea;
3-(3-((1-benzoyl-1H-indol-3-yl)methyl)-1-ethyl-2-oxoindolin-3-yl)-1,1-dimethylurea;
3-(3-((1-benzoyl-1H-indol-3-yl)methyl)-1-methyl-2-oxoindolin-3-yl)-1,1-dimethylurea;
3-(3-((1-benzoyl-1H-indol-3-yl)methyl)-2-oxo-1-propylindolin-3-yl)-1,1-dimethylurea;
3-(3-((1-benzoyl-1H-indol-3-yl)methyl)-5-methyl-2-oxo-1-propylindolin-3-yl)-1,1-dimethylurea;
or
2-((5-chloro-1-ethyl-3-hydroxy-2-oxoindolin-3-yl)methyl)-6-methoxyphenyl dimethylsulfamate.

In another embodiment of the invention, provided is a pharmaceutical composition, comprising a therapeutically effective amount of a compound according to formula I, or a pharmaceutically acceptable salt thereof, and a pharmaceutically acceptable carrier.

In another embodiment of the invention, provided is a method for treating a degenerative disease or disorder, comprising the step of administering a therapeutically effective amount of a compound according to formula I or a pharmaceutically acceptable salt thereof and a pharmaceutically acceptable carrier to a patient in need thereof. In a further embodiment, the degenerative disease or disorder is retinitis pigmentosa.

In another embodiment of the invention, provided is a method of treating a retinal degenerative disease, comprising the step of administering a therapeutically effective amount of a compound according to formula I or a pharmaceutically acceptable salt thereof and a pharmaceutically acceptable carrier to a patient in need thereof.

In another embodiment of the invention, provided is a method for preventing calcium-induced or oxidant-induced mitochondrial damage preventing or loss of mitochondrial respiratory capacity in a cell susceptible thereof wherein the calcium-induced or oxidant-induced mitochondrial damage or loss of mitochondrial respiratory capacity comprises excess of cGMP that increases the number of cGMP-gated cation channels in an open configuration, allowing an influx of Ca2+ into the cell, said method comprising contacting the cell with an effective amount of a compound or a pharmaceutically acceptable salt thereof according to formula I.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions.

The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are representative liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. In one embodiment, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

The compounds of formula I can be prepared according to the following schemes:

Scheme 1

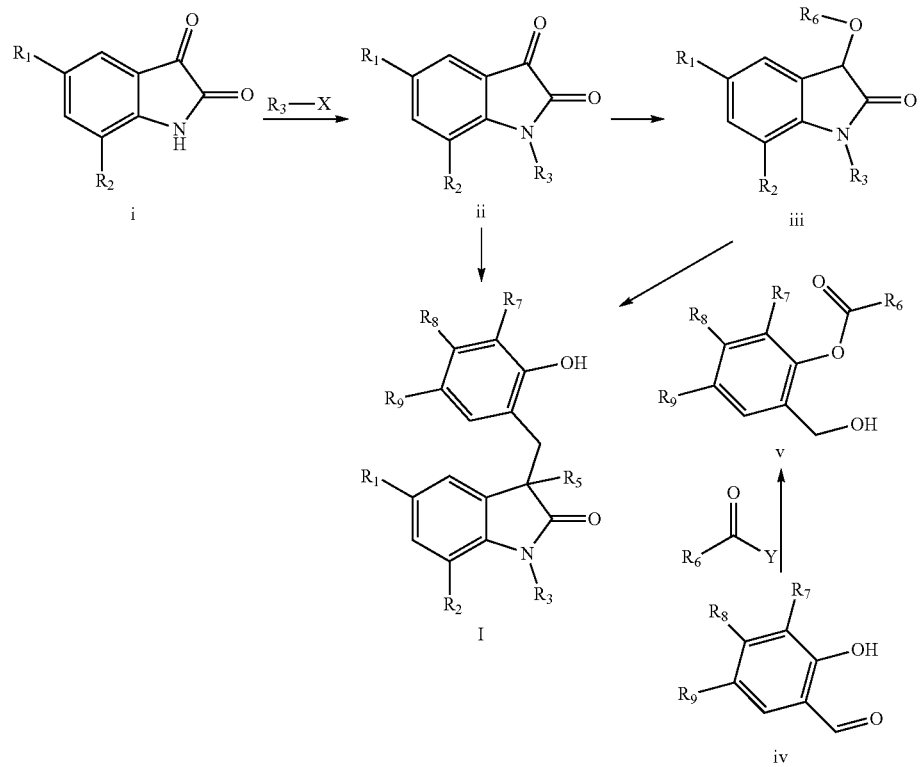

As shown in Scheme 1, compounds of formula (I) can be made by reacting the starting isatin (i), having the substitution pattern of R1 and R2 where R1 and R2 can be, for example, hydrogen, alkyl, methyl, ethyl, chloro-, bromo-, iodo, or any alkyl or halide and may be purchased from common commercial vendors (such as Fisher Scientific, VWR, Aldrich, Ryan Scientific), with R3-X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. R3 may be defined, for example, as alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1 20091119), piperidin-1-yl)ethyl, phenethyl, or any other common make up of a hydrocarbon chain. This reaction may be carried out in anhydrous acetonitrile or anhydrous N,N-dimethyl formamide (purchased from commercial sources). In the case of intermediate ii where R3 is pent-4-yn-1-yl, a separate reaction can be performed to prepare the necessary leaving group X. This may be done by converting the commercially available pent-4-yn-1-ol into pent-4-yn-1-yl 4-methylbenzenesulfonate using commercially available tosyl chloride under basic conditions (e.g., triethyl amine) in a solvent such as dichloromethane. Compounds of formula I may be made by reacting intermediate ii with any ketone in the presence of an amine base such as diethyl amine, dimethyl amine, di-isopropyl amine, proline, or any substitution therein. R4 may be, for example, hydrogen, aryl, phenyl, indolin, 2-pyridinyl, 2-pyridyl, 6-methoxypyridin-2-yl, 2,6-dimethoxypyridin-3-yl, 6-ethynylpyridin-2-yl, or any other aromatic derivative therein. R5 may be, for example, hydroxyl, amine, hydrogen, benzoate, methyl carbonate or tert-butyl carbonate, N,N-dimethylcarbamate, or a carbamate where the nitrogen is singly alkylated, or doubly alkylated or sulfamate where the nitrogen is singly alkylated, or doubly alkylated. This is made in a similar way to a protocols outlined in Allu, Suresh et al., Tetrahedron Letters (2011), 52(32), 4080-4083; Pandeya, S. et al., Acta Ciencia Indica, Chemistry (2007), 33(4), 549-561; Macaev, F. Z. et al., Chemistry of Heterocyclic Compounds (New York, N.Y., United States) (2007), 43(3), 298-305; and Lopez-Alvarado, Pilar and Avendano, Carmen Synthesis (2002), (1), 104-110. R6 may be defined —C(O)-pyridinyl, —P(O)(OCH$_2$CH$_3$)$_2$, —C(O)CH$_2$OCH$_3$, —C(O)N(CH$_3$)$_2$, —C(O)—O-1,3-dioxolan-4-yl)methyl and —C(O)-phenyl.

Scheme 2

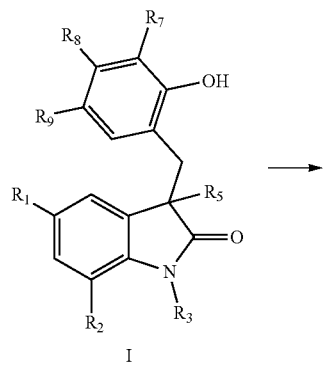

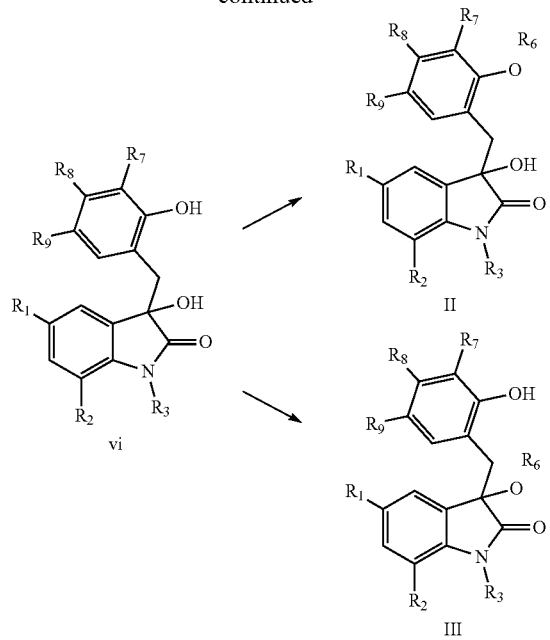

As shown in Scheme 2, compounds of formula II may be made by reacting the starting isatin (i), having the substitution pattern of R1 and R2 that may be, for example, hydrogen, alkyl, methyl, ethyl, chloro-, bromo-, iodo, or any other alkyl or halide and may be purchased from common commercial vendors, with R3-X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. This reaction may be carried out in anhydrous acetonitrile or anhydrous N,N-dimethyl formamide. R3 may be defined as alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1 20091119), piperidin-1-yl)ethyl, phenethyl, or any other common make up of a hydrocarbon chain. In the case of, pent-4-yn-1-yl for intermediate ii, a separate reaction can be performed to prepare the necessary leaving group X. This may be done by converting the commonly commercially available pent-4-yn-1-ol into pent-4-yn-1-yl 4-methylbenzenesulfonate using commercially available tosyl chloride under basic conditions (e.g., triethyl amine) in a solvent such as dichloromethane. Intermediate iii may be made by reducing intermediate ii using common reducing agents (e.g., NaBH$_4$, BH$_3$, DIBAL) and its subsequent protection where R6 may be defined as methyl, isobutyl, tert-butyl, phenyl, methyl ether, ethyl ether, dimethyl amine, or any other ether, poly substituted amine, alkyl or aryl group. This protection may be done under basic condition (e.g., NEt3 DIPEA, DMAP) in solvents like anhydrous dichloromethane (purchased from Fisher Scientific stored under 4 angstrom molecular sieves) or anhydrous THF (purchased from common vendors). Compound of formula II may be made by reacting intermediate iii with intermediate v. Intermediate v can be made from intermediate iv. Intermediate iv can be commercially available variants on the benzaldehyde backbone where R7, R8, and R9 may be hydrogen, methyl ether, alkyl ether, or derivative therein. Protection of the phenolic motif of intermediate iv may be done under basic conditions (e.g., NaH, NEt3, DMAP, DIPEA) that can result in a formate where R6 may be alkyl, methyl, isopropyl, phenyl, t-butyl, oxy-methyl, or oxy-tertbutyl that are derived from commercial sources. Y may be, for example, as chloride, bromide, or tertbutyl carbonate. Reduction of the aldehyde to afford intermediate iv may be done using common reducing regents such as $NaBH_4$, DIBAL, $BH_3$ or any other common reducing agent. The reaction may occur in THF/water mixtures to afford intermediate v. Formula of compound II may occur by reacting the intermediate iii with a strong base (e.g., LiHMDS, KHMDS, LDA) followed by exposure to intermediate v. This reaction may take place in solvents like THF, toluene, and DMF.

can be performed to prepare the necessary leaving group X. This may be done by converting the commonly commercially available pent-4-yn-1-ol into pent-4-yn-1-yl 4-methylbenzenesulfonate using commercially available tosyl chloride under basic conditions (e.g., triethyl amine) in a solvent such as dichloromethane. Intermediate iii may be made by reducing intermediate ii using common reducing agents (e.g., $NaBH_4$, $BH_3$, DIBAL) and its subsequent protection where R6 may be defined as methyl, isobutyl, tert-butyl, phenyl, methyl ether, ethyl ether, dimethyl amine, or any other ether, poly substituted amine, alkyl or aryl group. This reaction may be done under basic condition (e.g., NEt3 DIPEA, DMAP) in solvents like anhydrous dichloromethane (purchased from Fisher Scientific stored under 4 ang-

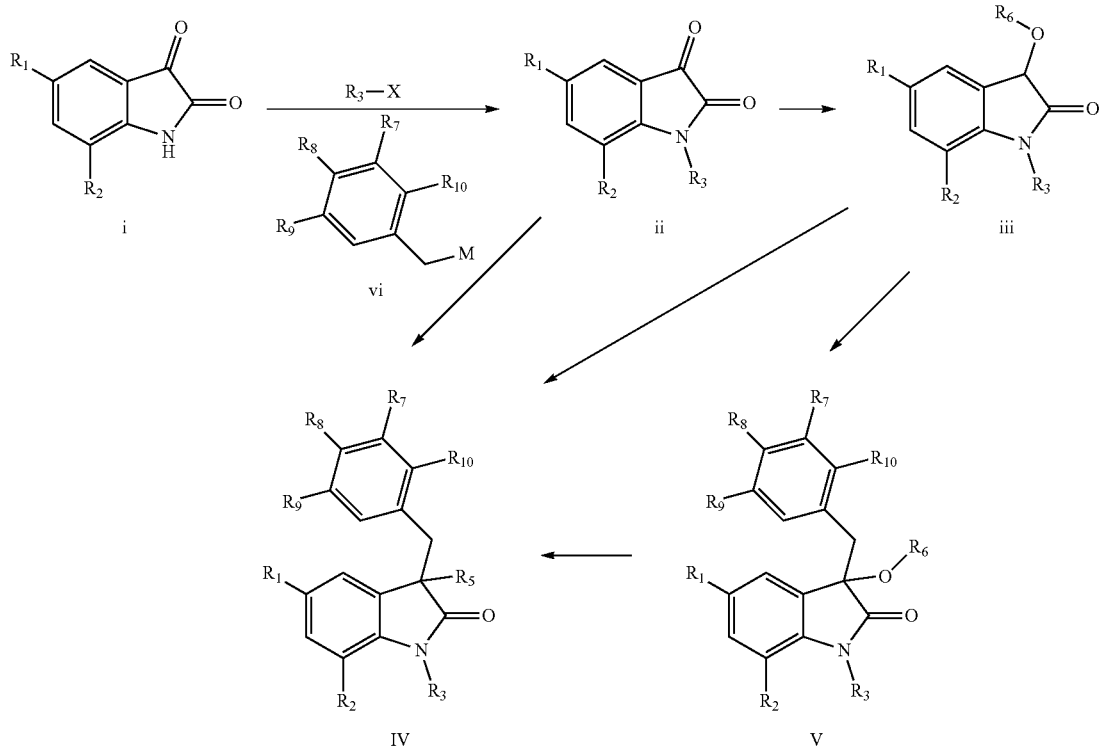

Scheme 3

According to Scheme 3, compounds of formula III may be made in the following manner: reacting the starting isatin (i), having the substitution pattern of R1 and R2 that may be, for example, hydrogen, alkyl, methyl, ethyl, chloro-, bromo-, iodo, or any other alkyl or halide and may be purchased from common commercial vendors, with R3-X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. This reaction may be carried out in anhydrous acetonitrile or anhydrous N,N-dimethyl formamide. R3 may be defined as alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1 20091119), piperidin-1-yl)ethyl, phenethyl, or any other common make up of a hydrocarbon chain. In the case of pent-4-yn-1-yl for intermediate ii, a separate reaction strom molecular sieves). Intermediate iii can then be reacted with a base, like LiHMDS, and combined with commercially available (from, for example, Fisher Scientific or Aldrich) benzylic halides (e.g., 2-methoxyl benzyl chloride, 3-methoxy benzyl chloride, 4-methoxy benzyl chloride, 3,4,5-trimethoxy benzyl chloride, 3,5 dimethoxy benzyl bromide) to form final compound III. In some cases, 3,4 dimethoxy benzyl bromide may be used. For these instances, conversion of the commercially available 3,4 dimethoxy benzyl alcohol purchased from Fisher Scientific, to the corresponding benzyl bromide may be done using PBr3 in a solvent like anhydrous dichloromethane.

Compound of formula IV may be made by reacting intermediate iii with any commercial benzylic halide. Intermediate iii may be made by reducing intermediate ii using common reducing agents (e.g., $NaBH_4$, $BH_3$, DIBAL) and its subsequent protection where R6 may be, for example, methyl, isobutyl, tert-butyl, phenyl, methyl ether, ethyl ether, dimethyl amine, or any other ether, poly substituted amine, alkyl or aryl group. This reaction may be done under basic condition (e.g., NEt3 DIPEA, DMAP) in solvents like anhydrous dichloromethane (purchased from Fisher Scientific stored under 4 angstrom molecular sieves). Intermediate iii can then be reacted with a base, like LiHMDS, and combined with commercially available (from either Fisher Scientific or Aldrich) benzylic halides (e.g., 2-methoxyl benzyl chloride, 3-methoxy benzyl chloride, 4-methoxy benzyl chloride, 3,4,5-trimethoxy benzyl chloride, 3,5 dimethoxy benzyl bromide) to form final compound III where R7, R8, R9, and R10 may be defined as hydrogen, methyl ether, halide, or any multiple or derivative therein. In some cases, 3,4 dimethoxy benzyl bromide may be used. For these instances, conversion of the commercially available 3,4 dimethoxy benzyl alcohol purchased from Fisher Scientific, to the corresponding benzyl bromide may be done using PBr3. This type of transformation may also be accomplished using triphenylphosphine any carbontetrahalide in a solvent such as anhydrous dichloromethane (commercially available from common sources).

NaBH$_4$), or organometallic (alkyl Grignard or alkyl lithium) using a common anhydrous solvent like THF.

Compounds of formula IV may also be made by forming the Grignard or any other organometallic reagent from using intermediate vi. Intermediate vi may be made from commercially available benzylic halides (e.g., 2-methoxyl benzyl chloride, 3-methoxy benzyl chloride, 4-methoxy benzyl chloride, 3,4,5-trimethoxy benzyl chloride, 3,5 dimethoxy benzyl bromide). M may be lithium, magnesium chloride, magnesium bromide, magnesium iodide, sodium or any other metallic reagent to form final compound III where R7, R8, R9, and R10 may be defined as hydrogen, methyl ether, halide, or any multiple or derivative therein. In some cases, 3,4 dimethoxy benzyl bromide may be used. For these instances, conversion of the commercially available 3,4 dimethoxy benzyl alcohol purchased from Fisher Scientific, to the corresponding benzyl bromide may be done using PBr3.

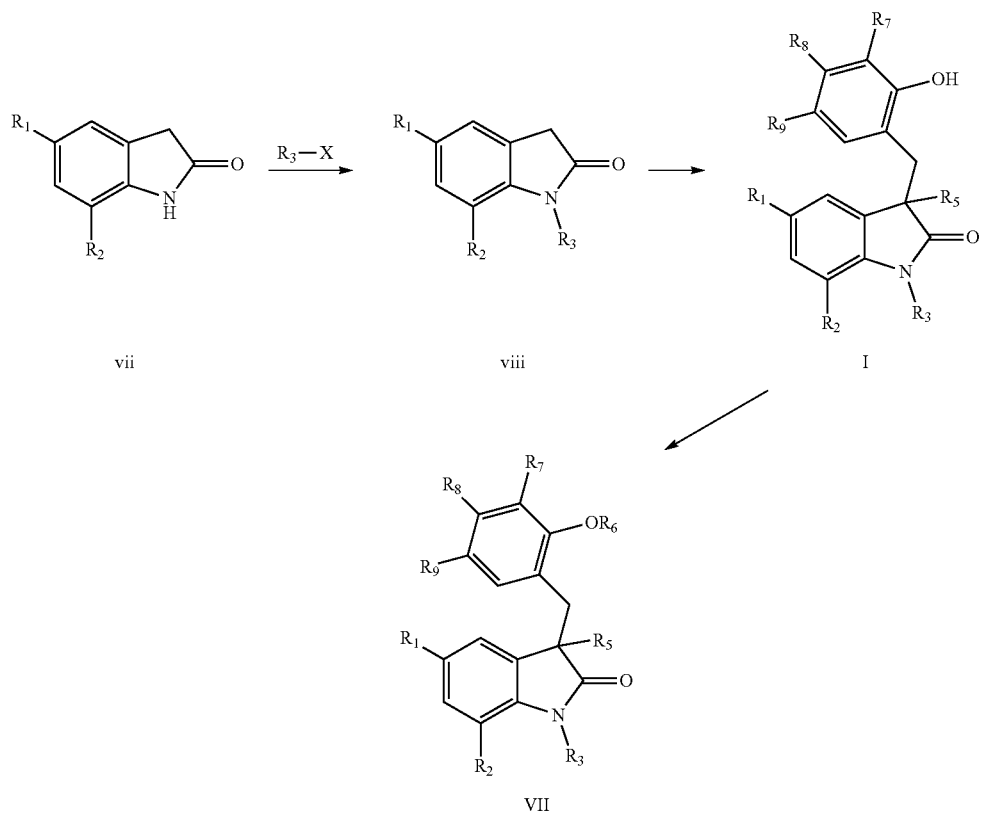

Scheme 4

Compounds of formula IV can also be made by the reaction compounds of formula III under basic conditions. This reaction may be done under basic conditions (e.g., potassium hydroxide, sodium hydroxide, potassium carbonate, sodium carbonate) in a solvent like methanol, methanol with water, ethanol, ethanol with water, or water. This reaction may be accelerated by the use of a microwave or other conventional heating or refluxing. This may form compounds of formula IV with an R5 substitution.

Compounds of formula IV may also be made by the exposure of compound III to a common reducing agent (e.g., As seen in Scheme 4, compounds of formula V may be made by reacting the starting isatin (i), having the substitution pattern of R1 and R2 that may be, for example, hydrogen, alkyl, methyl, ethyl, chloro-, bromo-, iodo, or any other alkyl or halide and may be purchased from common commercial vendors, with R3-X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. This reaction may be carried out in anhydrous acetonitrile or anhydrous N,N-dimethyl formamide. R3 may be, for example, alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1 20091119), piperidin-1-yl)ethyl, phenethyl, or any other common make up of a hydrocarbon chain. In the case of, pent-4-yn-1-yl for intermediate ii, a separate reaction can be performed to prepare the necessary leaving group X. This may be done by converting the commonly commercially available pent-4-yn-1-ol into pent-4-yn-1-yl 4-methylbenzenesulfonate using commercially available tosyl chloride under basic conditions (e.g., triethyl amine) in a solvent such as dichloromethane. Intermediate iii may be made by reducing intermediate ii using common reducing agents (e.g., NaBH$_4$, BH$_3$, DIBAL) and its subsequent protection where R6 may be defined as methyl, isobutyl, tert-butyl, phenyl, methyl ether, ethyl ether, dimethyl amine, or any other ether, poly substituted amine, alkyl or aryl group. This reaction may be done under basic condition (e.g., NEt3 DIPEA, DMAP) in solvents like anhydrous dichloromethane (purchased from Fisher Scientific stored under 4 angstrom molecular sieves). Intermediate vii may be made by reacting commercially available (1H-indol-3-yl)methanol with benzoyl chloride in the presence of triethyl amine and N,N-dimethyl aminepyridine to afford a product where R11 may be hydrogen or the corresponding benzamide (PhCO). This reaction may take place in a solvent such as anhydrous dichloromethane. Intermediate iii can then be reacted with a base, like LiHMDS or KHMDS with intermediate vii to form compounds of formula V. This reaction may occur in solvents like toluene and DMF.

The invention will now be further described in the Examples below, which are intended as an illustration only and do not limit the scope of the invention.

EXAMPLES

I. Preparation of Certain Intermediates tert-butyl (2-(hydroxymethyl)-4,5-dimethoxyphenyl) carbonate

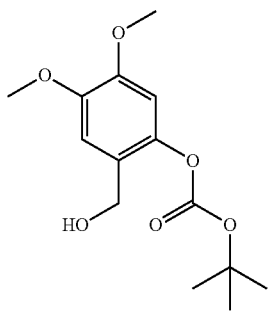 [SMILES: COc1cc(CO)c(OC(=O)OC(C)(C)C)cc1OC]

To a flask was charged with 1.5 mmol of crude phenol, was added DMAP (0.018 grams, 0.15 mmol) and 3.0 mL of THF. While stirring at room temperature di-tert-butyl-dicarbonate (0.327 grams, 1.5 mmol) was added. Once completed, the reaction was concentrated and purified using a Teledyne ISCO combiflash Rf on silica support (hexanes/ethyl acetate gradient) afforded the desired compound. (0.316 grams, 75% yield from the trimethoxybenzaldehyde).

To a flask charged with the aldehyde (0.326 grams, 1.12 mmol) was added 5.0 mL of THF. The stirring solution was cooled to 0° C. In a separate flask NaBH$_4$ (0.0466 grams, 1.23 mmol) was taken up in 1.0 mL water. The NaBH$_4$ solution was then added to the aldehyde. After 30 seconds, the reaction was quenched with 1.0M HCl. The organic material was extracted using Ethyl acetate. The aqueous layer was salted out, and washed with ethyl acetate two times. The combined organic solution was dried with Na2SO4, filtered and concentrated. Once completed the reaction was concentrated and purified using a Teledyne ISCO combiflash Rf on silica support (hexanes/ethyl acetate gradient) afforded the desired compound. (0.19 grams, 54% yield). 1H-NMR (CDCl3) δ 6.97 (s, 1H), 6.67 (s, 1H), 4.54 (s, 2H), 3.90 (s, 3H), 3.88 (s, 3H), 1.75 (BS, OH), 1.57 (s, 9H).

tert-butyl (6-(hydroxymethyl)-2,3-dimethoxyphenyl) carbonate

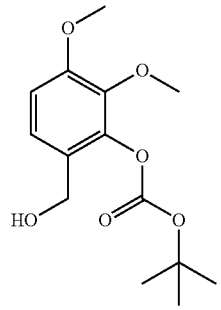

This was prepared in a similar way to tert-butyl (2-(hydroxymethyl)-4,5-dimethoxyphenyl) carbonate using the known demethylation protocol. 1H-NMR (CDCl3) δ 7.11 (d, 1H), 6.82 (d, 1H), 4.58 (s, 2H), 3.88 (s, 3H), 3.87 (s, 3H), 1.60 (BS, OH), 1.57 (s, 9H).

1-ethyl-5-methyl-2-oxoindolin-3-yl dimethylcarbamate

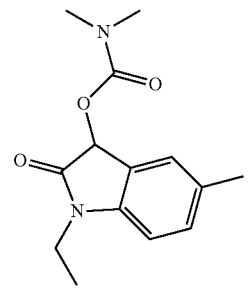 [SMILES: CCN1C(=O)C(OC(=O)N(C)C)c2cc(C)ccc21]

To a clean flask was added 5-methyl-1-ethylindoline-2,3-dione (5.0 grams, 26.4 mmol) and 99.0 mL of THF. In a separate flask charged with NaBH$_4$ (1.1 grams, 29.1 mmol) was added 33.0 mL of H2O. The NaBH$_4$ solution was then added to the 5-methyl-1-ethylindoline-2,3-dione solution at room temperature. The reaction was monitored by LCMS. Once all of the starting material was consumed, approximately 2 minutes, the reaction was quenched using 1.0 M HCl. The solution was salted out, and extracted with ethyl acetate. The aqueous layer was then washed twice with ethyl acetate and the organic material combined. The organic solution was dried with Na2SO4, filtered, and concentrated. It was then used for the next step without any further purification.

To a flask charged with the reduced 5-methyl-1-ethylindoline-2,3-dione (26.4 mmol) was added DMAP (0.3259 grams, 2.64 mmol). This was taken up in anhydrous $CH_2Cl_2$ (120 mL). While stirring at room temperature, triethylamine (5.5 mL, 39.6 mmol) was added followed by dimethyl carbamoyl chloride (2.4 mL, 26.4 mmol). The reaction was monitored by LCMS. Once complete, the reaction was diluted with water. The organic material was extracted using dichloromethane. The aqueous layer was washed two times with dichloromethane. The combined organic solution was washed with brine, dried with Na2SO4, filtered, and concentrated. Purification using a Teledyne ISCO combiflash Rf on silica support (hexanes/ethyl acetate gradient) afforded the desired compound. (3.3 grams, 48% over 2 steps) Calculated mass for Chemical Formula, $C_{14}H_{18}N_2O_3$, 262.13 observed 263.1 (M+1, MM APCI/ESI)

tert-butyl (6-(hydroxymethyl)-2,3-dimethoxyphenyl) carbonate

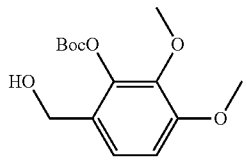

To a flask charged with crude 2-hydroxy-3,4-dimethoxybenzaldehyde (4.55 grams, 25.5 mmol) was added DMAP (0.311 grams, 2.55 mmol). This was taken up in 25.0 mL of THF. While stirring at room temperature, a solution of ditertbutyldicarbonate (26.0 mL, 25.5 mmol, 1.0M in THF) was added. The reaction was monitored by LCMS. Once complete, the solvent was removed using a rotary evaporator. Purification using a Teledyne ISCO combiflash Rf on silica support (hexanes/ethyl acetate gradient) afforded the desired compound.

To a flask charged with tert-butyl (6-formyl-2,3-dimethoxyphenyl) carbonate (1.10 grams, 3.9 mmol) was added 10.0 mL THF. The organic solution was cooled to 0° C. In a separate charged with NaBH$_4$ (0.163 grams, 4.3 mmol) was added 3.0 mL of H2O. The NaBH$_4$ solution was then added to the tert-butyl (6-formyl-2,3-dimethoxyphenyl) carbonate solution at 0° C. The reaction was monitored by LCMS. Once all of the starting material was consumed, approximately 30 seconds, the reaction was quenched using 1.0 M HCl. The solution was salted out, and extracted with ethyl acetate. The aqueous layer was then washed twice with ethyl acetate and the organic material combined. The organic solution was dried with Na$_2$SO$_4$, filtered, and concentrated. Purification using a Teledyne ISCO combiflash Rf on silica support (hexanes/ethyl acetate gradient) afforded the desired compound. (0.61 grams, 55% yield). Calculated mass for Chemical Formula: $C_{14}H_{20}O_6$, 284.13, observed.

2-oxo-1-propylindolin-3-yl dimethylcarbamate

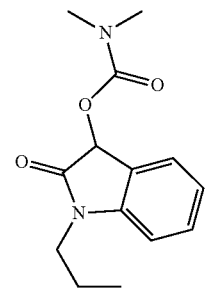 [SMILES: CCCN1C(=O)C(OC(=O)N(C)C)c2ccccc21]

This intermediate was be made using a similar method to 1-ethyl-5-methyl-2-oxoindolin-3-yl dimethylcarbamate. Chemical Formula: $C_{14}H_{18}N_2O_3$, 262.13; observed 263.1 (M+1, MM API/ESI).

5-chloro-1-methyl-2-oxoindolin-3-yl dimethylcarbamate

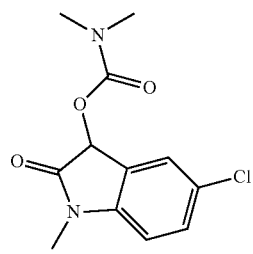 [SMILES: CN(C)C(=O)OC1C(=O)N(C)c2ccc(Cl)cc21]

This intermediate was be made using a similar method to 1-ethyl-5-methyl-2-oxoindolin-3-yl dimethylcarbamate Calculated mass for Chemical Formula: $C_{12}H_{13}ClN_2O_3$, 268.06, observed 269.1 (M+1, MM API/ESI).

(5-chloro-2-oxo-1-propylindolin-3-ylidene)nicotinamide

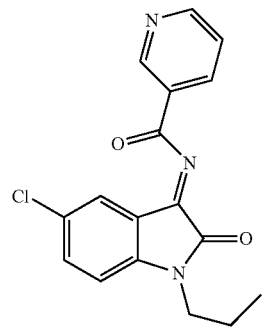 [SMILES: CCCN1C(=O)/C(=N/C(=O)c2cccnc2)c2cc(Cl)ccc21]

To an oven dried flask that was cooled under argon was added 5-chloro-1-propylindoline-2,3-dione (0.50 grams, 2.24 mmol) and nicotinamide (0.343 grams, 2.69 mmol). This was taken up in 4.5 mL of dichloromethane. While stirring at room temperature Ti(OiPr)4 (0.73 mL, 2.46 mmol) was added. The reaction stirred under an inert atmosphere overnight at room temperature. The next day the solution was concentrated onto a celite support. Purification using a Teledyne ISCO combiflash Rf on silica support (hexanes w/0.1% NEt3/ethyl acetate gradient) afforded the desired compound (0.508 grams, 69% yield). Calculated mass for Chemical Formula: $C_{17}H_{14}ClN_3O_2$, 327.08, observed, 328.2 (M+1, MM API/ESI).

N-(1-methyl-2-oxoindolin-3-ylidene)nicotinamide

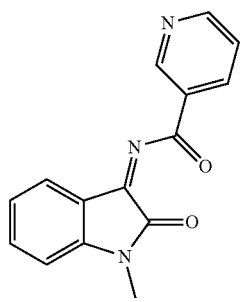 [SMILES: CN1C(=O)/C(=N\C(=O)c2cccnc2)c2ccccc21]

This compound can be made using a similar method to N-(5-chloro-2-oxo-1-propylindolin-3-ylidene)nicotinamide. (1.36 grams, 83% yield). Calculated mass for Chemical Formula: $C_{15}H_{11}N_3O_2$, 265.09, observed 266.1 (M+1, MM API/ESI).

N-(1-ethyl-2-oxoindolin-3-ylidene)isonicotinamide

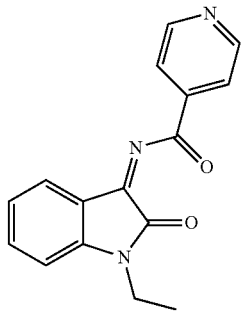 [SMILES: CCN1C(=O)/C(=N\C(=O)c2ccncc2)c2ccccc21]

This compound can be made using a similar method to N-(5-chloro-2-oxo-1-propylindolin-3-ylidene)nicotinamide. (0.33 grams, 23% yield). Calculated mass for Chemical Formula: $C_{16}H_{13}N_3O_2$, 279.10, observed 280.2 (M+1, MM API/ESI).

N-(5-chloro-2-oxo-1-propylindolin-3-ylidene)benzamide

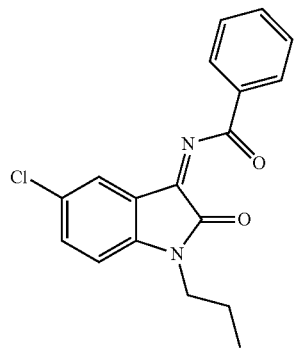 [SMILES: CCCN1C(=O)/C(=N\C(=O)c2ccccc2)c2cc(Cl)ccc21]

This compound can be made using a similar method to N-(5-chloro-2-oxo-1-propylindolin-3-ylidene)nicotinamide. (0.5676, 39% yield). Calculated mass for Chemical Formula: $C_{18}H_{15}ClN_2O_2$, 326.08, observed 327.1 (M+1, MM API/ESI).

N-(2-oxo-1-propylindolin-3-ylidene)benzamide

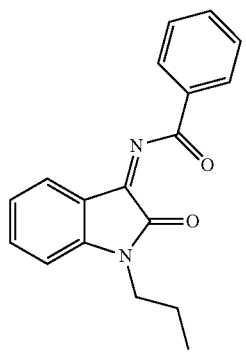 [SMILES: CCCN1C(=O)/C(=N\C(=O)c2ccccc2)c2ccccc21]

This compound can be made using a similar method to N-(5-chloro-2-oxo-1-propylindolin-3-ylidene)nicotinamide. (0.7889 grams, 51% yield). Calculated mass for Chemical Formula: $C_{18}H_{16}N_2O_2$, 292.12, observed 293.2 (M+1, MM API/ESI).

N-(5-chloro-1-ethyl-2-oxoindolin-3-ylidene)-4-methylbenzenesulfonamide

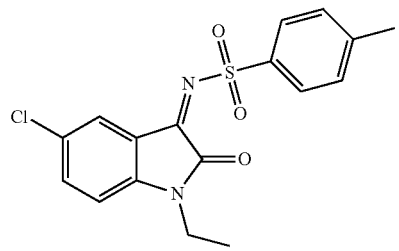 [SMILES: CCN1C(=O)/C(=N\S(=O)(=O)c2ccc(C)cc2)c2cc(Cl)ccc21]

To an oven dried vial cooled under argon equipped with a stir bar was added 5-chloro-1-ethylindoline-2,3-dione (500 mg, 2.39 mmol; WO 2014160143) and para-toluene sulfonamide (491 mg, 2.87 mmol). THF (4.8 mL) was then added. While stirring at room temperature, titanium tetraisopropoxide (780 μL, 2.63 mmol) was added, and the resulting solution was allowed to stir overnight. The reaction was concentrated onto celite, and purification was accomplished by using a Teledyne ISCO combiflash silica support (hexanes with 0.1% triethylamine/ethyl acetate gradient). The desired material was isolated in 44% yield (381 mg). Calculated mass for chemical formula: $C_{17}H_{15}ClN_2O_3S$ 362.05, observed, 363.0. (MM: ESI+APCI, M+1).

3-(1-ethyl-5-methyl-2-oxoindolin-3-yl)-1,1-dimethylurea

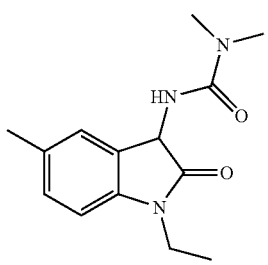

To an oven dried round bottom flask cooled under argon equipped with a stir bar was added 1-ethyl-5-methylindoline-2,3-dione (2.0 g, 10.5 mmol; WO 2014160143) and 1,1-dimethylurea (1.11 g, 12.6 mmol). THF (20 mL) was added. While stirring at room temperature, titanium tetraisopropoxide (3.5 mL, 11.6 mmol) was added, and the reaction was allowed to stir overnight. The crude reaction mixture was carried over to the next step without any purification. Calculated mass for chemical formula: $C_{14}H_{17}N_3O_2$ 259.13, observed, 260.1. (MM: ESI+APCI, M+1).

The crude reaction mixture of 3-(1-ethyl-5-methyl-2-oxoindolin-3-ylidene)-1,1-dimethylurea was cooled down to 0° C. While stirring, a solution of sodium borohydride (437 mg, 11.55 mmol) in methanol (60 mL) was slowly added. The reaction was stirred until the starting material had been consumed. The reaction was quenched with 1.0 M HCl (46 mL) at 0° C. The reaction was concentrated down until two layers were visible. The mixture was salted out and extracted with ethyl acetate. The aqueous layer was washed with ethyl acetate and acetonitrile. The combined organic material was dried over $Na_2SO_4$, filtered, and concentrated. Purification was accomplished using a Teledyne ISCO combiflash silica support (hexanes/ethyl acetate gradient followed by an acetonitrile flush) to afford the desired material in 32% yield (877 mg). Calculated mass for chemical formula: $C_{14}H_{19}N_3O_2$ 261.15, observed, 262.1. (MM: ESI+APCI, M+1).

4-(chloromethyl)-1-methyl-1H-indazole

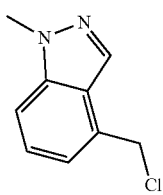

This compound was prepared using the known procedure in U.S. Pat. No. 9,018,210.

1,1-dimethyl-3-(2-oxo-1-propylindolin-3-yl)urea

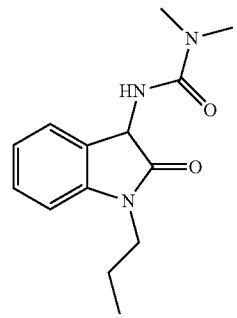 [SMILES: CCCN1C(=O)C(NC(=O)N(C)C)c2ccccc21]

1,1-dimethyl-3-(2-oxo-1-propylindolin-3-ylidene)urea was made in a similar manner to 3-(1-ethyl-5-methyl-2-oxoindolin-3-ylidene)-1,1-dimethylurea, using 1-propylindoline-2,3-dione (U.S. Pat. No. 9,079,853) and 1,1-dimethylurea as the starting materials. Calculated mass for chemical formula: $C_{14}H_{19}N_3O_2$ 261.15, observed, 262.1. (MM: ESI+APCI, M+1).

4-(chloromethyl)benzo[d][1,3]dioxole

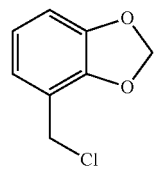 [SMILES: ClCc1cccc2c1OCO2]

This was made using the known procedure in U.S. Pat. No. 8,022,062.

5-chloro-1-methylindoline-2,3-dione

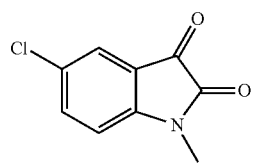

5-chloro-1-methylindoline-2,3-dione was made in a similar manner to 5-chloro-1-ethylindoline-2,3-dione. Purification was accomplished using a Teledyne ISCO combiflash silica support (hexanes/ethyl acetate gradient) to afford the desired compound as a red solid in 91% yield.

3-(5-chloro-1-methyl-2-oxoindolin-3-yl)-1,1-dimethylurea

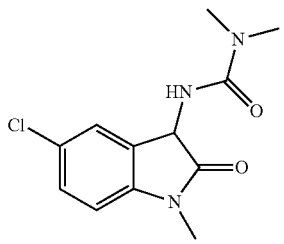 [SMILES: CN(C)C(=O)NC1C(=O)N(C)c2ccc(Cl)cc21]

3-(5-chloro-1-methyl-2-oxoindolin-3-ylidene)-1,1-dimethylurea was made in a similar way to 3-(1-ethyl-5-methyl-2-oxoindolin-3-ylidene)-1,1-dimethylurea, using 5-chloro-1-methylindoline-2,3-dione (Damgaard, Maria; Al-Khawaja, Anas; Vogensen, Stine B.; Jurik, Andreas; Sijm, Maarten; Lie, Maria E. K.; Baek, Mathias I.; Rosenthal, Emil; Jensen, Anders A.; Ecker, Gerhard F.; et al ACS Chemical Neuroscience (2015), 6(9), 1591-1599) and 1,1-dimethylurea as the starting materials. The crude reaction material was carried forward to the next step without any purification. Purification was accomplished using a Teledyne ISCO combiflash silica support (hexanes/ethyl acetate gradient followed by an acetonitrile flush) to afford the desired material in 48% yield. Calculated mass for chemical formula: $C_{12}H_{14}ClN_3O_2$ 267.08, observed, 268.1. (MM: ESI+APCI, M+1).

3-(5-chloro-2-oxo-1-propylindolin-3-yl)-1,1-dimethylurea

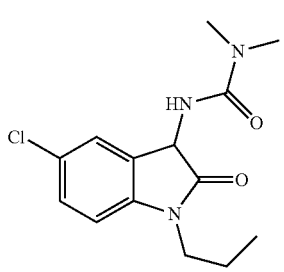 [SMILES: CCCN1C(=O)C(NC(=O)N(C)C)c2cc(Cl)ccc21]

3-(5-chloro-2-oxo-1-propylindolin-3-ylidene)-1,1-dimethylurea was made in a similar way to 3-(1-ethyl-5-methyl-2-oxoindolin-3-ylidene)-1,1-dimethylurea, using 5-chloro-1-propylindoline-2,3-dione and 1,1-dimethylurea as the starting materials. Purification was accomplished using a Teledyne ISCO combiflash silica support (hexanes/ethyl acetate gradient followed by an acetonitrile flush) to afford the desired material in 30% yield. Calculated mass for chemical formula: $C_{14}H_{18}ClN_3O_2$ 295.11, observed, 296.1. (MM: ESI+APCI, M+1).

3-(1,5-dimethyl-2-oxoindolin-3-yl)-1,1-dimethylurea

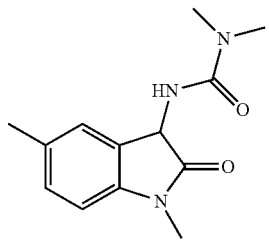

3-(1,5-dimethyl-2-oxoindolin-3-ylidene)-1,1-dimethylurea was made in a similar way to 3-(1-ethyl-5-methyl-2-oxoindolin-3-ylidene)-1,1-dimethylurea, using 1,5-dimethylindoline-2,3-dione (Boechat, Nubia; Kover, W. Bruce; Bongertz, Vera; Bastos, Monica M.; Romeiro, Nelilma C.; Azevedo, Maria L. G.; Wollinger, Wagner Medicinal Chemistry (2007), 3(6), 533-542) and 1,1-dimethylurea as the starting materials. Purification was accomplished using a Teledyne ISCO combiflash silica support (hexanes/ethyl acetate gradient followed by an acetonitrile flush) to afford the desired material in 57% yield. Calculated mass for chemical formula: $C_{13}H_{17}N_3O_2$ 247.13, observed, 248.2. (MM: ESI+APCI, M+1).

3-(1-ethyl-2-oxoindolin-3-yl)-1,1-dimethylurea

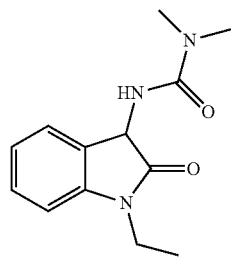 [SMILES: CCN1C(=O)C(NC(=O)N(C)C)c2ccccc21]

3-(1-ethyl-2-oxoindolin-3-ylidene)-1,1-dimethylurea was made in a similar way to 3-(1-ethyl-5-methyl-2-oxoindolin-3-ylidene)-1,1-dimethylurea, using 1-ethylindoline-2,3-dione[i] and 1,1-dimethylurea as the starting materials. Purification was accomplished using a Teledyne ISCO combiflash silica support (hexanes/ethyl acetate gradient followed by an acetonitrile flush) to afford the desired material in 52% yield. Calculated mass for chemical formula: $C_{13}H_{17}N_3O_2$ 247.13, observed, 248.2. (MM: ESI+APCI, M+1).

(1-benzoyl-1H-indol-3-yl)methyl benzoate

This compound was made using the previously described procedure in U.S. Pat. No. 9,079,853.

1,1-dimethyl-3-(1-methyl-2-oxoindolin-3-yl)urea

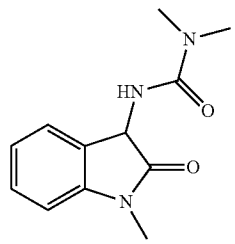 [SMILES: CN(C)C(=O)NC1C(=O)N(C)c2ccccc21]

1,1-dimethyl-3-(1-methyl-2-oxoindolin-3-ylidene)urea was made in a similar way to 3-(1-ethyl-5-methyl-2-oxoindolin-3-ylidene)-1,1-dimethylurea, using 1-methylindoline-2,3-dione (Cao, Shu-Hua; Zhang, Xiu-Chun; Wei, Yin; Shi, Min European Journal of Organic Chemistry (2011), (14), 2668-2672, S2668/1-S2668/65) and 1,1-dimethylurea as the starting materials. Purification was accomplished using a Teledyne ISCO combiflash silica support (hexanes/ethyl acetate gradient followed by an acetonitrile flush) to afford the desired material in 55% yield. Calculated mass for chemical formula: $C_{12}H_{15}N_3O_2$ 233.12, observed, 234.1. (MM: ESI+APCI, M+1).

1,1-dimethyl-3-(5-methyl-2-oxo-1-propylindolin-3-yl)urea

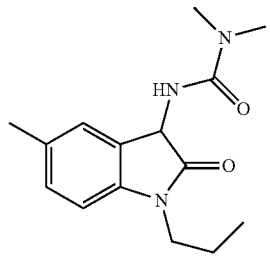

1,1-dimethyl-3-(5-methyl-2-oxo-1-propylindolin-3-ylidene)urea was made in a similar way to 3-(1-ethyl-5-methyl-2-oxoindolin-3-ylidene)-1,1-dimethylurea, using 5-methyl-1-propylindoline-2,3-dione and 1,1-dimethylurea as the starting material. Purification was accomplished using a Teledyne ISCO combiflash silica support (hexanes/ethyl acetate gradient followed by an acetonitrile flush) to afford the desired material in 37% yield. Calculated mass for chemical formula: $C_{15}H_{21}N_3O_2$ 275.16, observed, 276.2. (MM: ESI+APCI, M+1).

II. Preparation of Certain Embodiments of the Invention

Example 1

3-hydroxy-5-methyl-1-(2,2,2-trifluoroethyl)-3-(3,4,5-trimethoxybenzyl)indolin-2-one

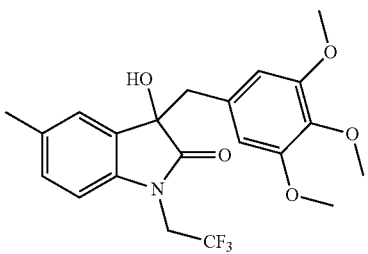

To an oven dried Biotage microwave reaction vial equipped with a stir bar, cooled under an inert atmosphere was added 5-methyl-isatin (0.29 grams, 1.8 mmol) and $K_2CO_3$ (0.249 grams, 1.8 mmol). The mixture was then taken up in 18 mL of anhydrous DMF. After stirring at room temperature for 5 minutes, 2,2,2-trifluoro-1-iodo-ethane (0.35 mL, 3.6 mmol) was added. The vial was then placed in a Biotage Initiator microwave and on a setting of Low was heated to 150° C. for 8 hours. After cooling to room temperature, the solution was concentrated, taken up in dichloromethane and filtered through a plug of celite. The celite plug was rinsed with several washings of dichloromethane until there was no more color coming through the filter. The solution was then concentrated. Purification using a Teledyne ISCO combiflash Rf on silica support (hexanes/ethyl acetate gradient) afforded the desired compound. (0.438 grams, 57% yield).

To a clean flask charged with the isatin (0.498 grams, 2.05 mmol) was added 7.7 mL of THF. In a separate flask $NaBH_4$ (0.085 grams, 2.25 mmol), was taken up in 2.6 mL of H2O. The $NaBH_4$ solution was added to the isatin solution at room temperature. After approximately one minute, the reaction was quenched upon the addition of 1.0M HCl. The organic material was extracted with ethyl acetate. The aqueous layer was salted out and washed two times with ethyl acetate. The combined organic material was dried with $Na_2SO_4$, filtered, and concentrated. It was used for the next step without further purification.

To a clean flask charged with the oxindole (2.05 mmol) was added DMAP (0.025 grams, 0.21 mmol). The mixture was taken up in dichloromethane (21 mL). Triethylamine (0.43 mL, 3.07 mmol) was added followed by careful addition of benzoyl chloride (0.26 mL, 2.25 mmol). Once the reaction was complete, approximately 30 minutes, water was added and the organic material removed. The aqueous layer was washed with dichloromethane. The combined organic material was washed with brine, dried with $Na_2SO_4$, filtered, and concentrated. Purification using a Teledyne ISCO combiflash Rf on silica support (hexanes/ethyl acetate gradient) afforded the desired compound. (0.211 grams, 30% yield).

To an oven dried flask equipped with a stir bar, cooled under an inert atmosphere was added the benzoate (0.07 grams, 0.19 mmol, 0.5 M in toluene). While stirring at room temperature a solution of LiHMDS (0.3 mL, 1.0 M in THF) was added. After stirring for approximately 10 minutes, a solution of 3,4,5-trimethoxy-benzyl chloride (0.061 grams, 0.28 mmols, 0.5 M in DMF) was added. The solution continued to stir at room temperature until the reaction was complete. The reaction was quenched with 1.0M HCl and extracted using ethyl acetate. The aqueous layer was salted out and washed with ethyl acetate followed by acetonitrile. The combined organic solution was then dried with $Na_2SO_4$, filtered and concentrated. Purification using a Teledyne ISCO combiflash Rf on silica support (hexanes/ethyl acetate gradient) afforded the desired compound. (0.0334 grams, 34% yield).

To a clean flask was added the benzoate (0.0334 grams, 0.064 mmol), 0.35 mL of methanol and 0.35 mL of H2O. A solution of KOH (129 uL, 2.0 M in H2O) was added and the solution was heated in a Biotage initiator microwave using a setting of Low for 1 hour at 140° C. Once cooled to room temperature, the solution was acidified using 15 uL of glacial acetic acid. The solvent was then removed using a rotoevaporator. Purification was done using a Teledyne ISCO combiflash Rf on C18 support (water with 0.1% formic acid/acetonitrile gradient) to afford the desire alcohol. Collected 0.004 grams, yield 15%. 1H NMR (CD3OD) δ 7.29 (m, 1H), 7.14 (m, 1H), 6.75 (m, 1H), 6.06 (m, 2H), 4.34 (m, 1H), 4.14 (m, 1H), 3.63 (m, 3H), 3.56 (m, 6H), 3.23 (m, 1H), 3.13 (m, 1H), 2.38 (m, 3H). Calculated mass for Chemical Formula: $C_{21}H_{22}F_3NO_5$, 425.15, observed 461.3 (M+2Na).

Example 2

2-((3-hydroxy-5-methyl-1-(4-methylpentyl)-2-oxoindolin-3-yl)methyl)-5-methoxyphenyl isonicotinate

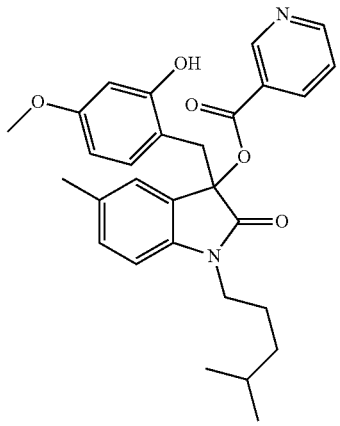 [SMILES: COc1ccc(CC2(OC(=O)c3cccnc3)C(=O)N(CCCC(C)C)c3ccc(C)cc32)c(O)c1]

To a biotage microwave vial charged with the 3-(2-hydroxy-4-methoxybenzyl)-5-methyl-1-(4-methylpentyl)-2-oxoindolin-3-yl benzoate (0.20 grams, 0.41 mmol) was added 2.0 mL of methanol and 2.0 mL of H2O. While stirring at room temperature, KOH (0.8 mL, 1.6 mmol, 2.0 M in H2O) was added. The vial was then sealed and heated to 60° C. overnight. The next day, the solution was acidified using 1.0M HCl and the solution concentrate to approximately half the volume. The mixture was then extracted using ethyl acetate. The aqueous layer was then salted out and washed with ethyl acetate. The combined organic material was then dried with $Na_2SO_4$, filtered and concentrated. Purification using a Teledyne ISCO combiflash Rf on silica support (hexanes/ethyl acetate gradient) afforded the desired compound. (0.153 grams, 97% yield).

To a flame dried flask equipped with a stir was cooled under argon was added nicotinic acid (0.02 grams, 0.15 mmol, 0.2 M in anhydrous dichloromethane). While stirring at room temperature, oxalyl chloride (14.0 uL, 0.17 mmol) was added followed by 1.0 uL of DMF. The solution stirred at room temperature for approximately 45 minutes. A solution of the diol (0.03 grams, 0.078 mmol), triethyl amine (56 uL), and DMAP (0.0017 grams) in 1.3 mL of anhydrous dichloromethane was added. Once complete, the reaction was neutralized using methanol and the solution concentrated. Purification using a Teledyne ISCO combiflash on silica support (hexanes/ethyl acetate gradient) followed by C18 support (water with 0.1% formic acid/acetonitrile gradient) to afford the desired compound. (0.06 grams, 16% yield). 1H NMR (CDCl3) δ 9.17 (s, 1H), 8.85 (m, 2H), 8.39 (d, 1H), 7.50 (dd, 1H), 7.07 (m, 2H), 6.87 (d, 1H), 6.70 (m, 2H), 6.61 (d, 1H), 3.78 (s, 3H), 3.59 (m, 1H), 3.39 (m, 1H), 3.21 (d, 1H), 3.07 (d, 1H), 2.24 (s, 3H), 1.43 (m, 3H), 1.09 (m, 2H), 0.82 (dd, 6H). Calculated mass for $C_{29}H_{32}N_2O_5$ 488.23, observed, 489.2. (ESI, M+1).

Example 3

2-((3-hydroxy-5-methyl-1-(4-methylpentyl)-2-oxoindolin-3-yl)methyl)-5-methoxyphenyl acetate

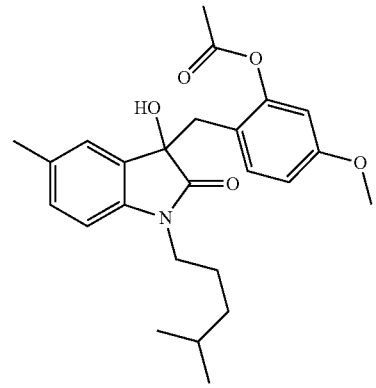

To a Biotage microwave vial charged with 3-(2-hydroxy-4-methoxybenzyl)-5-methyl-1-(4-methylpentyl)-2-oxoindolin-3-yl benzoate (0.200 grams, 0.41 mmol) was added 2.05 mL of methanol and 2.05 mL of water. This was followed by 0.8 mL of 2.0M KOH. The vial was then sealed and heated in a Biotage Initiator microwave at 140° C. on a setting of Low. Once complete, the reaction was acidified with glacial acetic acid. The solvent was then removed. Purification using a Teledyne ISCO combiflash on silica support (hexanes/ethyl acetate gradient) to afford the desired compound. (0.133 grams, 85% yield).

To a flask charged with diol (020 grams, 0.5 mmol) was added DMAP (0.001 gram, 0.008 mmol) and 0.5 mL of anhydrous dichloromethane. While stirring at room temperature, triethylamine (11 uL, 0.078 mmol) followed by acetyl chloride (3.3 uL, 0.057 mmol) was added. The reaction was followed by LCMS. Once complete, the reaction was quenched with methanol, and concentrated. Purification using a Teledyne ISCO combiflash Rf on silica support (hexanes/ethyl acetate gradient) followed by C18 support (water with 0.1% formic acid/acetonitrile gradient) to afford the desired compound. (0.006 grams, 27% yield). 1H NMR (CDCl3) δ 7.06 (d, 1H), 7.01 (d, 1H), 6.94 (d, 1H), 6.58 (m, 3H), 3.73 (s, 3H), 3.61 (m, 1H), 3.41 (m, 1H), 3.16 (d, 1H), 3.04 (d, 1H), 2.32 (s, 3H), 2.24 (s, 3H), 1.85 (BS, OH), 1.48 (m, 3H), 1.45 (m, 2H), 0.85 (dd, 6H). Calculated mass for $C_{25}H_{31}NO_5$ 425.22, observed, 448.2. (ESI, M+Na).

Example 4

2-((3-hydroxy-5-methyl-1-(4-methylpentyl)-2-oxoindolin-3-yl)methyl)-5-methoxyphenyl 2-methoxyacetate

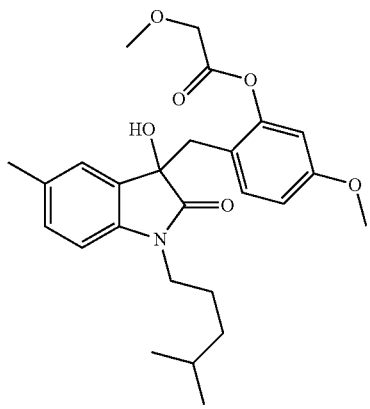

This compound was prepared in a similar manner to 2-((3-hydroxy-5-methyl-1-(4-methylpentyl)-2-oxoindolin-3-yl)methyl)-5-methoxyphenyl acetate: 1H NMR (CDCl3) δ 7.06 (dd, 1H), 6.94 (s, 1H), 6.88 (d, 1H), 6.68 (d, 1H), 6.61 (m, 2H), 4.24 (d, 2H), 3.75 (s, 3H), 3.61 (m, 1H), 3.55 (s, 3H), 3.43 (m, 1H), 3.17 (d, 1H), 3.00 (d, 1H), 2.03 (s, 3H), 1.59 (bs, OH), 1.47 (m, 3H), 1.15 (m, 2H), 0.86 (dd, 6H). Calculated mass for Chemical Formula: $C_{26}H_{33}NO_6$ 455.6, observed, 478.2 (ESI, M+Na).

Example 5

5-chloro-1-ethyl-3-(2-hydroxy-3-methoxybenzyl)-2-oxoindolin-3-yl isonicotinate

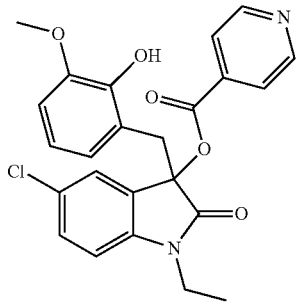 [SMILES: CCN1C(=O)C(Cc2cccc(OC)c2O)(OC(=O)c2ccncc2)c2cc(Cl)ccc21]

This compound was prepared in a similar manner to 2-((3-hydroxy-5-methyl-1-(4-methylpentyl)-2-oxoindolin-3-yl)methyl)-5-methoxyphenyl isonicotinate: 1H NMR (CDCl3) δ 8.81 (m, 2H), 7.90 (m, 2H), 7.24 (dd, 1H), 6.90 (d, 1H), 6.72 (s, 3H), 6.71 (d, 1H), 5.65 (BS, OH), 3.86 (s, 3H), 3.75 (m, 2H), 3.67 (d, 1H), 3.30 (d, 1H), 1.21 (t, 3H). Calculated mass for Chemical Formula: $C_{24}H_{21}ClN_2O_5$ 452.11, observed, 453.1 (ESI, M+1).

Example 6

5-chloro-1-ethyl-3-(2-hydroxy-3-methoxybenzyl)-2-oxoindolin-3-yl picolinate

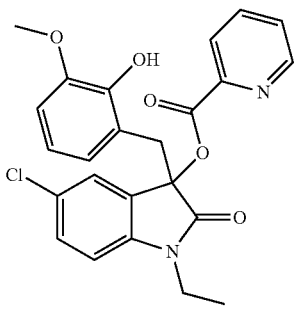 [SMILES: CCN1C(=O)C(Cc2cccc(OC)c2O)(OC(=O)c2ccccn2)c2cc(Cl)ccc21]

This compound was prepared in a similar manner to 2-((3-hydroxy-5-methyl-1-(4-methylpentyl)-2-oxoindolin-3-yl)methyl)-5-methoxyphenyl isonicotinate: 1H NMR (CDCl3) δ 8.80 (dd, 1H), 8.11 (dd, 1H), 7.84 (dd, 1H), 7.51 (dd, 1H), 7.22 (dd, 1H), 6.95 (d, 1H), 6.75 (m, 3H), 6.66 (d, 1H), 6.04 (BS, OH), 3.84 (s, 3H), 3.80 (d, 1H), 3.73 (m, 2H), 3.29 (d, 1H), 1.20 (t, 3H). Calculated mass for Chemical Formula: $C_{24}H_{21}ClN_2O_5$ 452.11 observed, 475.1. (ESI, M+Na).

Example 7

5-chloro-1-ethyl-3-(2-hydroxy-3-methoxybenzyl)-2-oxoindolin-3-yl diethyl phosphate

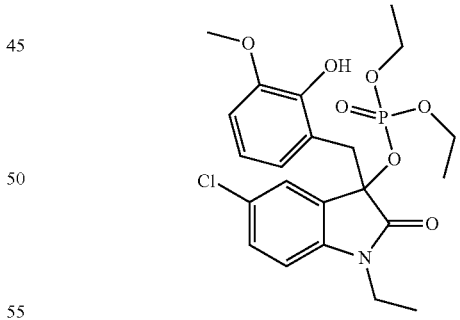

This compound was prepared in a similar manner to 2-((3-hydroxy-5-methyl-1-(4-methylpentyl)-2-oxoindolin-3-yl)methyl)-5-methoxyphenyl acetate: 1H NMR (CDCl3) δ 7.22 (dd, 1H), 7.15 (s, 1H), 6.68 (m, 3H), 6.59 (d, 1H), 5.53 (OH), 4.16 (m, 2H), 3.86 (m, 2H), 3.81 (s, 3H), 3.69 (m, 1H), 3.58 (m, 1H), 3.54 (d, 1H), 3.27 (d, 1H), 1.30 (t, 3H), 1.21 (t, 3H), 1.10 (t, 3H). Calculated mass for Chemical Formula: $C_{22}H_{27}ClNO_7P$ 483.12, observed, 506.1 (ESI, M+Na).

Example 8

2-((5-chloro-1-ethyl-3-hydroxy-2-oxoindolin-3-yl)methyl)-6-methoxyphenyl 2-methoxyacetate

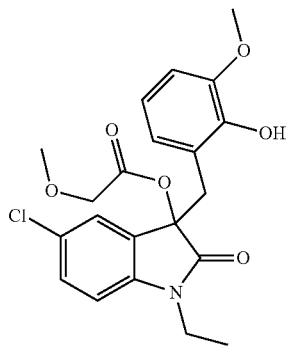 [SMILES: CCN1C(=O)C(Cc2cccc(OC)c2O)(OC(=O)COC)c2cc(Cl)ccc21]

This compound was prepared in a similar manner to 2-((3-hydroxy-5-methyl-1-(4-methylpentyl)-2-oxoindolin-3-yl)methyl)-5-methoxyphenyl acetate: 1H NMR (CDCl3) δ 7.24 (dd, 1H), 7.23 (d, 1H), 7.03 (dd, 1H), 6.83 (dd, 1H), 6.64 (d, 1H), 6.61 (dd, 1H), 4.34 (s, 2H), 3.76 (s, 3H), 3.68 (m, 1H), 3.58 (m, 4H), 3.25 (d, 1H), 3.05 (m, 1H), 1.95 (bs, OH), 1.09 (m, 3H). Calculated mass for Chemical Formula: $C_{21}H_{22}ClNO_6$ 419.11, observed, 442.1. (ESI, M+Na).

Example 9

2-((5-chloro-1-ethyl-3-hydroxy-2-oxoindolin-3-yl)methyl)-6-methoxyphenyl butyrate

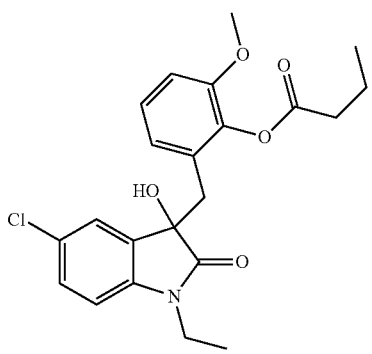 [SMILES: CCCC(=O)Oc1c(CC2(O)C(=O)N(CC)c3ccc(Cl)cc32)cccc1OC]

This compound was prepared in a similar manner to 2-((3-hydroxy-5-methyl-1-(4-methylpentyl)-2-oxoindolin-3-yl)methyl)-5-methoxyphenyl acetate: 1H NMR (CDCl3) δ 7.24 (dd, 1H), 7.15 (d, 1H), 7.04 (m, 1H), 6.82 (dd, 1H), 6.66 (m, 2H), 3.83 (s, 3H), 3.72 (m, 1H), 3.55 (m, 1H), 3.26 (d, 1H), 3.01 (d, 1H), 2.58 (t, 2H), 1.79 (m, 2H), 1.56 (BS, OH), 1.11 (t, 3H), 1.07 (t, 3H). Calculated mass for Chemical Formula: $C_{22}H_{24}ClNO_5$ 417.89, observed, 440.1 (ESI, M+Na).

Example 10

5-chloro-1-ethyl-3-(2-hydroxy-3-methoxybenzyl)-2-oxoindolin-3-yl dimethylcarbamate

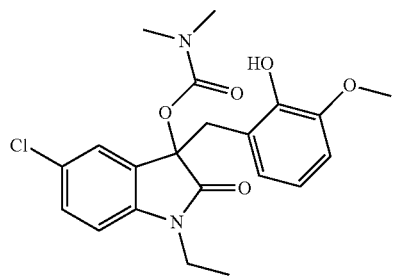 [SMILES: CCN1C(=O)C(Cc2cccc(OC)c2O)(OC(=O)N(C)C)c2cc(Cl)ccc21]

To a clean flask equipped with a stir bar was added 5-chloro-ethyl isatin (29.5 grams, 140 mmol). This was taken up in 500 mL of THF. A solution of NaBH4 (5.827 grams, 154 mmol, in 200 mL of H2O), was added. After 1 minute the reaction was quenched 2.0M HCl (approximately 500 mL). The solution was salted out. The organic layer was separated. The aqueous layer was washed two times with ethyl acetate. The combined organic material was dried with Na2SO4, filtered and concentrated. The crude material was then used in the next step without further purification.

To a flask charged with the reduced isatin (1.0 grams, 4.7 mmol), was added DMAP (0.057 grams, 0.47 mmol) and 23 mL of anhydrous dichloromethane. While stirring at room temperature, triethylamine (0.71 mL, 5.2 mmol) was added followed by N,N-dimethyl-chlorocarbamate (0.43 mL, 4.7 mmol). The solution stirred at room temperature overnight. The next day the solution was quenched with water and the two layers separated. The aqueous layer was washed with dichloromethane two times. The combined organic material was washed with brine, dried with Na2SO4, filtered, and concentrated. Purification using a Teledyne ISCO combiflash Rf on silica support (hexanes/ethyl acetate gradient) afforded the desired compound. (0.716 grams, 54% yield).

To a flame dried flask equipped with a stir bar, cooled under argon, was added the carbamate (0.5266 grams, 1.86 mmol, 0.5 M in anhydrous toluene). While stirring at room temperature, LiHMDS (2.4 mL, 2.4 mmol, 1.0 M in THF) was added. After ten minutes a solution of 3-methoxy-2-tert-butyl carbonate-1-benzylic alcohol (0.215 grams, 0.85 mmol, 0.5 M in THF) was added. Once the reaction was complete, the mixture was acidified using 1.0M HCl and the two layers were separated. The aqueous layer was then salted out and washed with Ethyl acetate. The aqueous layer was then washed with acetonitrile. The combined organic material was dried with Na2SO4, filtered and concentrated. Purification using a Teledyne ISCO combiflash Rf on silica support (hexanes/ethyl acetate gradient) followed by C18 support (water with 0.1% formic acid/acetonitrile gradient) to afford the desired compound. (0.155 grams, 44% yield). 1H NMR (CDCl3) δ 7.16 (dd, 1H), 6.84 (s, 1H), 6.71 (m, 3H), 6.62 (d, 1H), 5.51 (s, OH), 3.82 (s, 3H), 3.78 (m, 1H), 3.61 (m, 1H), 3.43 (d, 1H), 3.17 (d, 1H), 3.05 (s, 3H), 2.79 (s, 3H), 1.13 (s, 3H). Calculated mass for Chemical Formula: $C_{21}H_{23}ClN_2O_5$ 418.13, observed, 441.1. (ESI, M+Na).

Example 11

(1,3-dioxolan-4-yl)methyl (5-chloro-1-ethyl-3-(2-hydroxy-3-methoxybenzyl)-2-oxoindolin-3-yl) carbonate

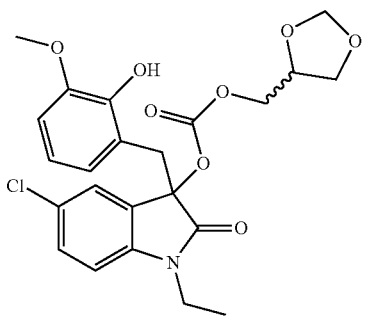 [SMILES: CCN1C(=O)C(Cc2cccc(OC)c2O)(OC(=O)OCC2COCO2)c2cc(Cl)ccc21]

This compound was prepared in a similar manner to 2-((5-chloro-1-ethyl-3-hydroxy-2-oxoindolin-3-yl)methyl)-6-methoxyphenyl morpholine-4-carboxylate: 1H NMR (CDCl3) δ 7.20 (dd, 1H), 7.04 (d, 1H), 6.69 (m, 3H), 6.60 (d, 1H), 5.48 (BS, 1H), 5.01 (s, 1H), 4.88 (d, 1H), 4.25 (m, 1H), 4.09 (m, 2H), 3.96 (m, 1H), 3.8 (m, 3H), 3.72 (m, 3H), 3.46 (d, 1H), 3.26 (d, 1H), 1.09 (t, 3H). Calculated mass for Chemical Formula: $C_{23}H_{24}ClNO_8$ 477.12, observed, 330.0 (ESI, M—carbonate+1).

Example 12

5-chloro-1-ethyl-3-(2-(((2-(2-hydroxyethoxy)ethyl)carbamoyl)oxy)-3-methoxybenzyl)-2-oxoindolin-3-yl benzoate

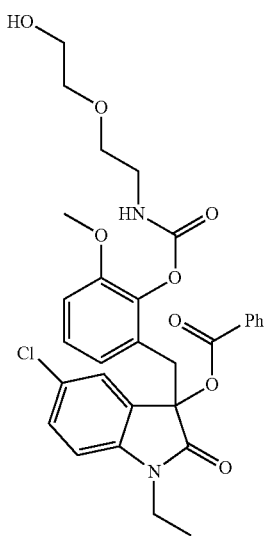 [SMILES: CCN1C(=O)C(Cc2cccc(OC)c2OC(=O)NCCOCCO)(OC(=O)c2ccccc2)c2cc(Cl)ccc21]

This compound was prepared in a similar manner to 2-((5-chloro-1-ethyl-3-hydroxy-2-oxoindolin-3-yl)methyl)-6-methoxyphenyl morpholine-4-carboxylate: 1H NMR (CDCl3) δ 8.05 (m, 2H), 7.58 (t, 1H), 7.45 (m, 2H), 7.22 (dd, 1H), 7.12 (d, 1H), 6.98 (t, 1H), 6.80 (d, 1H), 6.65 (m, 2H), 5.63 (bt, 1H), 3.82-3.46 (m, 12H), 3.46 (m 3H), 3.38 (d, 1H), 1.09 (t, 3H). Calculated mass for Chemical Formula: $C_{30}H_{31}ClN_2O_8$ 582.18, observed, 583.2. (ESI, M+Na).

Example 13

2-((5-chloro-1-ethyl-2-oxoindolin-3-yl)methyl)-6-methoxyphenyl dimethylcarbamate

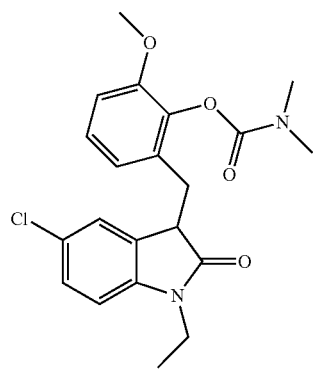 [SMILES: CCN1C(=O)C(Cc2cccc(OC)c2OC(=O)N(C)C)c2cc(Cl)ccc21]

To an oven dried flask equipped with a stir bar and an air to air condenser was added 5-chloro-oxindole (8.38 grams, 50.0 mmol), $K_2CO_3$ (7.6 grams, 55 mmol) and 500 mL of anhydrous acetonitrile. While stirring at room temperature ethyl bromide (4.8 mL, 65.0 mmol) was added.

The solution was heated to 100° C. and stirred for 72 hours. It was then cooled to room temperature, filtered, and concentrated. Purification using a Teledyne ISCO combiflash on silica support (hexanes/ethyl acetate gradient) to afford the desired compound. (3.1 grams, 32% yield).

To an oven dried flask equipped with a stir bar was added 5-chloro-N-ethyl-oxindole (0.75 grams, 3.83 mmol, 0.5 M in anhydrous toluene). While stirring at room temperature LiHMDS (4.2 mL, 4.2 mmol, 1.0 M in THF) was added. After stirring at room temperature for approximately ten minutes a solution of tert-butyl (2-(hydroxymethyl)-6-methoxyphenyl) carbonate (0.464 grams, 1.83 mmol, 0.5 M in anhydrous THF) was added. The reaction continued to stir until the starting material was consumed (monitored by LCMS). The reaction was then quenched using 1.0 M HCl, and the organic solution extracted using ethyl acetate. The aqueous layer was salted out, washed with ethyl acetate followed by acetonitrile. The combined organic material was dried with $Na_2SO_4$, filtered, and concentrated. Purification using a Teledyne ISCO combiflash on silica support (hexanes/ethyl acetate gradient) to afford the desired compound. (0.231 grams, 38% yield).

To a clean flask charged with the phenol (0.159 grams, 0.48 mmol) was added DMAP (0.001 grams), and 4.0 mL of anhydrous dichloromethane. While stirring at room temperature triethylamine (79 uL, 0.58 mmol) was added followed by N,N-dimethyl-chlorocarbamate (48 uL, 0.53 mmol). The reaction was monitored by LCMS. Once complete, the reaction was diluted with water and the organic material extracted. The aqueous layer was washed with chloromethane twice. The combined organic material was washed with brine, dried with $Na_2SO_4$, filtered and concentrated. Purification using a Teledyne ISCO combiflash on silica support (hexanes/ethyl acetate gradient) to afford the desired compound. (0.058 grams, 30% yield). 1H NMR (CDCl3) δ 7.30 (d, 1H), 7.24 (dd, 1H), 7.01 (d, 1H), 6.87 (d, 1H), 6.81 (m, 2H), 3.95 (s, 3H), 3.85 (dd, 2H), 3.77 (m, 1H), 3.63 (dd, 1H), 3.25 (s, 3H), 3.13 (s, 3H), 2.72 (dd, 1H), 1.34 (t, 3H). Calculated mass for Chemical Formula: $C_{21}H_{23}ClN_2O_4$, 402.1 observed 403.1 (ESI, M+1).

Example 14

3-hydroxy-1,5-dimethyl-3-((1-methyl-1H-indazol-4-yl)methyl)indolin-2-one

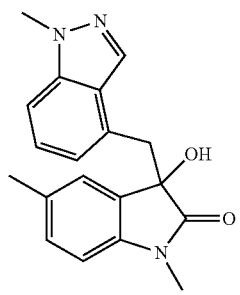 [SMILES: Cc1ccc2c(c1)C(O)(Cc1cccc3c1cnn3C)C(=O)N2C]

To a microwave vial that was stored in an oven at 150° C. equipped with a stir bar, cooled under argon, was added 5-methyl isatin (0.645 grams, 4.0 mmol) and $K_2CO_3$ (0.607 grams, 4.4 mmol). This was taken up in DMF (20.0 mL) and methyl iodide (0.27 mL, 4.4 mmol) was added. The solution was then heated in a Biotage microwave reactor at 100° C. on a setting of low. The solution was then concentrated, taken up in dichloromethane, filtered, and concentrated again. The intermediate was then used for the subsequent step without any further purification.

To a flask charged with N-methyl-5-methyl isatin (8.0 mmol) was added 60 mL of THF. In a separate flask $NaBH_4$ (0.341 grams, 8.80 mmol) was taken up in 20.0 mL of H2O. The $NaBH_4$ solution was then added to the isatin. After approximately 30 seconds, the reaction was quenched with saturated ammonium chloride. The organic material extracted using dichloromethane. The aqueous layer was washed with dichloromethane three times. The combined organic material was dried with $Na_2SO_4$, filtered and concentrated. The intermediate was then used for the subsequent step without any further purification.

To a flask charged with N-methyl-5-methyl-3hydroxy-oxindole (8.0 mmol) was added DMAP (0.097 grams, 0.8 mmol) followed by 80 mL of anhydrous dichloromethane. While stirring at room temperature, triethyl amine (1.70 mL, 12.0 mmol) was added followed by benzoyl chloride (0.97 mL, 8.40 mmol). The reaction continued to stir at room temperature. Once complete, the reaction was diluted with water and the organic material extracted. The aqueous layer was washed twice with dichloromethane. The combined organic material was washed with brine, dried with $Na_2SO_4$, filtered and concentrated. Purification using a Teledyne ISCO combiflash on silica support (hexanes/ethyl acetate gradient) to afford the desired compound. (1.215 grams, 54% yield).

To an oven dried flask equipped with a stir bar cooled under argon was added the benzoate (0.07 grams, 0.25 mmol, 0.5 M in toluene). While stirring at room temperature, LiHMDS (0.4 mL, 0.4 mmol, 1.0 M in THF) was added. After ten minutes a solution of 1H-Indazole, 4-(chloromethyl)-1-methyl (0.067 grams, 0.37 mmol, in 0.5 mL of DMF) was added. The reaction continued to stir at room temperature until its completion. The reaction was quenched with 1.0M HCl and the organic material extracted using ethyl acetate. The aqueous layer was salted out, washed with ethyl acetate, followed by acetonitrile. The combined organic material was then dried with $Na_2SO_4$, filtered, and concentrated. Purification using a Teledyne ISCO combiflash on silica support (hexanes/ethyl acetate gradient) followed by C18 support (water with 0.1% formic acid/acetonitrile gradient) to afford 0.003 grams of the desired compound. 1H NMR (CDCl3) δ 7.83 (BS, 1H), 7.22 (m, 2H), 7.00 (d, 1H), 6.89 (s, 1H), 6.80 (dd, 1H), 6.53 (d, 1H), 4.02 (s, 3H), 3.59 (d, 1H), 3.44 (d, 1H), 3.01 (s, 3H), 2.23 (s, 3H) 1.6 (BS, 1H). Calculated mass for Chemical Formula: $C_{19}H_{19}N_3O_2$ 321.15, observed, 322.2. (ESI, M+1). The major product, the benzoate was also isolated in this manner, 0.015 grams. Combined yield, 14%.

Example 15

1-butyl-3-((1-methyl-1H-indazol-4-yl)methyl)-2-oxoindolin-3-yl benzoate

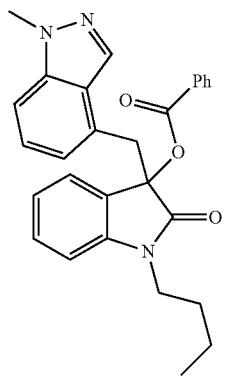 [SMILES: CCCCN1C(=O)C(Cc2cccc3c2cnn3C)(OC(=O)c2ccccc2)c2ccccc21]

This compound was prepared in a similar manner to 3-hydroxy-1,5-dimethyl-3-((1-methyl-1H-benzo[d]imidazol-4-yl)methyl)indolin-2-one. 1H NMR (CDCl3) δ 7.99 (m, 2H), 7.83 (BS, 1H), 7.56 (t, 1H), 7.43 (m, 2H), 7.22 (m, 3H), 6.95 (dd, 1H), 6.89 (t, 1H), 6.80 (d, 1H), 6.69 (d, 1H), 4.04 (s, 3H), 3.87 (d, 1H), 3.64 (m, 1H), 3.59 (d, 1H), 3.45 (m, 1H), 1.32 (m, 2H), 1.17 (m, 2H), 0.86 (t, 3H). Calculated mass for Chemical Formula: $C_{28}H_{27}N_3O_3$ 453.21, observed, 454.2. (ESI, M+1).

Example 16

3-(benzo[d][1,3]dioxol-4-ylmethyl)-5-chloro-2-oxo-1-propylindolin-3-yl benzoate

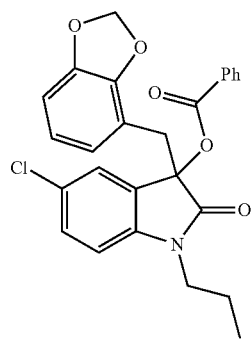 [SMILES: CCCN1C(=O)C(Cc2cccc3c2OCO3)(OC(=O)c2ccccc2)c2cc(Cl)ccc21]

To an oven dried flask cooled under argon equipped with a stir bar was added 5-chloro-2-oxo-1-propylindolin-3-yl benzoate (0.065 grams, 0.2 mmol, 0.5 M in toluene). While stirring at room temperature LiHMDS (0.3 mL, 0.3 mmol, 1.0 M in THF) was added. After stirring at room temperature for ten minutes, a solution of 1,3-Benzodioxole, 4-(chloromethyl) (0.05 grams, 0.3 mmol, in 0.45 mL anhydrous DMF) was added. The reaction continued to stir until the starting material was consumed. The reaction was then quenched with 1.0 M HCl, and extracted with ethyl acetate. The aqueous layer was salted out, and washed with ethyl acetate, followed by acetonitrile. The combined organic material was then dried with $Na_2SO_4$, filtered and concentrated. Purification using a Teledyne ISCO combiflash on silica support (hexanes/ethyl acetate gradient) followed by C18 support (water with 0.1% formic acid/acetonitrile gradient) to afford 0.032 grams of the desired compound. (33% yield). 1H NMR (CDCl3) δ 8.05 (m, 2H), 7.59 (dd, 1H), 7.46 (m, 2H), 7.22 (dd, 1H), 7.03 (d, 1H), 6.70 (m, 4H), 5.81 (d, 1H), 5.63 (d, 1H), 3.69-354 (m, 3H), 3.20 (d, 1H), 1.63 (m, 2H), 0.93 (t, 3H). Calculated mass for Chemical Formula: $C_{26}H_{22}ClNO_5$ 463.91, observed, 342.1 (ESI, M−OBz).

Example 17

3-(benzo[d][1,3]dioxol-4-ylmethyl)-1-ethyl-3-hydroxy-5-methylindolin-2-one

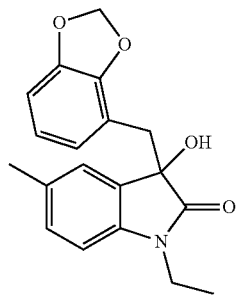 [SMILES: CCN1C(=O)C(O)(Cc2cccc3c2OCO3)c2cc(C)ccc21]

To an oven dried flask cooled under argon equipped with a stir bar was added 5-methyl-2-oxo-1-ethylindolin-3-yl benzoate (0.05 grams, 0.17 mmol, 0.5 M in toluene). While stirring at room temperature LiHMDS (0.3 mL, 0.3 mmol, 1.0 M in THF) was added. After stirring at room temperature for ten minutes, a solution of 1,3-Benzodioxole, 4-(chloromethyl) (0.043 grams, 0.25 mmol, in 0.3 mL anhydrous DMF) was added. The reaction continued to stir until the starting material was consumed. The reaction was then quenched with 1.0 M HCl, and extracted with ethyl acetate. The aqueous layer was salted out, and washed with ethyl acetate, followed by acetonitrile. The combined organic material was then dried with $Na_2SO_4$, filtered and concentrated. Purification was done using a Teledyne ISCO combiflash on silica support (hexanes/ethyl acetate gradient). (0.044 grams collected, 60% yield)

To a clean flask charged with the benzoate (0.044 grams, 0.1 mmol) was added 0.5 mL methanol and 0.5 mL water. KOH (0.21 mL, 0.4 mmol, 2.0 M in water) was added and the mixture was then heated using a Biotage microwave reactor on a setting of Low to 140° C. for one hour. The solution was then acidified using glacial acetic acid and the solvent removed. Purification using a Teledyne ISCO combiflash on C18 support (water with 0.1% formic acid/acetonitrile gradient) to afford 0.016 grams of the desired compound. 1H NMR (CDCl3) δ 7.05 (m, 2H), 6.61 (m, 2H), 6.60 (d, 1H), 6.52 (m, 1H), 5.82 (d, 1H), 5.61 (d, 1H), 3.72 (m, 1H), 3.53 (m, 1H), 3.35 (d, 1H), 3.05 (d, 1H), 2.30 (s, 3H), 1.6 (BS, 1H), 1.09 (t, 3H). Calculated mass for Chemical Formula: $C_{19}H_{19}NO_4$ 325.36, observed, 326.1. (ESI, M+1).

Example 18

3-(benzo[d][1,3]dioxol-4-ylmethyl)-1-butyl-3-hydroxyindolin-2-one

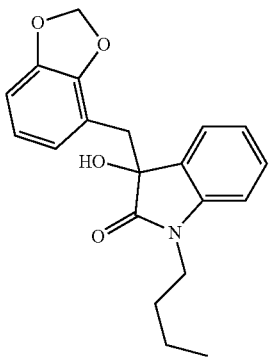 [SMILES: CCCCN1C(=O)C(O)(Cc2cccc3c2OCO3)c2ccccc21]

This compound was made in a similar manner to 3-(benzo[d][1,3]dioxol-4-ylmethyl)-1-ethyl-3-hydroxy-5-methylindolin-2-one. 1H NMR (CDCl3) δ 7.24 (m, 2H), 7.01 (t, 1H), 6.71 (d, 1H), 6.65 (m, 2H), 6.51 (m, 1H), 5.81 (d, 1H), 5.63 (d, 1H), 3.70 (m, 1H), 3.46 (m, 1H), 3.37 (d, 1H), 3.04 (d, 1H), 2.9 (BS, 1H), 1.5 (m, 2H), 1.26 (m, 2H), 0.91 (t, 3H). Calculated mass for Chemical Formula: $C_{20}H_{21}NO_4$ 339.15, observed, 363.2 (ESI, M+Na+1).

Example 19

3-(benzo[d][1,3]dioxol-4-ylmethyl)-3-hydroxy-1-isobutylindolin-2-one

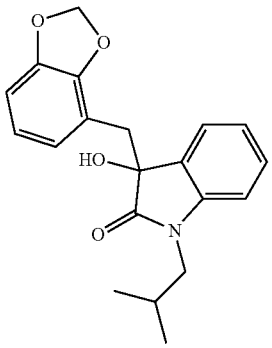 [SMILES: CC(C)CN1C(=O)C(O)(Cc2cccc3c2OCO3)c2ccccc21]

This compound was made in a similar manner to 3-(benzo[d][1,3]dioxol-4-ylmethyl)-1-ethyl-3-hydroxy-5-methylindolin-2-one. 1H NMR (CDCl3) δ 7.23 (m, 2H), 7.02 (t, 1H), 6.73 (d, 1H), 6.66 (m, 2H), 6.53 (m, 1H), 5.82 (s, 1H), 5.66 (s, 1H), 3.53 (dd, 1H), 3.37 (d, 1H), 3.27 (dd, 1H), 3.06 (d, 1H), 2.96 (BS, 1H), 2.03 (m, 1H), 0.85 (dd, 6H). Calculated mass for Chemical Formula: $C_{20}H_{21}NO_4$ 339.15, observed, 340.1. (ESI, M+1).

Example 20

3-(benzo[d][1,3]dioxol-4-ylmethyl)-1-isopentyl-2-oxoindolin-3-yl benzoate

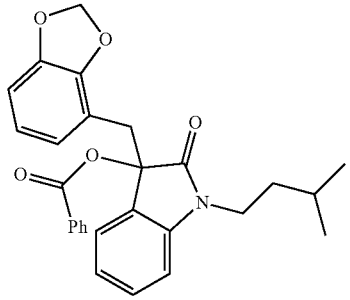 [SMILES: CC(C)CCN1C(=O)C(Cc2cccc3c2OCO3)(OC(=O)c2ccccc2)c2ccccc21]

This compound was made in a similar manner to 3-(benzo[d][1,3]dioxol-4-ylmethyl)-5-chloro-2-oxo-1-propylindolin-3-yl benzoate. 1H NMR (CDCl3) δ 8.05 (m, 2H), 7.59 (dd, 1H), 7.46 (m, 2H), 7.22 (m, 1H), 7.01 (dd, 1H), 6.92 (dd, 1H), 6.76-6.66 (m, 4H), 5.77 (d, 1H), 5.61 (d, 1H), 3.75 (m, 1H) 3.63 (m, 1H), 3.58 (d, 1H), 2.21 (d, 1H), 1.62 (m, 1H)1.46 (m, 2H), 0.98 (dd, 6H). Calculated mass for Chemical Formula: $C_{28}H_{27}NO_5$ 457.19, observed, 377.2. (ESI, M−OBz+H2O).

Example 21

3-(benzo[d][1,3]dioxol-4-ylmethyl)-1-isobutyl-5-methyl-2-oxoindolin-3-yl benzoate

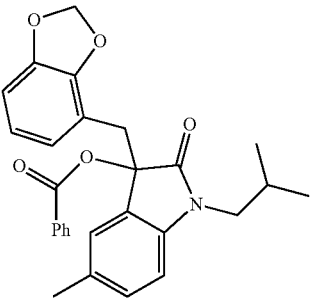 [SMILES: Cc1ccc2c(c1)C(Cc1cccc3c1OCO3)(OC(=O)c1ccccc1)C(=O)N2CC(C)C]

This compound was made in a similar manner to 3-(benzo[d][1,3]dioxol-4-ylmethyl)-5-chloro-2-oxo-1-propylindolin-3-yl benzoate. 1H NMR (CDCl3) δ 8.05 (m, 2H), 7.59 (dd, 1H), 7.46 (m, 2H), 7.04 (dd, 1H), 6.80 (s, 1H), 6.70 (m, 4H), 5.76 (d, 1H), 5.64 (d, 1H), 3.57 (d, 1H), 3.52 (dd, 1H), 3.40 (dd, 1H), 3.19 (d, 1H), 2.22 (s, 3H), 2.13 (m, 1H), 0.93 (dd, 6H). Calculated mass for Chemical Formula: $C_{28}H_{27}NO_5$ 457.19, observed, 377.3 (ESI, M−OBz+H2O).

Example 22

3-(benzo[d][1,3]dioxol-4-ylmethyl)-1-isopentyl-5-methyl-2-oxoindolin-3-yl benzoate

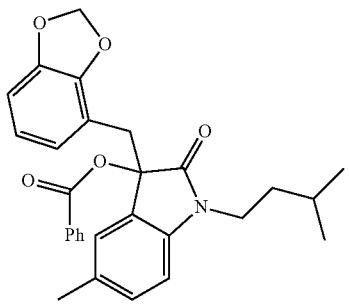 [SMILES: Cc1ccc2c(c1)C(Cc1cccc3c1OCO3)(OC(=O)c1ccccc1)C(=O)N2CCC(C)C]

This compound was made in a similar manner to 3-(benzo[d][1,3]dioxol-4-ylmethyl)-5-chloro-2-oxo-1-propylindolin-3-yl benzoate. 1H NMR (CDCl3) δ 8.05 (m, 2H), 7.59 (dd, 1H), 7.46 (m, 2H), 7.05 (d, 1H), 6.82 (s, 1H), 6.72-6.63 (m, 4H), 5.79 (d, 1H), 5.62 (d, 1H), 3.70 (m, 1H), 3.60 (m, 1H), 3.57 (d, 1H), 3.20 (d, 1H), 2.23 (s, 3H), 1.63 (m, 1H), 1.46 (m, 2H), 0.97 (dd, 6H). Calculated mass for Chemical Formula: $C_{29}H_{29}NO_5$ 471.20, observed, 391.2. (ESI, M−OBz+H2O).

Example 23

3-((1H-benzo[d]imidazol-4-yl)methyl)-5-chloro-1-ethyl-3-hydroxyindolin-2-one

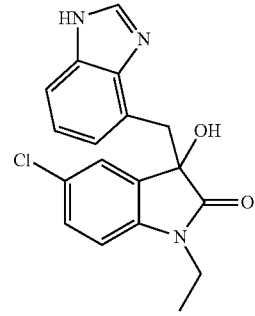 [SMILES: CCN1C(=O)C(O)(Cc2cccc3[nH]cnc23)c2cc(Cl)ccc21]

This was made in a similar method to 3-(benzo[d][1,3]dioxol-4-ylmethyl)-1-ethyl-3-hydroxy-5-methylindolin-2-one using 1H-Benzimidazole, 7-(chloromethyl) 1H NMR (CD3OD) δ 8.33 (BS, 1H), 7.48 (d, 1H), 7.18 (m, 2H), 7.10 (dd, 1H), 6.82 (d, 1H), 6.72 (d, 1H), 3.67 (d, 1H), 3.61 (m, 1H), 3.50-3.42 (m, 2H), 0.85 (t, 3H). Calculated mass for Chemical Formula: $C_{18}H_{16}ClN_3O_2$ 341.09, observed, 342.1. (ESI, M+1).

Example 24

1-ethyl-3-(2-hydroxy-3,4-dimethoxybenzyl)-5-methyl-2-oxoindolin-3-yl dimethylcarbamate

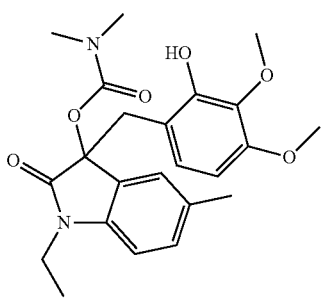 [SMILES: CCN1C(=O)C(Cc2ccc(OC)c(OC)c2O)(OC(=O)N(C)C)c2cc(C)ccc21]

To a flask charged with 1-ethyl-3-hydroxy-3-(2-hydroxy-3,4-dimethoxybenzyl)-5-methylindolin-2-one (0.05 grams, 0.14 mmol), was added DMAP (0.002 grams, 0.014 mmol) and 1.4 mL dichloromethane. Triethylamine (0.038 mL, 0.28 mmol) was added followed by dimethylcarbamoyl chloride (0.020 mL, 0.2 mmol). The reaction stirred at room temperature. After 3 hours, the reaction was diluted with methanol, and concentrated. Purification using a Teledyne ISCO combiflash Rf on silica support (hexanes/ethyl acetate gradient) followed by C18 support (water with 0.1% formic acid/acetonitrile gradient) to afford the desired compound. 0.018 grams, 30% yield. 1H-NMR (CDCl3) δ 6.99 (d, 1H), 6.72 (m, 2H), 6.59 (d, 1H), 6.33 (d, 1H), 5.65 (s, 1H), 3.84-3.63 (m, 7H), 3.61 (m, 1H), 3.34 (d, 1H), 3.11 (d, 1H), 3.04 (s, 3H), 2.79 (s, 3H), 2.23 (s, 3H), 1.13 (t, 3H). Calculated mass for Chemical Formula: $C_{23}H_{28}N_2O_6$, 428.19, observed 340.1 (M-Me2NCOO, ESI)

Example 25

3-((1-benzoyl-1H-indol-3-yl)methyl)-2-oxo-1-propylindolin-3-yl dimethylcarbamate

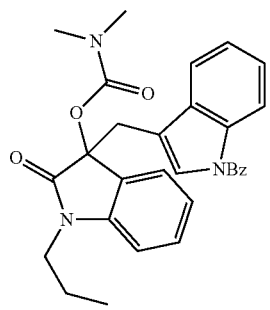

To an oven dried flask that was cooled under argon was added 2-oxo-1-propylindolin-3-yl dimethylcarbamate (0.052 grams, 0.2 mmol, in 0.4 mL toluene). LiHMDS (0.3 mL, 1.0M) was added. After ten minutes of stirring at room temperature, a solution of (1-benzoyl-1H-indol-3-yl)methyl benzoate (0.92 grams, 0.26 mmol) in 0.3 mL DMF was added. The reaction was monitored by LCMS. Once all of the starting material was consumed, the reaction was quenched with 1.0M HCl, salted out and extracted using ethyl acetate. The aqueous solution was then washed with ethyl acetate twice. The combined organic material was dried with $Na_2SO_4$, filtered and concentrated. Purification using a Teledyne ISCO combiflash Rf on silica support (hexanes/ethyl acetate gradient) followed by C18 support (water with 0.1% formic acid/acetonitrile gradient) to afford the desired compound. (0.029 grams, 30% yield). 1H-NMR (CDCl3) δ 8.34 (d, 1H), 7.60-7.46 (m, 6H), 7.35-7.24 (3H), 7.11 (d, 1H), 6.97 (dd, 1H), 6.69 (d, 1H), 6.66 (s, 1H), 3.59 (m, 1H) 3.40 (dd, 2H), 3.30 (m, 1H), 2.94 (s, 3H), 2.78 (s, 3H), 1.20 (m, 2H), 0.65 (t, 3H). Calculated mass for Chemical Formula: $C_{30}H_{29}N_3O_4$, 495.22, observed, 518.1 (M+Na, ESI).

Example 26

3-((1H-benzo[d]imidazol-4-yl)methyl)-5-chloro-1-methyl-2-oxoindolin-3-yl dimethylcarbamate

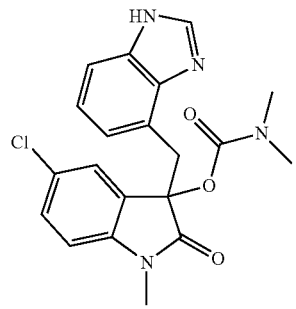 [SMILES: CN(C)C(=O)OC1(Cc2cccc3[nH]cnc23)C(=O)N(C)c2ccc(Cl)cc21]

This compound was made in a similar manner to 3-((1-benzoyl-1H-indol-3-yl)methyl)-2-oxo-1-propylindolin-3-yl dimethylcarbamate using 5-chloro-1-methyl-2-oxoindolin-3-yl dimethylcarbamate and the known 4-(chloromethyl)-1H-benzo[d]imidazole. (20% yield). 1H-NMR (CD3OD) δ 8.05 (s, 1H), 7.49 (d, 1H), 7.15 (m, 2H), 7.04 (d, 1H), 6.73 (dd, 1H), 6.66 (d, 1H), 3.75 (d, 1H), 3.43 (d, 1H), 3.08 (s, 3H), 3.01 (s, 3H), 2.75 (s, 3H). Calculated mass for $C_{20}H_{19}ClN_4O_3$, 398.11, observed 399.1 (M+1, MM API/ESI).

Example 27

5-chloro-1-ethyl-3-(pyrimidin-4-ylmethyl)indolin-2-one

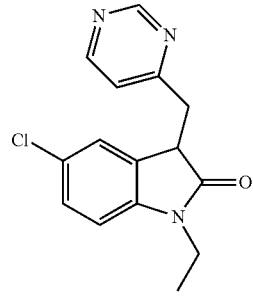 [SMILES: CCN1C(=O)C(Cc2ccncn2)c2cc(Cl)ccc21]

To a biotage microwave vial that was stored in the oven at 150° C. and cooled under argon was added 5-chloro-N-ethyl-oxindole (0.1258 grams, 0.6 mmol, 0.3M in 1,4 doxane). 4-methylpyrimidine (164 uL, 1.8 mmol) was added followed by 16 uL of trifluoromethansulfonic acid. The vessel was then sealed, and heated at 120° C. using a Biotage initiator for 12 hours. The solvent was then removed. Purification using a Teledyne ISCO combiflash Rf on silica support (hexanes/ethyl acetate gradient) followed by C18 support (water with 0.1% formic acid/acetonitrile gradient) to afford the desired compound. (0.034 grams, 20% yield). 1H-NMR (CDCl3) δ 9.10 (s, 1H), 8.63 (d, 1H), 7.22 (m, 2H), 6.99 (d, 1H), 6.75 (d, 1H), 4.06 (d, 1H), 3.84-3.69 (m, 2H) 3.50 (dd, 1H), 3.29 (dd, 1H), 1.25 (t, 3H). Calculated mass for Chemical Formula: $C_{15}H_{14}ClN_3O$, 287.08. observed 288.1 (M+1, MM API/ESI).

Example 28

5-methyl-1-ethyl-3-(pyrimidin-4-ylmethylene)indolin-2-one

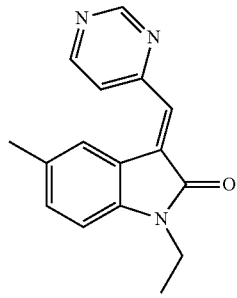 [SMILES: CCN1C(=O)/C(=C/c2ccncn2)c2cc(C)ccc21]

This compound was made in a similar manner to 5-chloro-1-ethyl-3-(pyrimidin-4-ylmethyl)indolin-2-one. Yield, 20% 1H-NMR (CDCl3) δ 9.46 (s, 1H), 8.86 (d, 1H), 8.78 (s, 1H), 7.54 (m, 2H), 7.17 (d, 1H), 6.75 (d, 1H), 3.82 (q, 2H), 2.38 (s, 3H), 1.29 (s, 3H). Calculated mass for Chemical Formula: $C_{16}H_{15}N_3O$, 265.12, observed 266.2 (M+1, API).

Example 29

5-chloro-1-ethyl-3-hydroxy-3-(pyrazin-2-ylmethyl)indolin-2-one

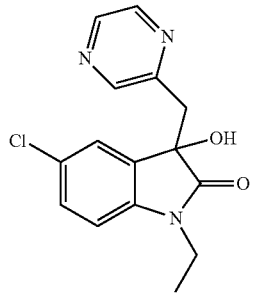 [SMILES: CCN1C(=O)C(O)(Cc2cnccn2)c2cc(Cl)ccc21]

This compound was made in a similar manner to 5-chloro-1-ethyl-3-(pyrimidin-4-ylmethyl)indolin-2-one using 5-chloro-1-ethylindoline-2,3-dione and 2-methylpyrazine. (yield, 25%). 1H-NMR (CDCl3) δ 8.49 (dd, 2H), 8.40 (s, 1H), 7.25 (dd, 1H), 7.06 (d, 1H), 6.72 (d, 1H), 3.66 (m, 2H) 3.30 (dd, 2H), 2.0 (bs, OH), 1.19 (t, 3H). Calculated mass for Chemical Formula: $C_{15}H_{14}ClN_3O_2$ 303.08 observed 304.1 (M+1, MM API/ESI).

Example 30

1-ethyl-5-methyl-3-(pyrazin-2-ylmethylene)indolin-2-one

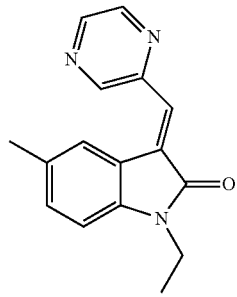 [SMILES: CCN1C(=O)/C(=C/c2cnccn2)c2cc(C)ccc21]

This compound was made in a similar manner to 5-chloro-1-ethyl-3-(pyrimidin-4-ylmethyl)indolin-2-one using 5-chloro-1-ethylindoline-2,3-dione and 2-methylpyrazine. (yield, 10%). 1H-NMR (CDCl3) δ 8.87 (s, 1H), 8.83 (s, 1H), 8.70 (s, 1H), 8.57 (d, 1H), 7.71 (s, 1H), 7.16 (d, 1H), 6.75 (d, 1H) 3.83 (q, 2H), 2.34 (s, 3H), 1.30 (t, 3H). Calculated mass for Chemical Formula: $C_{16}H_{15}N_3O$, 265.12, observed 266.2 (M+1, ESI).

Example 31

1-propyl-3-(pyridazin-3-ylmethylene)indolin-2-one

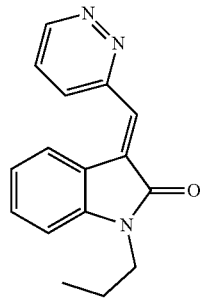 [SMILES: CCCN1C(=O)/C(=C/c2cccnn2)c2ccccc21]

This compound was made in a similar manner to 5-chloro-1-ethyl-3-(pyrimidin-4-ylmethyl)indolin-2-one using 1-propylindoline-2,3-dione and 3-methylpyridazine. (yield, 7%). 1H-NMR (CDCl3) δ 9.22 (m, 1H), 8.97 (t, 1H), 7.75 (m, 2H), 7.63 (m, 2H), 7.34 (dd, 1H), 7.71 (dd, 1H), 6.85 (dd, 1H) 3.78 (t, 2H), 1.77 (m, 2H), 1.02 (t, 3H). Chemical Formula: $C_{16}H_{15}N_3O$ 265.12, observed 266.1 (M+1, ESI).

Example 32

1-propyl-3-(pyridazin-3-ylmethyl)indolin-2-one

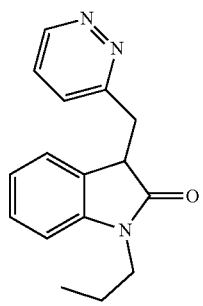 [SMILES: CCCN1C(=O)C(Cc2cccnn2)c2ccccc21]

This compound was made in a similar manner to 5-chloro-1-ethyl-3-(pyrimidin-4-ylmethyl)indolin-2-one using 1-propylindoline-2,3-dione and 3-methylpyridazine. Yield, 15%. 1H-NMR (CDCl3) δ 9.09 (d, 1H), 7.41 (m, 2H), 7.22 (dd, 1H), 7.01 (dd, 1H), 6.94 (dd, 1H), 6.80 (d, 1H), 4.14 (t, 1H), 3.67 (m, 3H), 3.47 (dd, 1H), 1.70 (m, 2H), 1.0 (t, 3H). Calculated mass for Chemical Formula: $C_{16}H_{17}N_3O$, 267.14, observed 268.1 (M+1, MM API/ESI).

Example 33

1,5-dimethyl-3-(pyridazin-3-ylmethyl)indolin-2-one

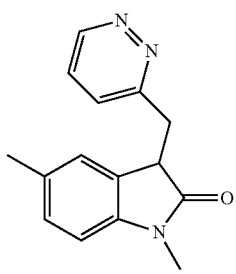 [SMILES: Cc1ccc2c(c1)C(Cc1cccnn1)C(=O)N2C]

This compound was made in a similar manner to 5-chloro-1-ethyl-3-(pyrimidin-4-ylmethyl)indolin-2-one using 5-methyl-1-methylindoline-2,3-dione and 3-methylpyridazine. Yield, 5%. 1H-NMR (CDCl3) δ 9.12, (s, 1H), 7.47 (s, 2H), 7.05 (d, 1H), 6.88 (s, 1H), 6.69 (d, 1H), 4.14 (t, 1H), 3.65 (dd, 1H), 3.47 (m, 1H), 3.20 (s, 3H), 2.26 (s, 3H). Calculated mass for Chemical Formula: $C_{15}H_{15}N_3O$ Exact Mass: 253.12, observed 254.2 (M+1, ESI).

Example 34

N-(5-chloro-2-oxo-1-propyl-3-(pyridazin-3-ylmethyl)indolin-3-yl)nicotinamide

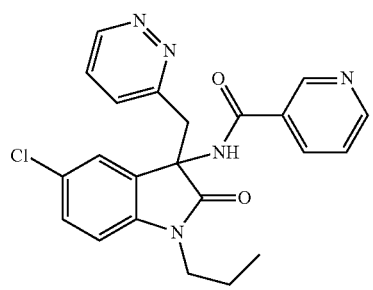 [SMILES: CCCN1C(=O)C(Cc2cccnn2)(NC(=O)c2cccnc2)c2cc(Cl)ccc21]

This compound was made in a similar manner to 5-chloro-1-ethyl-3-(pyrimidin-4-ylmethyl)indolin-2-one using N-(5-chloro-2-oxo-1-propylindolin-3-ylidene)nicotinamide and 3-methylpyridazine. Yield, 5%. 1H-NMR (CDCl3) δ 9.5 (s, 1H), 9.25 (dd, 1H), 8.14 (d, 1H), 8.74 (dd, 1H), 8.17 (dt, 1H), 7.53 (dd, 1H), 7.41 (dd, 1H), 7.28-7.23 (m, 2H), 6.88 (d, 1H), 6.57 (d, 1H), 3.79 (t, 2H), 3.58 (d, 1H), 1.16 (d, 1H), 1.83 (m, 2H), 1.04 (t, 3H). Calculated mass for Chemical Formula: $C_{22}H_{20}ClN_5O_2$, 421.13, observed 422.1 (M+1, API).

Example 35

1-methyl-3-(pyridazin-3-ylmethylene)indolin-2-one

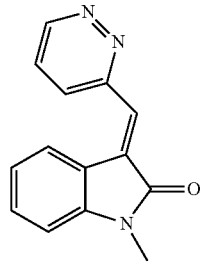 [SMILES: CN1C(=O)/C(=C/c2cccnn2)c2ccccc21]

This compound was made in a similar manner to 5-chloro-1-ethyl-3-(pyrimidin-4-ylmethyl)indolin-2-one using 1-methylindoline-2,3-dione and 3-methylpyridazine. Yield, 5%. 1H-NMR (CDCl3) δ 9.21 (dd, 1H), 8.97 (d, 1H), 7.72 (dd, 1H), 7.70 (s, 1H), 7.60 (dd, 1H), 7.37 (dd, 1H), 7.11 (dd, 1H), 6.85 (d, 1H), 3.31 (s, 3H). Calculated mass for Chemical Formula: $C_{14}H_{11}N_3O$, 237.09, observed 238.1 (M+1, API).

Example 36

3-((1H-benzo[d]imidazol-2-yl)methylene)-5-chloro-1-ethylindolin-2-one

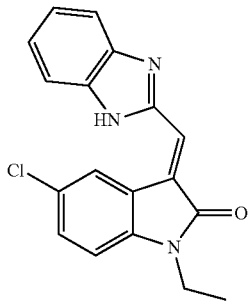 [SMILES: CCN1C(=O)/C(=C/c2nc3ccccc3[nH]2)c2cc(Cl)ccc21]

This compound was made in a similar manner to 5-chloro-1-ethyl-3-(pyrimidin-4-ylmethyl)indolin-2-one using 5-chloro-1-ethylindoline-2,3-dione and 2-methylbenzimidazole. Yield, 20%. 1H-NMR (CDCl3) δ 7.81 (m, 2H), 7.58 (d, 2H), 7.34 (m, 4H), 6.86 (d, 1H), 3.92 (q, 2H), 1.37 (t, 3H). Calculated mass for Chemical Formula: $C_{18}H_{14}ClN_3O$, 323.08, observed 324.1 (M+1, ESI).

Example 37

5-chloro-3-hydroxy-1-propyl-3-(pyrazin-2-ylmethyl)indolin-2-one

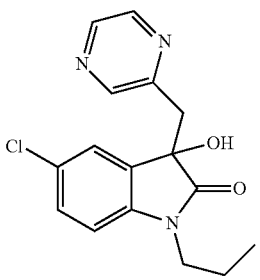 [SMILES: CCCN1C(=O)C(O)(Cc2cnccn2)c2cc(Cl)ccc21]

This compound was made in a similar manner to 5-chloro-1-ethyl-3-(pyrimidin-4-ylmethyl)indolin-2-one using 5-chloro-1-propylindoline-2,3-dione and 2-methylpyrazine. Yield, 50%. 1H-NMR (CD3OD) δ 8.38 (m, 3H), 7.24 (m, 2H), 6.83 (d, 1H), 3.60 (m, 1H), 3.50 (m, 3H), 1.56 (m, 2H), 0.87 (t, 3H). Calculated mass for Chemical Formula: $C_{16}H_{16}ClN_3O_2$, 317.09, observed 318.1 (M+1, MM API/ESI).

Example 38

5-chloro-3-hydroxy-1-methyl-3-(pyridin-4-ylmethyl)indolin-2-one

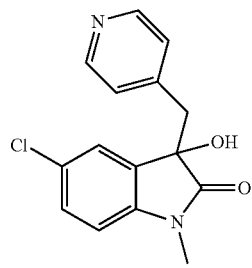 [SMILES: CN1C(=O)C(O)(Cc2ccncc2)c2cc(Cl)ccc21]

This compound was made in a similar manner to 5-chloro-1-ethyl-3-(pyrimidin-4-ylmethyl)indolin-2-one using 5-chloro-1-methylindoline-2,3-dione and 4-methylpyridine. Yield, 70%. 1H-NMR (CD3OD) δ 8.28 (d, 2H), 7.28 (dd, 1H), 7.25 (d, 1H), 7.05 (d, 2H), 6.79 (d, 1H), 3.30 (d, 1H), 3.21 (d, 1H), 3.00 (s, 3H). Calculated mass for Chemical Formula: $C_{15}H_{13}ClN_2O_2$ 288.07, observed 289.1 (M+1, MM API/ESI).

Example 39

5-chloro-3-hydroxy-1-propyl-3-(pyridazin-4-ylmethyl)indolin-2-one

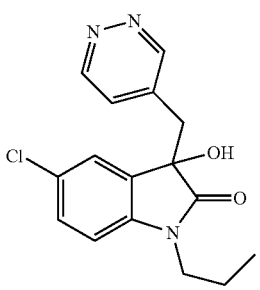 [SMILES: CCCN1C(=O)C(O)(Cc2ccnnc2)c2cc(Cl)ccc21]

This compound was made in a similar manner to 5-chloro-1-ethyl-3-(pyrimidin-4-ylmethyl)indolin-2-one using 5-chloro-1-propylindoline-2,3-dione and 4-methylpyridazine. Yield, 20%. 1H-NMR (CD3OD) δ 8.96 (dd, 1H), 8.81 (dd, 1H), 7.34 (m, 3H), 6.88 (dd, 1H), 3.55 (m, 1H), 3.46 (m, 1H), 3.31 (d, 1H), 3.23 (d, 1H), 1.45 (m, 2H), 0.79 (t, 3H). Calculated mass for Chemical Formula: $C_{16}H_{16}ClN_3O_2$, 317.09, observed 318.1 (M+1, MM API/ESI).

Example 40

3-hydroxy-1-methyl-3-(pyridin-4-ylmethyl)indolin-2-one

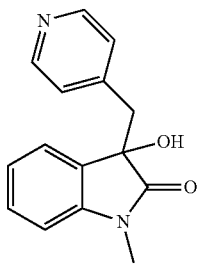 [SMILES: CN1C(=O)C(O)(Cc2ccncc2)c2ccccc21]

This compound was made in a similar manner to 5-chloro-1-ethyl-3-(pyrimidin-4-ylmethyl)indolin-2-one using 1-methylindoline-2,3-dione and 4-methylpyridine. Yield, 40%. 1H-NMR (CD3OD) δ 8.26 (d, 2H), 7.28 (m, 2H), 7.08 (m, 3H), 6.81 (d, 1H), 3.31 (d, 1H), 3.21 (d, 1H), 3.00 (s, 3H). Calculated mass for Chemical Formula: $C_{15}H_{14}N_2O_2$, 254.11, observed 255.1 (M+1, MM API/ESI).

Example 41

(E)-3-((1H-benzo[d]imidazol-2-yl)methylene)-5-chloro-1-methylindolin-2-one

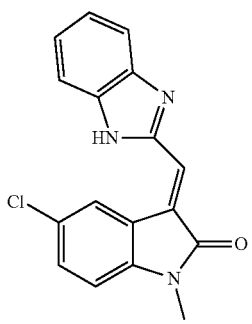 [SMILES: CN1C(=O)/C(=C/c2nc3ccccc3[nH]2)c2cc(Cl)ccc21]

This compound was made in a similar manner to 5-chloro-1-ethyl-3-(pyrimidin-4-ylmethyl)indolin-2-one 5-chloro-1-methylindoline-2,3-dione and 2-methylbenzimidazole. Yield, 20%. 1H-NMR (CD3OD) δ 8.99 (s, 1H), 8.73 (d, 1H), 8.25 (d, 1H), 7.56 (m, 2H), 7.23 (dd, 1H), 7.05 (d, 1H), 6.81 (d, 1H), 3.34 (s, 3H). Calculated mass for Chemical Formula: $C_{17}H_{12}ClN_3O$ 309.07, observed 310.1 (M+1, MM API/ESI).

Example 42

N-(3-((1H-benzo[d]imidazol-2-yl)methyl)-1-methyl-2-oxoindolin-3-yl)nicotinamide

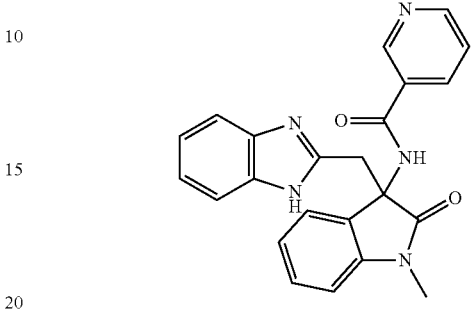

This compound was made in a similar manner to 5-chloro-1-ethyl-3-(pyrimidin-4-ylmethyl)indolin-2-one using N-(1-methyl-2-oxoindolin-3-ylidene)nicotinamide and 2-methylbenzimidazole. Yield, 20%. 1H-NMR (CD3OD) δ 9.05 (s, 1H), 8.71 (t, 1H), 8.28 (dd, 1H), 7.58-7.51 (m, 4H), 7.29-7.25 (m, 3H), 7.02-6.97 (m, 2H), 6.88 (d, 1H), 3.67 (d, 1H), 3.49 (d, 1H), 3.20 (s, 3H). Calculated mass for Chemical Formula: $C_{23}H_{19}N_5O_2$ 397.15, observed 398.1 (M+1, ESI).

Example 43

1-ethyl-3-hydroxy-3-(pyridazin-3-ylmethyl)indolin-2-one

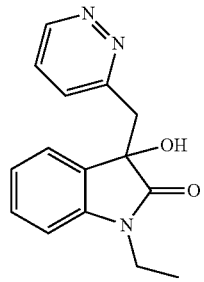 [SMILES: CCN1C(=O)C(O)(Cc2cccnn2)c2ccccc21]

This compound was made in a similar manner to 5-chloro-1-ethyl-3-(pyrimidin-4-ylmethyl)indolin-2-one using 1-ethylindoline-2,3-dione and 3-methylpyridazine. Yield, 22%. 1H-NMR (CD3OD) δ 8.94 (t, 1H), 7.50 (m, 2H), 7.24 (dd, 1H), 7.14 (dd, 1H), 7.02 (dd, 1H), 6.85 (d, 1H), 3.75-3.59 (m, 2H), 3.56 (dd, 2H), 1.10 (t, 3H). Calculated mass for Chemical Formula: $C_{15}H_{15}N_3O_2$ 269.12, observed 279.2 (M+1, MM API/ESI).

Example 44

1-ethyl-5-methyl-3,3-bis(pyridazin-4-ylmethyl)indolin-2-one

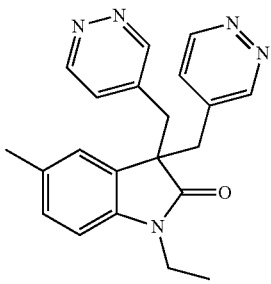 [SMILES: CCN1C(=O)C(Cc2ccnnc2)(Cc2ccnnc2)c2cc(C)ccc21]

This compound was made in a similar manner to 5-chloro-1-ethyl-3-(pyrimidin-4-ylmethyl)indolin-2-one using 5-methyl-1-ethylindoline-2,3-dione and 4-methylpyridazine. Yield, 40%. 1H-NMR (CDCl3) δ bs (9.0, 4H), 7.42 (s, 2H), 7.18 (bs, 1H), 7.02 (d, 1H), 6.35 (d, 1H), 3.38 (d, 2H) 3.29 (d, 2H), 3.14 (d, 2H), 2.43 (s, 3H), 0.62 (t, 3H). Calculated mass for Chemical Formula: $C_{21}H_{21}N_5O$ 359.17, observed 360.1 (M+1, MM API/ESI).

Example 45

1-propyl-3,3-bis(pyridazin-4-ylmethyl)indolin-2-one

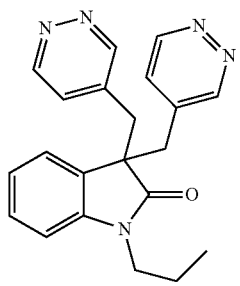 [SMILES: CCCN1C(=O)C(Cc2ccnnc2)(Cc2ccnnc2)c2ccccc21]

This compound was made in a similar manner to 5-chloro-1-ethyl-3-(pyrimidin-4-ylmethyl)indolin-2-one using 1-propylindoline-2,3-dione and 4-methylpyridazine. Yield, 40%. 1H-NMR (CD3OD) δ 8.83 (dd, 2H), 8.66 (s, 2H), 7.77 (d, 1H), 7.26-7.17 (m, 4H), 6.63 (dd, 1H), 3.45 (dd, 4H), 3.25 (d, 2H), 1.10 (m, 2H), 0.49 (t, 3H). Calculated mass for Chemical Formula: $C_{21}H_{21}N_5O$ 359.17, observed 360.2 (M+1, MM API/ESI).

Example 46

1-ethyl-3-hydroxy-5-methyl-3-(pyridazin-3-ylmethyl)indolin-2-one

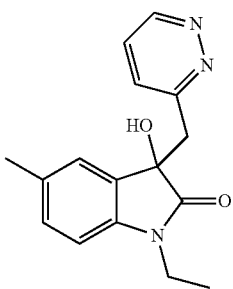 [SMILES: CCN1C(=O)C(O)(Cc2cccnn2)c2cc(C)ccc21]

This compound was made in a similar manner to 5-chloro-1-ethyl-3-(pyrimidin-4-ylmethyl)indolin-2-one using 5-methyl-1-ethylindoline-2,3-dione and 3-methylpyridazine. Yield, 33%. 1H-NMR (CD3OD) δ 8.94 (dd, 1H), 7.50 (m, 2H), 7.05 (dd, 1H), 6.97 (s, 1H), 6.72 (m, 1H), 3.68-3.53 (m, 4H), 2.27 (s, 3H), 1.07 (t, 3H). Calculated mass for Chemical Formula: $C_{16}H_{17}N_3O_2$ 283.13, observed 284.1 (M+1, MM API/ESI).

Example 47

N-(3-((1H-benzo[d]imidazol-2-yl)methyl)-5-chloro-1-ethyl-2-oxoindolin-3-yl)isonicotinamide

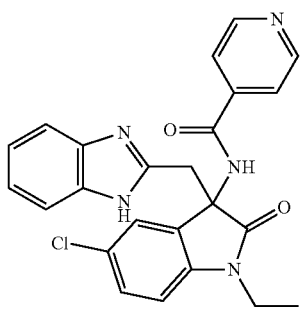 [SMILES: CCN1C(=O)C(Cc2nc3ccccc3[nH]2)(NC(=O)c2ccncc2)c2cc(Cl)ccc21]

This compound was made in a similar manner to 5-chloro-1-ethyl-3-(pyrimidin-4-ylmethyl)indolin-2-one using N-(5-chloro-1-ethyl-2-oxoindolin-3-ylidene)isonicotinamide and 2-methylbenzimidazole. Yield, 10%. 1H-NMR (CDCl3) δ 8.73 (d, 2H), 7.85 (dd, 2H), 7.47 (dd, 2H), 7.26 (dd, 1H), 7.24 (m, 2H), 7.04 (d, 1H), 6.85 (d, 1H), 3.77-3.62 (m, 3H), 3.46 (d, 1H), 1.06 (t, 3H). Calculated mass for Chemical Formula: $C_{24}H_{20}ClN_5O_2$ 445.13, observed 446.1 (M+1, MM API/ESI).

Example 48

3-(benzo[d]oxazol-2-ylmethylene)-5-chloro-1-methylindolin-2-one

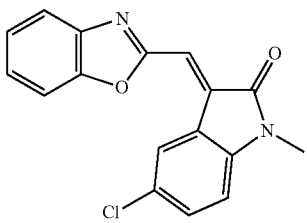 [SMILES: CN1C(=O)/C(=C/c2nc3ccccc3o2)c2cc(Cl)ccc21]

This compound was made in a similar manner to 5-chloro-1-ethyl-3-(pyrimidin-4-ylmethyl)indolin-2-one using 5-chloro-1-methylindoline-2,3-dione and 2-methylbenzoxazole. Yield, 35%. 1H-NMR (CD3OD) δ 9.33 (d, 1H), 7.90 (d, 1H), 7.72 (d, 1H), 7.57-7.44 (m, 4H), 7.01 (d, 1H), 3.28 (s, 3H). Calculated mass for Chemical Formula: $C_{17}H_{11}ClN_2O_2$, 310.05, observed 311.0 (M+1, MM API/ESI).

Example 49

N-(3-((1H-benzo[d]imidazol-2-yl)methyl)-5-chloro-2-oxo-1-propylindolin-3-yl)benzamide

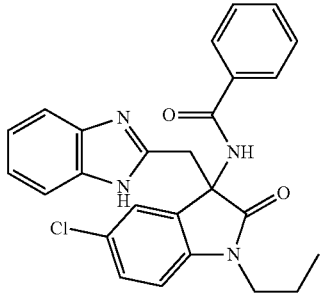 [SMILES: CCCN1C(=O)C(Cc2nc3ccccc3[nH]2)(NC(=O)c2ccccc2)c2cc(Cl)ccc21]

This compound was made in a similar manner to 5-chloro-1-ethyl-3-(pyrimidin-4-ylmethyl)indolin-2-one using N-(1-ethyl-2-oxoindolin-3-ylidene)benzamide and 2-methylbenzimidazole. Yield, 35%. 1H-NMR (CD3OD) δ 7.89 (dd, 2H), 7.57 (m, 1H), 7.57-7.48 (m, 5H), 7.26-7.20 (m, 3H), 6.92 (d, 1H), 6.87 (dd, 1H), 3.69-3.58 (m, 3H), 3.40 (d, 1H), 1.56 (m, 2H), 0.85 (t, 3H). Calculated mass for Chemical Formula: $C_{26}H_{23}ClN_4O_2$, 458.15 observed 459.1 (M+1, MM API/ESI).

Example 50

1-methyl-3-(oxazolo[4,5-b]pyridin-2-ylmethylene)indolin-2-one

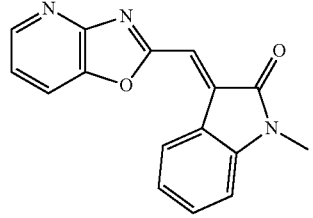 [SMILES: CN1C(=O)/C(=C/c2nc3ncccc3o2)c2ccccc21]

This compound was made in a similar manner to 1-ethyl-3-(pyrimidin-4-ylmethyl)indolin-2-one using 1-methylindoline-2,3-dione and 2-methyloxazolo[4,5-b]pyridine. Yield, 15%. 1H-NMR (CD3OD) δ 9.32 (d, 1H), 8.62 (d, 1H), 8.21 (d, 1H), 7.58 (dd, 1H), 7.51 (m, 2H), 7.19 (dd, 1H), 7.04 (d, 1H) 3.30 (s, 3H). Calculated mass for Chemical Formula: $C_{16}H_{11}N_3O_2$, 277.09, observed 278.1 (M+1, MM API/ESI).

Example 51

5-chloro-2-oxo-1-(2-(piperidin-1-yl)ethyl)-3-(pyridin-2-ylmethyl)indolin-3-yl dimethylcarbamate

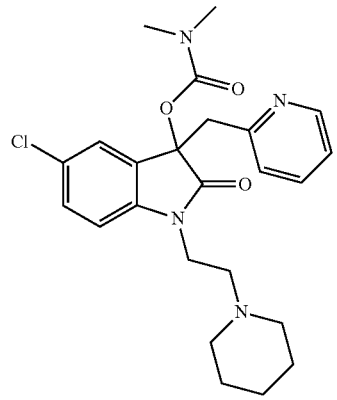 [SMILES: CN(C)C(=O)OC1(Cc2ccccn2)C(=O)N(CCN2CCCCC2)c2ccc(Cl)cc21]

To an oven dried flask cooled under argon was added 5-chloro-3-hydroxy-1-(2-(piperidin-1-yl)ethyl)-3-(pyridin-2-ylmethyl)indolin-2-one (0.025 grams, 0.065 mmol) and DMAP (0.003 grams, 0.025 mmol). This was taken up in 0.65 mL anhydrous dichloromethane. While stirring at room temperature, N,N-dimethylcarbamoyl chloride (0.024 mL, 0.26 mmol) was added followed by triethylamine (0.044 mL, 0.33 mmol). The reaction stirred overnight at room temperature. The next day, the reaction was diluted with methanol, then concentrated. Purification using a Teledyne ISCO combiflash Rf on C18 support (water with 0.1% formic acid/acetonitrile gradient) afforded the desired compound. 6.0 mg, 20% yield. 1H-NMR (CD3OD) δ 8.35 (dd, 1H), 7.71 (dd, 1H), 7.35 (dd, 1H), 7.27 (m, 2H), 7.12 (d, 1H), 6.98 (d, 1H), 4.46 (m, 1H), 3.86 (m, 1H), 3.55 (d, 1H), 3.44-3.31 (m, 7H), 3.10 (s, 3H), 2.83 (s, 3H), 1.87 (bs, 2H), 1.80 (bs, 2H), 1.67 (bs, 2H). Calculated mass for Chemical Formula: $C_{24}H_{29}ClN_4O_3$, 456.19, observed 457.2 (M+1, MM API/ESI).

Example 52

N-(3-((3-methoxypyridin-2-yl)methyl)-2-oxo-1-propylindolin-3-yl)benzamide

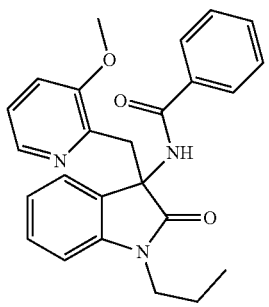 [SMILES: CCCN1C(=O)C(Cc2ncccc2OC)(NC(=O)c2ccccc2)c2ccccc21]

This compound was made in a similar manner to 5-chloro-1-ethyl-3-(pyrimidin-4-ylmethyl)indolin-2-one using N-(1-propyl-2-oxoindolin-3-ylidene)benzamide and 3-methoxy-2-methylpyridine. Yield, 10%. 1H-NMR (CD3OD) δ 8.25 (m, 1H), 7.80 (dd, 2H), 7.55 (dd, 1H), 7.47 (dd, 2H), 7.34 (m, 2H), 7.24 (dd, 1H), 6.98 (d, 1H), 6.83 (dd, 1H), 6.61 (d, 1H), 3.76 (m, 2H), 3.39 (s, 3H), 3.31 (d, 1H), 3.23 (d, 1H), 1.78 (m, 2H), 1.04 (t, 3H). Calculated mass for Chemical Formula: $C_{25}H_{25}N_3O_3$, 415.19, observed 416.2 (M+1, MM API/ESI).

Example 53

N-(5-chloro-1-ethyl-2-oxo-3-(pyridin-2-ylmethyl)indolin-3-yl)-4-methylbenzenesulfonamide

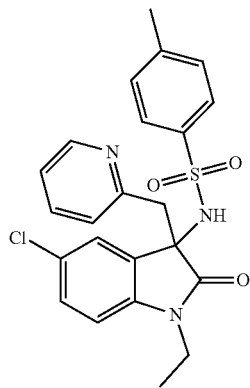 [SMILES: CCN1C(=O)C(Cc2ccccn2)(NS(=O)(=O)c2ccc(C)cc2)c2cc(Cl)ccc21]

To an oven dried vial cooled under argon equipped with a stir bar was added N-(5-chloro-1-ethyl-2-oxoindolin-3-ylidene)-4-methylbenzenesulfonamide (76 mg, 0.21 mmol, 0.3 M in 1,4-dioxane). While stirring at room temperature, 2-picoline (42 μL, 0.42 mmol) and triflic acid (3.7 μL, 0.042 mmol) were added. The mixture was heated using a Biotage microwave reactor on normal settings to 120° C. for 12 hours. The crude reaction mixture was concentrated. Purification was accomplished by using a Teledyne ISCO combiflash on silica support (hexanes/ethyl acetate gradient) followed by reverse phase chromatography using a C18 support (water with 0.1% formic acid/acetonitrile gradient) to afford the desired product in 25% yield (24 mg). 1H NMR (CDCl3) δ 8.70-8.63 (m, 2H), 7.69 (t, 1H), 7.35 (m, 3H), 7.14-7.11 (m, 3H), 6.98 (d, 1H), 6.74 (d, 1H), 5.77 (s, 1H), 3.87 (m, 1H), 3.69 (m, 1H), 3.26 (d, 1H), 2.94 (d, 1H), 2.36 (s, 3H), 1.31 (t, 3H). Calculated mass for chemical formula: $C_{23}H_{22}ClN_3O_3S$ 455.11, observed, 456.1. (MM: ESI+APCI, M+1).

Example 54

3-(1-ethyl-5-methyl-3-((1-methyl-1H-indazol-4-yl)methyl)-2-oxoindolin-3-yl)-1,1-dimethylurea

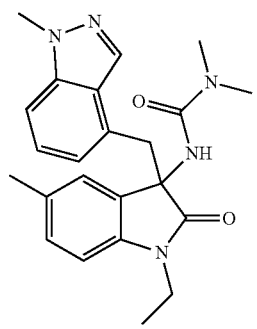

To an oven dried vial cooled under argon equipped with a stir bar was added 3-(1-ethyl-5-methyl-2-oxoindolin-3-yl)-1,1-dimethylurea (50 mg, 0.19 mmol, 0.5 M solution in toluene). While stirring at room temperature, LiHMDS (0.29 mL, 0.29 mmol, 1.0 M solution in THF) was added. After stirring at room temperature for 15 minutes, 4-(chloromethyl)-1-methyl-1H-indazole (45 mg, 0.25 mmol, 0.5 M solution in DMF) was added. The reaction continued to stir until the starting material was consumed. The reaction was quenched with a saturated NH4Cl solution and extracted with acetonitrile. The aqueous layer was salted out and washed with acetonitrile. The combined organic material was then dried with Na2SO4, filtered, and concentrated. Purification was achieved by a Teledyne ISCO combiflash on C18 support (water with 0.1% formic acid/acetonitrile gradient) to afford the final material in 69% yield (53 mg). 1H NMR (CD3OD) δ 7.74 (s, 1H), 7.27 (d, 1H), 7.20 (s, 1H), 7.05 (t, 1H), 6.89 (dd, 1H), 6.48 (d, 1H), 6.39 (d, 1H), 3.93 (s, 3H), 3.56 (s, 2H), 3.44 (m, 1H), 3.19 (m, 1H), 2.91 (s, 6H), 2.33 (s, 3H), 0.50 (t, 3H). Calculated mass for chemical formula: $C_{23}H_{27}N_5O_2$ 405.22, observed, 406.2. (MM: ESI+APCI, M+1).

Example 55

1,1-dimethyl-3-(3-((1-methyl-1H-indazol-4-yl)methyl)-2-oxo-1-propylindolin-3-yl)urea

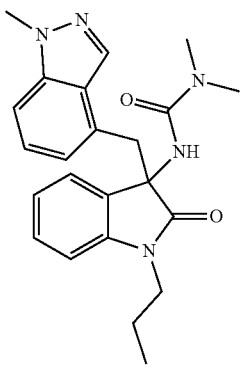

1,1-dimethyl-3-(3-((1-methyl-1H-indazol-4-yl)methyl)-2-oxo-1-propylindolin-3-yl)urea was made in a similar manner as 3-(1-ethyl-5-methyl-3-((1-methyl-1H-indazol-4-yl)methyl)-2-oxoindolin-3-yl)-1,1-dimethylurea, using 1,1-dimethyl-3-(2-oxo-1-propylindolin-3-yl)urea and 4-(chloromethyl)-1-methyl-1H-indazole. Purification was accomplished using a Teledyne ISCO combiflash C18 support (water with 0.1% formic acid/acetonitrile gradient) followed by a subsequent Teledyne ISCO combiflash silica support (hexanes/ethyl acetate gradient followed by an acetonitrile flush) to afford the desired compound at 45% yield (35 mg). 1H NMR (CD$_3$OD) δ 7.78 (s, 1H), 7.38 (d, 1H), 7.27 (d, 1H), 7.09 (t, 1H), 7.04 (m, 2H), 6.52 (d, 1H), 6.44 (d, 1H), 3.94 (s, 3H), 3.58 (s, 2H), 3.37 (m, 1H), 3.09 (m, 1H), 2.91 (s, 6H), 0.92 (m, 2H), 0.49 (t, 3H). Calculated mass for chemical formula: C$_{23}$H$_{27}$N$_5$O$_2$ 405.22, observed, 406.2. (MM: ESI+APCI, M+1).

Example 56

3-(3-(benzo[d][1,3]dioxol-4-ylmethyl)-2-oxo-1-propylindolin-3-yl)-1,1-dimethylurea

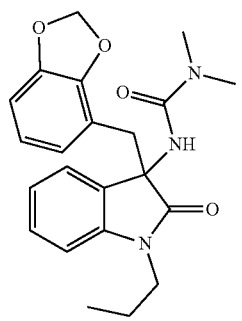 [SMILES: CCCN1C(=O)C(Cc2cccc3c2OCO3)(NC(=O)N(C)C)c2ccccc21]

To an oven dried vial cooled under argon equipped with a stir bar was added 1,1-dimethyl-3-(2-oxo-1-propylindolin-3-yl)urea (50 mg, 0.191 mmol, 0.3 M solution in toluene). While stirring at room temperature, LiHMDS (0.25 mL, 0.25 mmol, 1.0 M solution in THF) was added. After stirring for 15 minutes, 4-(chloromethyl)benzo[d][1,3]dioxole (0.83 mL, 0.25 mmol, 0.3 M solution in DMF) was added. The reaction was stirred until the starting material had been consumed. The reaction was quenched with a saturated NH$_4$Cl solution and extracted with acetonitrile. The aqueous layer was salted out and washed with acetonitrile. The combined organic material was dried with Na$_2$SO$_4$, filtered, and concentrated. Purification was accomplished by using a Teledyne ISCO combiflash silica support (hexanes/ethyl acetate gradient followed by an acetonitrile flush) to afford the desired compound in 51% yield (38 mg). 1H NMR (CD$_3$OD) δ 7.12, (m, 2H), 6.97 (t, 1H), 6.58 (d, 1H), 6.57 (m, 2H), 6.26 (dd, 1H), 5.78 (d, 1H), 5.47 (d, 1H), 3.56 (m, 1H), 3.40 (m, 1H), 3.02 (d, 1H), 2.98 (d, 1H), 2.96 (s, 6H), 1.49 (m, 2H), 0.85 (t, 3H). Calculated mass for chemical formula: C$_{22}$H$_{25}$N$_3$O$_4$ 395.18, observed, 396.3. (MM: ESI+APCI, M+1).

Example 57

3-(3-(benzo[d][1,3]dioxol-4-ylmethyl)-5-chloro-1-methyl-2-oxoindolin-3-yl)-1,1-dimethylurea

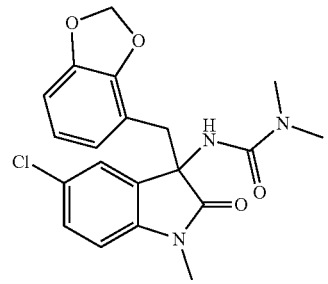 [SMILES: CN(C)C(=O)NC1(Cc2cccc3c2OCO3)C(=O)N(C)c2ccc(Cl)cc21]

3-(3-(benzo[d][1,3]dioxol-4-ylmethyl)-5-chloro-1-methyl-2-oxoindolin-3-yl)-1,1-dimethylurea was made in a similar manner to 3-(3-(benzo[d][1,3]dioxol-4-ylmethyl)-2-oxo-1-propylindolin-3-yl)-1,1-dimethylurea, using 3-(5-chloro-1-methyl-2-oxoindolin-3-yl)-1,1-dimethylurea and 4-(chloromethyl)benzo[d][1,3]dioxole. Purification was accomplished using a Teledyne ISCO combiflash silica support (hexanes/ethyl acetate gradient followed by an acetonitrile flush) followed by a subsequent Teledyne ISCO combiflash C18 support (water with 0.1% formic acid/acetonitrile gradient) to afford the desired compound in 59% yield (35 mg). 1H NMR (CD$_3$OD) δ 7.16 (dd, 1H), 7.12 (d, 1H), 6.60 (m, 3H), 6.35 (dd, 1H), 5.82 (d, 1H), 5.47 (d, 1H), 3.38 (d, 1H), 2.98 (s, 3H), 2.95 (d, 1H), 2.89 (s, 6H). Calculated mass for chemical formula: C$_{20}$H$_{20}$ClN$_3$O$_4$ 401.11, observed, 402.1. (MM: ESI+APCI, M+1).

Example 58

3-(3-(benzo[d][1,3]dioxol-4-ylmethyl)-5-chloro-2-oxo-1-propylindolin-3-yl)-1,1-dimethylurea

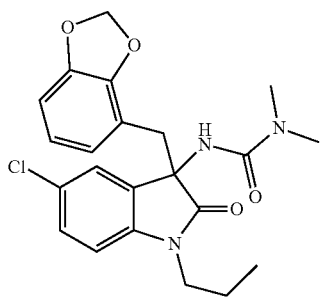 [SMILES: CCCN1C(=O)C(Cc2cccc3c2OCO3)(NC(=O)N(C)C)c2cc(Cl)ccc21]

3-(3-(benzo[d][1,3]dioxol-4-ylmethyl)-5-chloro-2-oxo-1-propylindolin-3-yl)-1,1-dimethylurea was made in a similar manner to 3-(3-(benzo[d][1,3]dioxol-4-ylmethyl)-2-oxo-1-propylindolin-3-yl)-1,1-dimethylurea, using 3-(5-chloro-2-oxo-1-propylindolin-3-yl)-1,1-dimethylurea and 4-(chloromethyl)benzo[d][1,3]dioxole. Purification was accomplished by using a Teledyne ISCO combiflash silica support (hexanes/ethyl acetate gradient followed by an acetonitrile flush) followed by a subsequent Teledyne ISCO combiflash C18 support (water with 0.1% formic acid/acetonitrile gradient) to afford the desired compound in 45% yield (23 mg). 1H NMR (CD$_3$OD) δ 7.16 (m, 2H), 6.68 (d, 1H), 6.59 (m, 2H), 6.33 (dd, 1H), 5.82 (d, 1H), 5.48 (d, 1H), 3.52 (m, 1H), 3.40 (m, 1H), 3.37 (d, 1H), 3.00 (d, 1H), 2.89 (s, 6H), 1.47 (m, 2H), 0.84 (t, 3H). Calculated mass for chemical formula: C$_{22}$H$_{24}$ClN$_3$O$_4$ 429.15, observed, 430.2. (MM: ESI+APCI, M+1).

Example 59

3-(1,5-dimethyl-2-oxo-3-(3,4,5-trimethoxybenzyl)indolin-3-yl)-1,1-dimethylurea

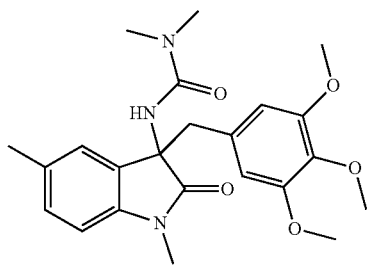

To an oven dried vial cooled under argon equipped with a stir bar was added 3-(1,5-dimethyl-2-oxoindolin-3-yl)-1,1-dimethylurea (50 mg, 0.20 mmol, 0.3 M solution in toluene). While stirring at room temperature, LiHMDS (0.26 mL, 0.26 mmol, 1.0 M solution in THF) was added. After stirring for 15 minutes, 5-(chloromethyl)-1,2,3-trimethoxybenzene (57 mg, 0.26 mmol, 0.3 M solution in DMF) was added. The reaction was stirred until the starting material was consumed. The reaction was quenched with a saturated solution of NH$_4$Cl and extracted with acetonitrile. The aqueous layer was salted out and washed with acetonitrile. The combined organic material was dried with Na$_2$SO$_4$, filtered, and concentrated. Purification was accomplished by using a Teledyne ISCO combiflash silica support (hexanes/ethyl acetate gradient followed by an acetonitrile flush) followed by a subsequent Teledyne ISCO combiflash C18 support (water with 0.1% formic acid/acetonitrile gradient) to afford the desired compound in 43% yield (37 mg). 1H NMR (CD$_3$OD) δ 7.16 (s, 1H), 7.03 (dd, 1H), 6.52 (d, 1H), 5.97 (s, 2H), 3.63 (s, 3H), 3.56 (s, 6H), 3.17 (d, 1H), 3.09 (d, 1H), 2.90 (s, 6H), 2.85 (s, 3H), 2.36 (s, 3H). Calculated mass for chemical formula: C$_{23}$H$_{29}$N$_3$O$_5$ 427.21, observed, 428.2. (MM: ESI+APCI, M+1).

Example 60

3-(1-ethyl-2-oxo-3-(3,4,5-trimethoxybenzyl)indolin-3-yl)-1,1-dimethylurea

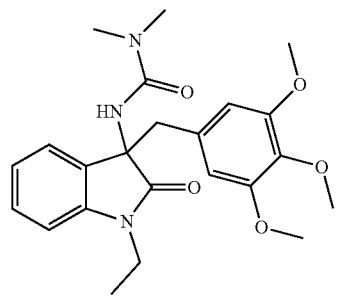 [SMILES: CCN1C(=O)C(Cc2cc(OC)c(OC)c(OC)c2)(NC(=O)N(C)C)c2ccccc21]

3-(1-ethyl-2-oxo-3-(3,4,5-trimethoxybenzyl)indolin-3-yl)-1,1-dimethylurea was made in a similar manner to 3-(1,5-dimethyl-2-oxo-3-(3,4,5-trimethoxybenzyl)indolin-3-yl)-1,1-dimethylurea, using 3-(1-ethyl-2-oxoindolin-3-yl)-1,1-dimethylurea and 5-(chloromethyl)-1,2,3-trimethoxybenzene. Purification was accomplished by using a Teledyne ISCO combiflash silica support (hexanes/ethyl acetate gradient followed by an acetonitrile flush) followed by a subsequent Teledyne ISCO combiflash C18 support (water with 0.1% formic acid/acetonitrile gradient) to afford the desired compound in 35% yield (30 mg). 1H NMR (CD$_3$OD) δ 7.38 (d, 1H), 7.23 (t, 1H), 7.13 (t, 1H), 6.70 (d, 1H), 5.91 (s, 2H), 3.64 (m, 1H), 3.61 (s, 3H), 3.58 (s, 6H), 3.31 (m, 1H), 3.23 (d, 1H), 3.11 (d, 1H), 2.90 (s, 6H), 0.76 (t, 3H). Calculated mass for chemical formula: C$_{23}$H$_{29}$N$_3$O$_5$ 427.21, observed, 428.2. (MM: ESI+APCI, M+1).

Example 61

3-(3-((1-benzoyl-1H-indol-3-yl)methyl)-1-ethyl-2-oxoindolin-3-yl)-1,1-dimethylurea

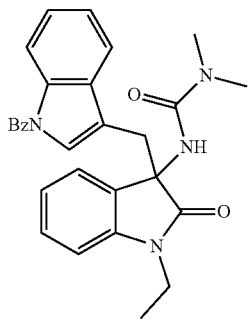

To an oven dried vial cooled under argon equipped with a stir bar was added 3-(1-ethyl-2-oxoindolin-3-yl)-1,1-dimethylurea (50 mg, 0.20 mmol, 0.5 M solution in toluene). While stirring at room temperature, LiHMDS (0.30 mL, 0.30 mmol, 1.0 M solution in THF) was added. After stirring for 15 minutes, (1-benzoyl-1H-indol-3-yl)methyl benzoate (93 mg, 0.26 mmol, 0.5 M solution in DMF) was added. The reaction was stirred until the starting material was consumed. The reaction was quenched with 30 μL of glacial acetic acid, diluted with water, and extracted with acetonitrile. The aqueous layer was salted out and washed with acetonitrile. The combined organic material was dried with $Na_2SO_4$, filtered, and concentrated. Purification was accomplished by using a Teledyne ISCO combiflash silica support (hexanes/ethyl acetate gradient followed by an acetonitrile flush) followed by a subsequent Teledyne ISCO combiflash C18 support (water with 0.1% formic acid/acetonitrile gradient) to afford the desired compound in 37% yield (35 mg). 1H NMR ($CD_3OD$) δ 8.23 (d, 1H), 7.63 (t, 1H), 7.52 (m, 3H), 7.28 (m, 6H), 7.06 (t, 1H), 6.74 (d, 1H), 6.28 (s, 1H), 3.47 (m, 2H), 3.21 (m, 2H), 2.86 (s, 6H), 0.41 (t, 3H). Calculated mass for chemical formula: $C_{29}H_{28}N_4O_3$ 480.22, observed, 481.2. (MM: ESI+APCI, M+1).

Example 62

3-(3-((1-benzoyl-1H-indol-3-yl)methyl)-1-methyl-2-oxoindolin-3-yl)-1,1-dimethylurea

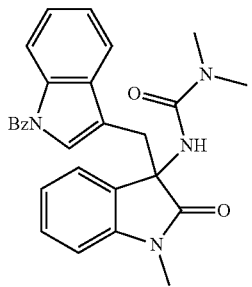

3-(3-((1-benzoyl-1H-indol-3-yl)methyl)-1-methyl-2-oxoindolin-3-yl)-1,1-dimethylurea was made in a similar manner to 3-(3-((1-benzoyl-1H-indol-3-yl)methyl)-1-ethyl-2-oxoindolin-3-yl)-1,1-dimethylurea, using 1,1-dimethyl-3-(1-methyl-2-oxoindolin-3-yl)urea and (1-benzoyl-1H-indol-3-yl)methyl benzoate as the starting materials. Purification was accomplished by using a Teledyne ISCO combiflash silica support (hexanes/ethyl acetate gradient followed by an acetonitrile flush) followed by a subsequent Teledyne ISCO combiflash C18 support (water with 0.1% formic acid/acetonitrile gradient) to afford the desired compound in 35% yield (34 mg). 1H NMR ($CD_3OD$) δ 8.23 (d, 1H), (t, 1H), (m, 3H), (d, 1H), 7.23 (m, 5H), 7.06 (t, 1H), 6.70 (d, 1H), 6.41 (s, 1H), 3.41 (d, 1H), 3.29 (d, 1H), 2.89 (s, 6H), 2.74 (s, 3H). Calculated mass for chemical formula: $C_{28}H_{26}N_4O_3$ 466.20, observed, 467.2. (MM: ESI+APCI, M+1).

Example 63

3-(3-((1-benzoyl-1H-indol-3-yl)methyl)-2-oxo-1-propylindolin-3-yl)-1,1-dimethylurea

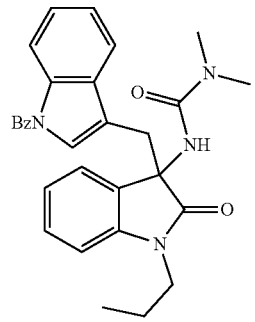

3-(3-((1-benzoyl-1H-indol-3-yl)methyl)-2-oxo-1-propylindolin-3-yl)-1,1-dimethylurea was made in a similar manner to 3-(3-((1-benzoyl-1H-indol-3-yl)methyl)-1-ethyl-2-oxoindolin-3-yl)-1,1-dimethylurea, using 1,1-dimethyl-3-(2-oxo-1-propylindolin-3-yl)urea and (1-benzoyl-1H-indol-3-yl)methyl benzoate as the starting materials. Purification was accomplished by using a Teledyne ISCO combiflash silica support (hexanes/ethyl acetate gradient followed by an acetonitrile flush) followed by a subsequent Teledyne ISCO combiflash C18 support (water with 0.1% formic acid/acetonitrile gradient) to afford the desired compound in 22% yield (21 mg). 1H NMR ($CD_3OD$) δ 8.24 (d, 1H), 7.63 (t, 1H), 7.52 (m, 3H), 7.25 (m, 6H), 7.06 (t, 1H), 6.74 (d, 1H), 6.31 (s, 1H), 3.46 (d, 1H), 3.43 (m, 1H), 3.31 (d, 1H), 3.12 (m, 1H), 2.88 (s, 6H), 0.90 (m, 1H), 0.77 (m, 1H), 0.46 (t, 3H). Calculated mass for chemical formula: $C_{30}H_{30}N_4O_3$ 494.23, observed, 495.2. (MM: ESI+APCI, M+1).

Example 64

3-(3-((1-benzoyl-1H-indol-3-yl)methyl)-5-methyl-2-oxo-1-propylindolin-3-yl)-1,1-dimethylurea

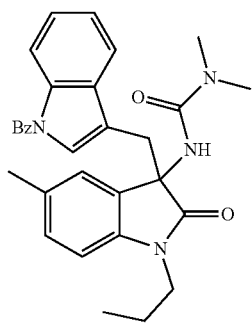

3-(3-((1-benzoyl-1H-indol-3-yl)methyl)-5-methyl-2-oxo-1-propylindolin-3-yl)-1,1-dimethylurea was made in a similar manner to 3-(3-((1-benzoyl-1H-indol-3-yl)methyl)-1-ethyl-2-oxoindolin-3-yl)-1,1-dimethylurea, using 1,1-dimethyl-3-(5-methyl-2-oxo-1-propylindolin-3-yl)urea and (1-benzoyl-1H-indol-3-yl)methyl benzoate as the starting materials. Purification was accomplished by using a Teledyne ISCO combiflash C18 support (water with 0.1% formic acid/acetonitrile gradient) followed by a subsequent Teledyne ISCO combiflash silica support (hexanes/ethyl acetate gradient followed by an acetonitrile flush) to afford the desired compound in 25% yield (45 mg). 1H NMR (CD$_3$OD) δ 8.25 (d, 1H), 7.63 (t, 1H), 7.52 (m, 3H), 7.27 (m, 4H), 7.10 (s, 1H), 7.05 (dd, 1H), 6.61 (d, 1H), 6.20 (s, 1H), 3.43 (d, 1H), 3.38 (m, 1H), 3.23 (d, 1H), 3.05 (m, 1H), 2.88 (s, 6H), 2.27 (s, 3H), 0.86 (m, 1H), 0.71 (m, 1H), 0.43 (t, 3H). Calculated mass for chemical formula: C$_{31}$H$_{32}$N$_4$O$_3$ 508.25, observed, 509.3. (MM: ESI+APCI, M+1).

Example 65

2-((5-chloro-1-ethyl-3-hydroxy-2-oxoindolin-3-yl)methyl)-6-methoxyphenyl dimethylsulfamate

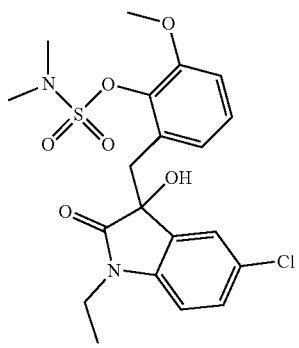 [SMILES: CCN1C(=O)C(O)(Cc2cccc(OC)c2OS(=O)(=O)N(C)C)c2cc(Cl)ccc21]

To a clean round bottom flask charged with 5-chloro-1-ethyl-3-hydroxy-3-(2-hydroxy-3-methoxybenzyl)indolin-2-one (0.027 grams, 0.078 mmol) was added DMAP (0.003 grams, 0.03 mmol), and taken up in 1.0 mL of dichloromethane. While stirring at room temperature triethylamine (0.016 mL, 0.12 mmol) was added followed by N,N-dimethylsulfamoyl chloride (0.0083 uL, 0.078 mmol). The reaction stirred at room temperature and was monitored by LCMS. Once complete, the reaction was diluted with methanol and concentrated. Purification was accomplished by using a Teledyne ISCO combiflash on C18 support (water with 0.1% formic acid/acetonitrile gradient) to afford the desired compound in 15% yield (5.2 mg). 1H NMR (CD$_3$OD) δ 7.23 (m, 2H), 7.05 (dd, 1H), 6.88 (dd, 1H), 6.80 (dd, 1H), 6.75 (d, 1H), 3.75 (s, 3H), 3.67 (m, 2H), 3.47 (m, 1H), 3.31 (m, 4H), 2.96 (s, 3H), 1.03 (s, 3H). Calculated mass for chemical formula, C$_{20}$H$_{23}$ClN$_2$O$_6$S, 454.10, observed 455.1 (MM; APCI/ESI, M+1)).

The compounds of the invention were tested in various biological assays below. The results of these assays indicated that the compounds of the invention ameliorated dysregulated bioenergetics and are, thus, useful for treatment of degenerative diseases and disorders, such as retinal damage.

Example 66

MTT Assay

The compound 3-(4,5-Dimethylthiazol-2-yl)-2,5-diphenyltetrazolium bromide (MTT) is a tetrazolium ion that is reduced to a blue formazan dye via several families of NAD(P)H-dependent oxidoreductases. Formation of the formazan dye from MTT or other related tetrazolium dyes are commonly used as a viability assay even though, in fact, the assay is a metabolic capacity assay. While it is true that dead cells cannot produce NAD(P)H, very sick cells in the throes of death can exhibit extremely high levels of metabolic capacity as they attempt to overcome stress and it is well known that the MTT and related assays report on the ability of cells to produce reducing equivalents, and not live-dead ratios (Sumantran 2011). As shown below, it was found that the MTT assay was a useful metabolic assay when linked to more specific bioenergetic assays.

In this assay, 661W or C6 cells were maintained in DMEM supplemented with 10% serum. 100 of 70,000 cells/mL cells were seeded into each well of 96 well plates using DMEM supplemented with 5% serum. Cells were then allowed to grow to confluency for 48 hours. Representative compounds of the invention were added in 2 μL media and calcium-ionophore A23187 was then added in 1 μL for a final concentration of 1 μM and after 24 h, 20 uL of 2 μg/mL MTT were added to each well and the cells were incubated for another 4 h after which 100 μL of 1% SDS in 0.01 M aqueous HCl were added to each well and the plates were incubated overnight. Absorbance was measured at 640 and 570 nM (background correction). The 1 μM ionophore A23187 caused about 50% loss in MTT signal at 24 h. Protection was calculated as the increase in absorbance of treatment groups normalized to the vehicle control.

As shown in Table 1, representative compounds of the invention gave significant protection from calcium-mediated loss of metabolic capacity at low concentrations:

TABLE 1

| Metabolic Protection Assay (MTT) | |
|---|---|
| Example No. | % protection, concentration[a] |
| 1 | 58%, 1 pM |
| 2 | 100%, 50 pM |

TABLE 1-continued

Metabolic Protection Assay (MTT)

| Example No. | % protection, concentration[a] |
|---|---|
| 3 | 66%, 100 pM |
| 4 | 73%, 100 pM |
| 5 | 72%, 500 pM |
| 6 | 72%, 50 pM |
| 7 | 70%, 800 pM |
| 8 | 69%, 500 pM |
| 9 | 80%, 800 pM |
| 10 | 76%, 50 pM |
| 11 | 59%, 50 pM |
| 12 | 98%, 1 nM |
| 13 | 58%, 100 pM |
| 14 | 61%, 100 pM |
| 15 | 72%, 100 pM |
| 16 | 81%, 50 pM |
| 17 | 85%, 100 pM |
| 18 | 83%, 100 pM |
| 19 | 85%, 100 pM |
| 20 | 73%, 100 pM |
| 21 | 58%, 100 pM |
| 22 | 68%, 100 pM |
| 23 | 59%, 50 pM |
| 24 | 58%, 100 pM |
| 25 | 53%, 800 pM |
| 26 | 64%, 50 pM |
| 27 | 69%, 100 pM |
| 28 | 72%, 500 pM |
| 29 | 75%, 1 nM |
| 30 | 71%, 100 pM |
| 31 | 72%, 500 pM |
| 32 | 62%, 1 nM |
| 33 | 49%, 50 pM |
| 34 | 50%, 100 pM |
| 35 | 68%, 1 nM |
| 36 | 55%, 100 pM |
| 37 | 63%, 1 nM |
| 38 | 54%, 100 pM |
| 39 | 53%, 100 pM |
| 40 | 50%, 50 pM |
| 41 | 70%, 1 nM |
| 42 | 55%, 1 nM |
| 43 | 63%, 800 pM |
| 44 | 51%, 800 pM |
| 45 | 59%, 100 pM |
| 46 | 50%, 100 pM |
| 47 | 74%, 500 pM |
| 48 | 82%, 800 pM |
| 49 | 64%, 100 pM |
| 50 | 61%, 1 nM |
| 51 | 50%, 100 pM |
| 52 | 56%, 800 pM |
| 53 | 46%, 50 pM |
| 54 | 62%, 100 pM |
| 55 | 68%, 1 nM |
| 56 | 51%, 100 pM |
| 57 | 58%, 1 nM |
| 58 | 70%, 800 pM |
| 59 | 57%, 50 pM |
| 60 | 57, 100 pM |
| 61 | 60%, 100 pM |
| 62 | 54%, 100 pM |
| 63 | 66%, 500 pM |
| 64 | 56%, 500 pM |
| 65 | 48%, 100 pM |

[a]Concentration at which maximum protection is observed

Example 67

Retinal Degeneration

The in vitro data demonstrated that the compounds of the invention mitigated oxidative- and calcium-induced loss of mitochondrial metabolic capacity. It was reasoned that the compounds' activities would enable them to protect against loss of photoreceptors in retinal degenerative animal models. Hence, mouse retinal degeneration models were utilized that result from oxidative stress and/or calcium overload.

Rd1 Mouse Model of RP

For the calcium-overload in vitro, the rd1 mouse was utilized (e.g., Farber et al., 1995). The genotype of the rd1 mouse has a mutation in the β-subunit of the phosphodiesterase gene. This mutation results in high levels of cGMP, leaving an increased number of the cGMP-gated channels in the open state, allowing intracellular calcium to rise to toxic levels and rapid rod degeneration. The genetic deficit and the retinal pathology are very similar to that observed in the patients with βPDE-dependent RP. In these mice, rod photoreceptor degeneration started after postnatal day 10 (P10), and progressing rapidly. By day 21, only one row of photoreceptors remains, which represents the cones. This retina is amenable to replicating retinal development and degeneration in organ cultures (Ogilvie et al., 2001). To test the potential therapeutic efficacy, compounds were added to the culture media starting the day after the start of the culture (equivalent to postnatal day 11) and replaced every 48 hours. Effects were assessed on the degeneration of photoreceptor cells morphologically at the equivalent of postnatal day 21. In control rd1 mice, over ~90% of the photoreceptors are eliminated by P21 (average retina score: 2.3±0.24 rows of photoreceptors). On the other hand, the mice treated with representative compounds of the invention (eye drops once per day) retained significantly more photoreceptors cells (Table 2):

TABLE 2

| Example No. | rd1 vehicle (# of rows) | rd1 protection (concentration; # of rows; P-value) |
|---|---|---|
| 10 | 1.81 ± 0.09 | (10 nM) 2.51 ± 0.25 (P = 0.04) |

Rd10 Mouse Model of RP

For the calcium-overload, the rd10 mouse was utilized (e.g., Phillips et al., 2008). The genotype of the rd10 mouse has a mutation in the β-subunit of the phosphodiesterase gene. This mutation results in high levels of cGMP, leaving an increased number of the cGMP-gated channels in the open state, allowing intracellular calcium to rise to toxic levels and rapid rod degeneration. The genetic deficit and the retinal pathology are very similar to that observed in the patients with βPDE-dependent RP. In these mice, rod photoreceptor degeneration started after postnatal day 10 (P10), progressing rapidly. The maximal response of the electroretinogram, which measure as the function of the retina in response to light, occurs at 3 weeks of age and is nondetectable at 2 months of age. To test the potential therapeutic efficacy, eye drops were formulated in 0.1% Myrj in 0.9% saline, applied once daily starting at the day of eye opening (postnatal day 14), and their effect assessed on the degeneration of photoreceptor cells morphologically at postnatal day 25. In control rd10 mice, over ~75% of the photoreceptors are eliminated by P25 (average retina score: 2.3±0.24 rows of photoreceptors). On the other hand, the mice treated with representative compounds of the invention (eye drops once per day) retained significantly more photoreceptors cells (Table 3):

TABLE 3

| Example No. | Rd10 vehicle (# of rows) | rd10 protection (concentration; # of rows; P-value) |
|---|---|---|
| 10 | 2.3 ± 0.23 | (100 µM) 2.8 ± 0.48 (P < 0.005) |

Example 68

Light Model Assay

The light model assay is generally accepted as a model of age related macular degeneration (AMD). Light as an environmental factor has been shown to be toxic to rod photoreceptors if the retina was exposed to high light levels over a long period of time; and oxidative stress has been implicated as the main trigger for cell death. In particular, oxidative damage has been detected by immunohistochemistry, detecting the presence of oxidized and tyrosine-phosphorylated proteins as well as the upregulation of endogenous antioxidants such as thioredoxin and glutathione peroxidase. Likewise, exogenous antioxidants have been found to protect the rodent retina from light damage. Additional indirect evidence for the involvement of oxidative stress in photoreceptor degeneration has been provided by treatment of photodamaged retinas with antioxidants such as dimethylthiourea, or the treatment of N-methyl-N-nitrosourea (MNU)-challenged rats with the antioxidant DHA.

The light model assay was used to further test the therapeutic potential of the compounds of the invention. Photoreceptors from albino animals are very sensitive to constant light, lacking the RPE pigment to protect them. Thus, Balb/c mice were exposed to continuous light for 7 days, which caused loss of about 50% of the photoreceptor cells as measured via histology. To test the potential therapeutic efficacy, eye drops were formulated in 0.1% Myrj in 0.9% saline, applied once daily throughout the period of light exposure, and their effect assessed on the light-induced degeneration of photoreceptor cells morphologically and electrophysiologically, 10 days after the onset of the CL exposure. In control BALB/c mice, constant light resulted in the elimination of ~50% of the photoreceptors (average retina score: 4.3±0.25 rows of photoreceptors). Based on the position of the light source, the ventral half of the retina is more severely affected than the dorsal half (ventral has typically ~2 rows less than the dorsal half). Interestingly, some compounds have differential effects on the two halves, typically having a greater effect in the half of the retina that is more severely affected by the light. The maximum effect of the representative compounds of the invention (eye drops once per day) are reported in Table 4:

TABLE 4

| Example No. | LD Vehicle (# of rows) | LD Protection (concentration, # of rows; P-value) |
|---|---|---|
| 10 | 3.8 ± 0.20 | (100 µM) 5.8 ± 0.34 (P < 0.001) |
| 12 | 3.8 ± 0.20 | (100 µM) 4.87 ± 0.22 (P < 0.01) |
| 17 | 5.71 ± 0.14 | (100 µM) 6.48 ± 0.13 (P < 0.001) |

As seen in the Examples above, the compounds of the invention mitigate oxidative- and calcium-mediated loss of mitochondrial capacity in cell lines and protect photoreceptors from cell death in several models of retinal degeneration.

REFERENCES

Acosta M L, Fletcher E L, Azizoglu S, Foster L E, Farber D B, Kalloniatis M: Early markers of retinal degeneration in rd/rd mice. Mol Vis 2005, 11:717-728.

Acosta M L, Shin Y S, Ready S, Fletcher E L, Christie D L, Kalloniatis M. Retinal metabolic state of the proline-23-histidine rat model of retinitis pigmentosa. Am J Physiol Cell Physiol. 2010 March; 298(3):C764-74. doi: 10.1152/ajpcell.00253.2009. Epub 2009 Dec. 23. PubMed PMID: 20032515.

Barot M, Gokulgandhi M R, Mitra A K. Mitochondrial dysfunction in retinal diseases. Curr Eye Res. 2011 December; 36(12):1069-77. doi: 10.3109/02713683.2011.607536. Epub 2011 Oct. 6. Review. PubMed PMID: 21978133.

Beal D M, Jones L H. Molecular scaffolds using multiple orthogonal conjugations: applications in chemical biology and drug discovery. Angew Chem Int Ed Engl. 2012 Jun. 25; 51(26):6320-6. doi: 10.1002/anie. 201200002. Epub 2012 Apr. 19. Review. PubMed PMID: 22517597.

Beeson C C, Beeson G C, Schnellmann R G. A high-throughput respirometric assay for mitochondrial biogenesis and toxicity. Anal Biochem. 2010 Sep. 1; 404(1):75-81. doi: 10.1016/j.ab. 2010.04.040. Epub 2010 May 11. PubMed PMID: 20465991; PubMed Central PMCID: PMC2900494.

Booij J C, van Soest S, Swagemakers S M, Essing A H, Verkerk A J, van der Spek P J, Gorgels T G, Bergen A A. Functional annotation of the human retinal pigment epithelium transcriptome. BMC Genomics. 2009 Apr. 20; 10:164. doi: 10.1186/1471-2164-10-164. PubMed PMID: 19379482; PubMed Central PMCID: PMC2679759.

Bruce J E. In vivo protein complex topologies: sights through a cross-linking lens. Proteomics. 2012 May; 12(10):1565-75. doi: 10.1002/pmic. 201100516. Review. PubMed PMID: 22610688.

Catoire M, Mensink M, Boekschoten M V, Hangelbroek R, Müller M, Schrauwen P, Kersten S. Pronounced effects of acute endurance exercise on gene expression in resting and exercising human skeletal muscle. PLoS One. 2012; 7(11):e51066. doi: 10.1371/journal.pone. 0051066. Epub 2012 Nov. 30. PubMed PMID: 23226462; PubMed Central PMCID: PMC3511348.

Cavalier-Smith T, Chao E E. Phylogeny of choanozoa, apusozoa, and other protozoa and early eukaryote mega-evolution. J Mol Evol. 2003 May; 56(5):540-63. PubMed PMID: 12698292.

Cazares L H, Troyer D A, Wang B, Drake R R, Semmes O J. MALDI tissue imaging: from biomarker discovery to clinical applications. Anal Bioanal Chem. 2011 July; 401(1):17-27. doi: 10.1007/s00216-011-5003-6. Epub 2011 May 4. Review. PubMed PMID: 21541816.

Chaurand P, Cornett D S, Caprioli R M. Molecular imaging of thin mammalian tissue sections by mass spectrometry. Curr Opin Biotechnol. 2006 August; 17(4):431-6. Epub 2006 Jun. 16. Review. PubMed PMID: 16781865.

Chen Y A, Almeida J S, Richards A J, Müller P, Carroll R J, Rohrer B. A nonparametric approach to detect nonlinear correlation in gene expression. J Comput Graph Stat. 2010 Sep. 1; 19(3):552-568. PubMed PMID: 20877445; PubMed Central PMCID: PMC2945392.

Copple I M. The Keap1-Nrf2 cell defense pathway—a promising therapeutic target? Adv Pharmacol. 2012; 63:43-79. doi: 10.1016/B978-0-12-398339-8.00002-1. Review. PubMed PMID: 22776639.

Court F A, Coleman M P. Mitochondria as a central sensor for axonal degenerative stimuli. Trends Neurosci. 2012 June; 35(6):364-72. doi: 10.1016/j.tins. 2012.04.001. Epub 2012 May 11. Review. PubMed PMID: 22578891.

Dai C, Cazares L H, Wang L, Chu Y, Wang S L, Troyer D A, Semmes O J, Drake R R, Wang B. Using boronolectin in MALDI-MS imaging for the histological analysis of cancer tissue expressing the sialyl Lewis X antigen. Chem Commun (Camb). 2011 Oct. 7; 47(37):10338-40. doi: 10.1039/c1cc11814e. Epub 2011 Aug. 19. PubMed PMID: 21853197.

Daiger S P, Sullivan L S, Bowne S J, Birch D G, Heckenlively J R, Pierce E A, Weinstock G M. Targeted high-throughput DNA sequencing for gene discovery in retinitis pigmentosa. Adv Exp Med Biol. 2010; 664:325-31. doi: 10.1007/978-1-4419-1399-9_37. PubMed PMID: 20238032; PubMed Central PMCID: PMC2909649.

De Jesús-Cortés H, Xu P, Drawbridge J, Estill S J, Huntington P, Tran S, Britt J, Tesla R, Morlock L, Naidoo J, Melito L M, Wang G, Williams N S, Ready J M, McKnight S L, Pieper A A. Neuroprotective efficacy of aminopropyl carbazoles in a mouse model of Parkinson disease. Proc Natl Acad Sci USA. 2012 Oct. 16; 109(42):17010-5. doi: 10.1073/pnas. 1213956109. Epub 2012 Oct. 1. PubMed PMID: 23027934; PubMed Central PMCID: PMC3479520.

Demos C, Bandyopadhyay M, Rohrer B. Identification of candidate genes for human retinal degeneration loci using differentially expressed genes from mouse photoreceptor dystrophy models. Mol Vis. 2008 Sep. 5; 14:1639-49. PubMed PMID: 18776951; PubMed Central PMCID: PMC2529471.

Dong S Q, Xu H Z, Xia X B, Wang S, Zhang L X, Liu S Z. Activation of the ERK 1/2 and STAT3 signaling pathways is required for 661W cell survival following oxidant injury. Int J Ophthalmol. 2012; 5(2):138-42. doi: 10.3980/j.issn. 2222-3959.2012.02.04. Epub 2012 Apr. 18. PubMed PMID: 22762037; PubMed Central PMCID: PMC3359025.

Egger A, Samardzija M, Sothilingam V, Tanimoto N, Lange C, Salatino S, Fang L, Garcia-Garrido M, Beck S, Okoniewski M J, Neutzner A, Seeliger M W, Grimm C, Handschin C. PGC-1α determines light damage susceptibility of the murine retina. PLoS One. 2012; 7(2): e31272. doi: 10.1371/journal.pone. 0031272. Epub 2012 Feb. 13. PubMed PMID: 22348062; PubMed Central PMCID: PMC3278422.

Estrada-Cuzcano A, Roepman R, Cremers F P, den Hollander A I, Mans D A. Non-syndromic retinal ciliopathies: translating gene discovery into therapy. Hum Mol Genet. 2012 Oct. 15; 21(R1):R111-24. Epub 2012 Jul. 26. PubMed PMID: 22843501.

Falk M J, Zhang Q, Nakamaru-Ogiso E, Kannabiran C, Fonseca-Kelly Z, Chakarova C, Audo I, Mackay D S, Zeitz C, Borman A D, Staniszewska M, Shukla R, Palavalli L, Mohand-Said S, Waseem N H, Jalali S, Perin J C, Place E, Ostrovsky J, Xiao R, Bhattacharya S S, Consugar M, Webster A R, Sahel J A, Moore A T, Berson E L, Liu Q, Gai X, Pierce E A. NMNAT1 mutations cause Leber congenital amaurosis. Nat Genet. 2012 September; 44(9): 1040-5. doi: 10.1038/ng. 2361. Epub 2012 Jul. 29. PubMed PMID: 22842227; PubMed Central PMCID: PMC3454532.

Farber D B, Lolley R N: Cyclic guanosine monophosphate: elevation in degenerating photoreceptor cells of the C3H mouse retina. Science 1974, 186:449-451.

Farber D B: From mice to men: the cyclic GMP phosphodiesterase gene in vision and disease. The Proctor Lecture. Invest Ophthalmol Vis Sci 1995, 36(2):263-275.

Ferrick D A, Neilson A, Beeson C. Advances in measuring cellular bioenergetics using extracellular flux. Drug Discov Today. 2008 March; 13(5-6):268-74. doi: 10.1016/j.drudis. 2007.12.008. Epub 2008 Feb. 13. Review. PubMed PMID: 18342804.

Fox D A, Poblenz A T, He L: Calcium overload triggers rod photoreceptor apoptotic cell death in chemical-induced and inherited retinal degenerations. Ann NY Acad Sci 1999, 893:282-285.

Gilliam J C, Chang J T, Sandoval I M, Zhang Y, Li T, Pittler S J, Chiu W, Wensel T G. Three-dimensional architecture of the rod sensory cilium and its disruption in retinal neurodegeneration. Cell. 2012 Nov. 21; 151(5):1029-41. doi: 10.1016/j.cell.2012.10.038. PubMed PMID: 23178122.

Graymore C: Metabolism of the Developing Retina. 7. Lactic Dehydrogenase Isoenzyme in the Normal and Degenerating Retina. a Preliminary Communication. Exp Eye Res 1964, 89:5-8.

Hartong D T, Dange M, McGee T L, Berson E L, Dryja T P, Colman R F. Insights from retinitis pigmentosa into the roles of isocitrate dehydrogenases in the Krebs cycle. Nat Genet. 2008 October; 40(10):1230-4. doi: 10.1038/ng. 223. Epub 2008 Sep. 21. PubMed PMID: 18806796; PubMed Central PMCID: PMC2596605.

Ho C H, Piotrowski J, Dixon S J, Baryshnikova A, Costanzo M, Boone C. Combining functional genomics and chemical biology to identify targets of bioactive compounds. Curr Opin Chem Biol. 2011 February; 15(1):66-78. doi: 10.1016/j.cbpa. 2010.10.023. Epub 2010 Nov. 17. Review. PubMed PMID: 21093351.

Ibebunjo C, Chick J M, Kendall T, Eash J K, Li C, Zhang Y, Vickers C, Wu Z, Clarke B A, Shi J, Cruz J, Fournier B, Brachat S, Gutzwiller S, Ma Q, Markovits J, Broome M, Steinkrauss M, Skuba E, Galarneau J R, Gygi S P, Glass D J. Genomic and proteomic profiling reveals reduced mitochondrial function and disruption of the neuromuscular junction driving rat sarcopenia. Mol Cell Biol. 2013 January; 33(2):194-212. doi: 10.1128/MCB. 01036-12. Epub 2012 Oct. 29. PubMed PMID: 23109432.

Jaliffa C, Ameqrane I, Dansault A, Leemput J, Vieira V, Lacassagne E, Provost A, Bigot K, Masson C, Menasche M, Abitbol M. Sirt1 involvement in rd10 mouse retinal degeneration. Invest Ophthalmol Vis Sci. 2009 August; 50(8):3562-72. doi: 10.1167/iovs. 08-2817. Epub 2009 Apr. 30. PubMed PMID: 19407027.

Jarrett S G, Rohrer B, Perron N R, Beeson C, Boulton M E. Assessment of mitochondrial damage in retinal cells and tissues using quantitative polymerase chain reaction for mitochondrial DNA damage and extracellular flux assay for mitochondrial respiration activity. Methods Mol Biol. 2013; 935:227-43. doi: 10.1007/978-1-62703-080-9_16. PubMed PMID: 23150372.

Jewett J C, Bertozzi C R. Cu-free click cycloaddition reactions in chemical biology. Chem Soc Rev. 2010 April; 39(4):1272-9. Review. PubMed PMID: 20349533; PubMed Central PMCID: PMC2865253.

Kanan Y, Moiseyev G, Agarwal N, Ma J X, Al-Ubaidi M R. Light induces programmed cell death by activating multiple independent proteases in a cone photoreceptor cell line. Invest Ophthalmol Vis Sci. 2007 January; 48(1):40-51. PubMed PMID: 17197514.

Kandpal R P, Rajasimha H K, Brooks M J, Nellissery J, Wan J, Qian J, Kern T S, Swaroop A. Transcriptome analysis using next generation sequencing reveals molecular signatures of diabetic retinopathy and efficacy of candidate drugs. Mol Vis. 2012; 18:1123-46. Epub 2012 May 2. PubMed PMID: 22605924; PubMed Central PMCID: PMC3351417.

Karbowski M, Neutzner A. Neurodegeneration as a consequence of failed mitochondrial maintenance. Acta Neuropathol. 2012 February; 123(2):157-71. doi: 10.1007/s00401-011-0921-0. Epub 2011 Dec. 7. Review. PubMed PMID: 22143516.

Kroeger H, Messah C, Ahern K, Gee J, Joseph V, Matthes M T, Yasumura D, Gorbatyuk M S, Chiang W C, Lavail M M, Lin J H. Induction of Endoplasmic Reticulum Stress Genes, BiP and Chop, in Genetic and Environmental Models of Retinal Degeneration. Invest Ophthalmol Vis Sci. 2012 Nov. 9; 53(12):7590-9. doi: 10.1167/iovs. 12-10221. PubMed PMID: 23074209; PubMed Central PMCID: PMC3495601.

Krysko D V, Agostinis P, Krysko O, Garg A D, Bachert C, Lambrecht B N, Vandenabeele P. Emerging role of damage-associated molecular patterns derived from mitochondria in inflammation. Trends Immunol. 2011 April; 32(4):157-64. doi: 10.1016/j.it. 2011.01.005. Epub 2011 Feb. 19. Review. PubMed PMID: 21334975.

Kunchithapautham K, Rohrer B: Apoptosis and Autophagy in Photoreceptors Exposed to Oxidative Stress. Autophagy 2007, 3(5).

Lenz E M, Wilson I D: Analytical strategies in metabonomics. *J Proteome Res* 2007, 6(2):443-458.

Lin J H, Lavail M M. Misfolded proteins and retinal dystrophies. Adv Exp Med Biol. 2010; 664:115-21. doi: 10.1007/978-1-4419-1399-9_14. Review. PubMed PMID: 20238009; PubMed Central PMCID: PMC2955894.

Liu Q, Tan G, Levenkova N, Li T, Pugh E N Jr, Rux J J, Speicher D W, Pierce E A. The proteome of the mouse photoreceptor sensory cilium complex. Mol Cell Proteomics. 2007 August; 6(8):1299-317. Epub 2007 May 9. PubMed PMID: 17494944; PubMed Central PMCID: PMC2128741.

Liu Q, Zhang Q, Pierce E A. Photoreceptor sensory cilia and inherited retinal degeneration. Adv Exp Med Biol. 2010; 664:223-32. doi: 10.1007/978-1-4419-1399-9_26. Review. PubMed PMID: 20238021; PubMed Central PMCID: PMC2888132.

Lohr H R, Kuntchithapautham K, Sharma A K, Rohrer B: Multiple, parallel cellular suicide mechanisms participate in photoreceptor cell death. Exp Eye Res 2006, 83(2): 380-389.

Lohr H R, Kuntchithapautham K, Sharma A K, Rohrer B. Multiple, parallel cellular suicide mechanisms participate in photoreceptor cell death. Exp Eye Res. 2006 August; 83(2):380-9. Epub 2006 Apr. 19. Erratum in: Exp Eye Res. 2006 December; 83(6):1522. PubMed PMID: 16626700.

MacMillan K S, Naidoo J, Liang J, Melito L, Williams N S, Morlock L, Huntington P J, Estill S J, Longgood J, Becker G L, McKnight S L, Pieper A A, De Brabander J K, Ready J M. Development of proneurogenic, neuroprotective small molecules. J Am Chem Soc. 2011 Feb. 9; 133(5): 1428-37. doi: 10.1021/ja108211m. Epub 2011 Jan. 6. PubMed PMID: 21210688; PubMed Central PMCID: PMC3033481.

Mamidyala S K, Finn M G. In situ click chemistry: probing the binding landscapes of biological molecules. Chem Soc Rev. 2010 April; 39(4):1252-61. doi: 10.1039/b901969n. Epub 2010 Mar. 1. Review. PubMed PMID: 20309485.

Mandal M N, Patlolla J M, Zheng L, Agbaga M P, Tran J T, Wicker L, Kasus-Jacobi A, Elliott M H, Rao C V, Anderson R E. Curcumin protects retinal cells from light- and oxidant stress-induced cell death. Free Radic Biol Med. 2009 Mar. 1; 46(5):672-9. doi: 10.1016/j.freeradbiomed. 2008.12.006. Epub 2008 Dec. 24. PubMed PMID: 19121385; PubMed Central PMCID: PMC2810836.

Marina N, Sajic M, Bull N D, Hyatt A J, Berry D, Smith K J, Martin K R. Lamotrigine monotherapy does not provide protection against the loss of optic nerve axons in a rat model of ocular hypertension. Exp Eye Res. 2012 November; 104:1-6. doi: 10.1016/j.exer. 2012.09.002. Epub 2012 Sep. 13. PubMed PMID: 22982756.

Mattson M P, Kroemer G: Mitochondria in cell death: novel targets for neuroprotection and cardioprotection. Trends Mol Med 2003, 9(5):196-205.

McKnight S L. Back to the future: molecular biology meets metabolism. Cold Spring Harb Symp Quant Biol. 2011; 76:403-11. doi: 10.1101/sqb. 2012.76.013722. Epub 2012 Apr. 17. Review. PubMed PMID: 22510749.

Mueller E E, Schaier E, Brunner S M, Eder W, Mayr J A, Egger S F, Nischler C, Oberkofler H, Reitsamer H A, Patsch W, Sperl W, Kofler B. Mitochondrial haplogroups and control region polymorphisms in age-related macular degeneration: a case-control study. PLoS One. 2012; 7(2):e30874. doi: 10.1371/journal.pone. 0030874. Epub 2012 Feb. 13. PubMed PMID: 22348027; PubMed Central PMCID: PMC3278404.

Mulkidjanian A Y, Galperin M Y, Makarova K S, Wolf Y I, Koonin E V. Evolutionary primacy of sodium bioenergetics. Biol Direct. 2008 Apr. 1; 3:13. doi: 10.1186/1745-6150-3-13. PubMed PMID: 18380897; PubMed Central PMCID: PMC2359735.

Nicholas P C, Kim D, Crews F T, Macdonald J M: (1)H NMR-Based Metabolomic Analysis of Liver, Serum, and Brain Following Ethanol Administration in Rats. *Chem Res Toxicol* 2007.

Nixon E, Simpkins J W. Neuroprotective effects of nonfeminizing estrogens in retinal photoreceptor neurons. Invest Ophthalmol Vis Sci. 2012 Jul. 12; 53(8):4739-47. doi: 10.1167/iovs. 12-9517. Print 2012 July PubMed PMID: 22700711.

O'Toole J F, Liu Y, Davis E E, Westlake C J, Attanasio M, Otto E A, Seelow D, Nurnberg G, Becker C, Nuutinen M, Käppä M, Ignatius J, Uusimaa J, Pakanen S, Jaakkola E, van den Heuvel L P, Fehrenbach H, Wiggins R, Goyal M, Zhou W, Wolf M T, Wise E, Helou J, Allen S J, Murga-Zamalloa C A, Ashraf S, Chaki M, Heeringa S, Chernin G, Hoskins B E, Chaib H, Gleeson J, Kusakabe T, Suzuki T, Isaac R E, Quarmby L M, Tennant B, Fujioka H, Tuominen H, Hassinen I, Lohi H, van Houten J L, Rotig A, Sayer J A, Rolinski B, Freisinger P, Madhavan S M, Herzer M, Madignier F, Prokisch H, Nurnberg P, Jackson P K, Khanna H, Katsanis N, Hildebrandt F. Individuals with mutations in XPNPEP3, which encodes a mitochondrial protein, develop a nephronophthisis-like nephropathy. J Clin Invest. 2010 March; 120(3):791-802. doi: 10.1172/JCI40076. Epub 2010 Feb. 22. Erratum in: J Clin Invest. 2010 April; 120(4):1362. Jackson, Peter [corrected to Jackson, Peter K]. PubMed PMID: 20179356; PubMed Central PMCID: PMC2827951.

Osborne N N, Del Olmo-Aguado S. Maintenance of retinal ganglion cell mitochondrial functions as a neuroprotective strategy in glaucoma. Curr Opin Pharmacol. 2012

Sep. 19. doi:pii: S1471-4892(12)00159-2.10.1016/j.coph. 2012.09.002. [Epub ahead of print] PubMed PMID: 22999653.

Pappas D J, Gabatto P A, Oksenberg D, Khankhanian P, Baranzini S E, Gan L, Oksenberg J R. Transcriptional expression patterns triggered by chemically distinct neuroprotective molecules. Neuroscience. 2012 Dec. 13; 226: 10-20. doi: 10.1016/j.neuroscience. 2012.09.007. Epub 2012 Sep. 15. PubMed PMID: 22986168; PubMed Central PMCID: PMC3489981.

Pereira D A, Williams J A. Origin and evolution of high throughput screening. Br J Pharmacol. 2007 September; 152(1):53-61. Epub 2007 Jul. 2. Review. PubMed PMID: 17603542; PubMed Central PMCID: PMC1978279.

Perron N R, Beeson C, Rohrer B. Early alterations in mitochondrial reserve capacity; a means to predict subsequent photoreceptor cell death. J Bioenerg Biomembr. 2012 Oct. 23. [Epub ahead of print] PubMed PMID: 23090843.

Phillips M J, Walker T A, Choi H Y, Faulkner A E, Kim M K, Sidney S S, Boyd A P, Nickerson J M, Boatright J H, Pardue M T. Tauroursodeoxycholic acid preservation of photoreceptor structure and function in the rd10 mouse through postnatal day 30. Invest Ophthalmol Vis Sci. 2008 May; 49(5):2148-55. PubMed PMID: 18436848.

Pieper A A, Xie S, Capota E, Estill S J, Zhong J, Long J M, Becker G L, Huntington P, Goldman S E, Shen C H, Capota M, Britt J K, Kotti T, Ure K, Brat D J, Williams N S, MacMillan K S, Naidoo J, Melito L, Hsieh J, De Brabander J, Ready J M, McKnight S L. Discovery of a proneurogenic, neuroprotective chemical. Cell. 2010 Jul. 9; 142(1):39-51. doi: 10.1016/j.cell.2010.06.018. PubMed PMID: 20603013; PubMed Central PMCID: PMC2930815.

Pierce E A, Quinn T, Meehan T, McGee T L, Berson E L, Dryja T P: Mutations in a gene encoding a new oxygen-regulated photoreceptor protein cause dominant retinitis pigmentosa. Nat Genet 1999, 22(3):248-254.

Pierce E A: Pathways to photoreceptor cell death in inherited retinal degenerations. Bioessays 2001, 23(7):605-618.

Qin L X, Beyer R P, Hudson F N, Linford N J, Morris D E, Kerr K F. Evaluation of methods for oligonucleotide array data via quantitative real-time PCR. BMC Bioinformatics. 2006 Jan. 17; 7:23. PubMed PMID: 16417622; PubMed Central PMCID: PMC1360686.

Rezaie T, McKercher S R, Kosaka K, Seki M, Wheeler L, Viswanath V, Chun T, Joshi R, Valencia M, Sasaki S, Tozawa T, Satoh T, Lipton S A. Protective effect of carnosic Acid, a pro-electrophilic compound, in models of oxidative stress and light-induced retinal degeneration. Invest Ophthalmol Vis Sci. 2012 Nov. 27; 53(12):7847-54. doi: 10.1167/iovs. 12-10793. PubMed PMID: 23081978; PubMed Central PMCID: PMC3508754.

Richards A J, Muller B, Shotwell M, Cowart L A, Rohrer B, Lu X. Assessing the functional coherence of gene sets with metrics based on the Gene Ontology graph. Bioinformatics. 2010 Jun. 15; 26(12):i79-87. doi: 10.1093/bioinformatics/btq203. PubMed PMID: 20529941; PubMed Central PMCID: PMC2881388.

Richards T A, Cavalier-Smith T. Myosin domain evolution and the primary divergence of eukaryotes. Nature. 2005 Aug. 25; 436(7054):1113-8. PubMed PMID: 16121172.

Rohrer B, Matthes M T, LaVail M M, Reichardt L F: Lack of p75 receptor does not protect photoreceptors from light-induced cell death. *Exp Eye Res* 2003, 76(1):125-129

Rohrer B, Pinto F R, Hulse K E, Lohr H R, Zhang L, Almeida J S. Multidestructive pathways triggered in photoreceptor cell death of the rd mouse as determined through gene expression profiling. J Biol Chem. 2004 Oct. 1; 279(40):41903-10. Epub 2004 Jun. 24. PubMed PMID: 15218024.

Ronquillo C C, Bernstein P S, Baehr W. Senior-Løken syndrome: A syndromic form of retinal dystrophy associated with nephronophthisis. Vision Res. 2012 Dec. 15; 75:88-97. doi: 10.1016/j.visres. 2012.07.003. Epub 2012 Jul. 20. PubMed PMID: 22819833; PubMed Central PMCID: PMC3504181.

Sancho-Pelluz J, Alavi M V, Sahaboglu A, Kustermann S, Farinelli P, Azadi S, van Veen T, Romero F J, Paquet-Durand F, Ekstrom P. Excessive HDAC activation is critical for neurodegeneration in the rd1 mouse. Cell Death Dis. 2010; 1:e24. doi: 10.1038/cddis. 2010.4. PubMed PMID: 21364632; PubMed Central PMCID: PMC3032332.

Sancho-Pelluz J, Arango-Gonzalez B, Kustermann S, Romero F J, van Veen T, Zrenner E, Ekström P, Paquet-Durand F. Photoreceptor cell death mechanisms in inherited retinal degeneration. Mol Neurobiol. 2008 December; 38(3):253-69. doi: 10.1007/s12035-008-8045-9. Epub 2008 Nov. 4. Review. PubMed PMID: 18982459.

SanGiovanni J P, Arking D E, Iyengar S K, Elashoff M, Clemons T E, Reed G F, Henning A K, Sivakumaran T A, Xu X, DeWan A, Agrón E, Rochtchina E, Sue C M, Wang J J, Mitchell P, Hoh J, Francis P J, Klein M L, Chew E Y, Chakravarti A. Mitochondrial DNA variants of respiratory complex I that uniquely characterize haplogroup T2 are associated with increased risk of age-related macular degeneration. PLoS One. 2009; 4(5):e5508. doi: 10.1371/journal.pone. 0005508. Epub 2009 May 12. PubMed PMID: 19434233; PubMed Central PMCID: PMC2677106.

Schrier S A, Falk M J. Mitochondrial disorders and the eye. Curr Opin Ophthalmol. 2011 September; 22(5):325-31. doi: 10.1097/ICU. 0b013e328349419d. Review. PubMed PMID: 21730846.

Sharma A K, Rohrer B: Calcium-induced calpain mediates apoptosis via caspase-3 in a mouse photoreceptor cell line. J Biol Chem 2004, 279(34):35564-35572.

Sharma A K, Rohrer B. Calcium-induced calpain mediates apoptosis via caspase-3 in a mouse photoreceptor cell line. J Biol Chem. 2004 Aug. 20; 279(34):35564-72. Epub 2004 Jun. 18. PubMed PMID: 15208318.

Sharma A K, Rohrer B. Sustained elevation of intracellular cGMP causes oxidative stress triggering calpain-mediated apoptosis in photoreceptor degeneration. Curr Eye Res. 2007 March; 32(3):259-69. PubMed PMID: 17453946.

Shimazaki H, Hironaka K, Fujisawa T, Tsuruma K, Tozuka Y, Shimazawa M, Takeuchi H, Hara H. Edaravone-loaded liposome eye drops protect against light-induced retinal damage in mice. Invest Ophthalmol Vis Sci. 2011 Sep. 21; 52(10):7289-97. doi: 10.1167/iovs. 11-7983. Print 2011 September PubMed PMID: 21849425.

Smith J J, Kenney R D, Gagne D J, Frushour B P, Ladd W, Galonek H L, Israelian K, Song J, Razvadauskaite G, Lynch A V, Carney D P, Johnson R J, Lavu S, Iffland A, Elliott P J, Lambert P D, Elliston K O, Jirousek M R, Milne J C, Boss O. Small molecule activators of SIRT1 replicate signaling pathways triggered by calorie restriction in vivo. BMC Syst Biol. 2009 Mar. 10; 3:31. doi: 10.1186/1752-0509-3-31. PubMed PMID: 19284563; PubMed Central PMCID: PMC2660283.

Spinazzi M, Cazzola S, Bortolozzi M, Baracca A, Loro E, Casarin A, Solaini G, Sgarbi G, Casalena G, Cenacchi G, Malena A, Frezza C, Carrara F, Angelini C, Scorrano L, Salviati L, Vergani L. A novel deletion in the GTPase domain of OPA1 causes defects in mitochondrial morphology and distribution, but not in function. Hum Mol Genet. 2008 Nov. 1; 17(21):3291-302. doi: 10.1093/hmg/ddn225. Epub 2008 Aug. 4. PubMed PMID: 18678599.

Stone J, Maslim J, Valter-Kocsi K, Mervin K, Bowers F, Chu Y, Barnett N, Provis J, Lewis G, Fisher S K et al: Mechanisms of photoreceptor death and survival in mammalian retina. *Prog Retin Eye Res* 1999, 18(6):689-735.

Sumantran V N. Cellular chemosensitivity assays: an overview. Methods Mol Biol. 2011; 731:219-36. doi: 10.1007/978-1-61779-080-5_19. Review. PubMed PMID: 21516411.

Tan E, Ding X Q, Saadi A, Agarwal N, Naash M I, Al-Ubaidi M R: Expression of cone-photoreceptor-specific antigens in a cell line derived from retinal tumors in transgenic mice. Invest Ophthalmol Vis Sci 2004, 45(3):764-768.

Tan E, Ding X Q, Saadi A, Agarwal N, Naash M I, Al-Ubaidi M R. Expression of cone-photoreceptor-specific antigens in a cell line derived from retinal tumors in transgenic mice. Invest Ophthalmol Vis Sci. 2004 March; 45(3):764-8. PubMed PMID: 14985288; PubMed Central PMCID: PMC2937568.

Tesla R, Wolf H P, Xu P, Drawbridge J, Estill S J, Huntington P, McDaniel L, Knobbe W, Burket A, Tran S, Starwalt R, Morlock L, Naidoo J, Williams N S, Ready J M, McKnight S L, Pieper A A. Neuroprotective efficacy of aminopropyl carbazoles in a mouse model of amyotrophic lateral sclerosis. Proc Natl Acad Sci USA. 2012 Oct. 16; 109(42):17016-21. doi: 10.1073/pnas. 1213960109. Epub 2012 Oct. 1. PubMed PMID: 23027932; PubMed Central PMCID: PMC3479516.

Travis G H: Mechanisms of cell death in the inherited retinal degenerations. Am J Hum Genet 1998, 62(3):503-508.

TrifunoviéD, Sahaboglu A, Kaur J, Mencl S, Zrenner E, Ueffing M, Arango-Gonzalez B, Paquet-Durand F. Neuroprotective strategies for the treatment of inherited photoreceptor degeneration. Curr Mol Med. 2012 June; 12(5): 598-612. Review. PubMed PMID: 22515977.

Tu B P, Mohler R E, Liu J C, Dombek K M, Young E T, Synovec R E, McKnight S L. Cyclic changes in metabolic state during the life of a yeast cell. Proc Natl Acad Sci USA. 2007 Oct. 23; 104(43):16886-91. Epub 2007 Oct. 16. PubMed PMID: 17940006; PubMed Central PMCID: PMC2040445.

Van Bergen N J, Crowston J G, Kearns L S, Staffieri S E, Hewitt A W, Cohn A C, Mackey D A, Trounce I A. Mitochondrial oxidative phosphorylation compensation may preserve vision in patients with OPA1-linked autosomal dominant optic atrophy. PLoS One. 2011; 6(6): e21347. doi: 10.1371/journal.pone. 0021347. Epub 2011 Jun. 22. PubMed PMID: 21731710; PubMed Central PMCID: PMC3120866.

Vingolo E M, De Mattia G, Giusti C, Forte R, Laurenti O, Pannarale M R: Treatment of nonproliferative diabetic retinopathy with Defibrotide in noninsulin-dependent diabetes mellitus: a pilot study. Acta Ophthalmol Scand 1999, 77(3):315-320.

Wenzel A, Grimm C, Samardzija M, Reme C E: Molecular mechanisms of light-induced photoreceptor apoptosis and neuroprotection for retinal degeneration. Prog Retin Eye Res 2005, 24(2):275-306.

Whitfield J F, Chakravarthy B R. The neuronal primary cilium: driver of neurogenesis and memory formation in the hippocampal dentate gyms? Cell Signal. 2009 September; 21(9):1351-5. doi: 10.1016/j.cellsig. 2009.02.013. Epub 2009 Feb. 26. Review. PubMed PMID: 19249355.

Winkler B S, Pourcho R G, Starnes C, Slocum J, Slocum N. Metabolic mapping in mammalian retina: a biochemical and 3H-2-deoxyglucose autoradiographic study. Exp Eye Res. 2003 September; 77(3):327-37. PubMed PMID: 12907165.

Winkler B S. Letter to the editor: Comments on retinal metabolic state in P23H and normal retinas. Am J Physiol Cell Physiol. 2010 July; 299(1):C185; author reply C186-7. doi: 10.1152/ajpcell.00109.2010. PubMed PMID: 20554913.

Yamada Y, Hidefumi K, Shion H, Oshikata M, Haramaki Y. Distribution of chloroquine in ocular tissue of pigmented rat using matrix-assisted laser desorption/ionization imaging quadrupole time-of-flight tandem mass spectrometry. Rapid Commun Mass Spectrom. 2011 Jun. 15; 25(11): 1600-8. doi: 10.1002/rcm. 5021. PubMed PMID: 21594935.

Yang L, Nyalwidhe J O, Guo S, Drake R R, Semmes O J. Targeted identification of metastasis-associated cell-surface sialoglycoproteins in prostate cancer. Mol Cell Proteomics. 2011 June; 10(6):M110.007294. doi: 10.1074/mcp.M110.007294. Epub 2011 Mar. 29. PubMed PMID: 21447706; PubMed Central PMCID: PMC3108840.

Ying W. NAD+ and NADH in cellular functions and cell death. Front Biosci. 2006 Sep. 1; 11:3129-48. Review. PubMed PMID: 16720381.

Farber, D. B., *From mice to men: the cyclic GMP phosphodiesterase gene in vision and disease. The Proctor Lecture.* Invest. Ophthalmol. Vis. Sci., 1995. 36(2): p. 263-275.

Farber, D. B. and R. N. Lolley, *Cyclic guanosine monophosphate: elevation in degenerating photoreceptor cells of the C3H mouse retina.* Science, 1974. 186: p. 449-451.

Fox, D. A., A. T. Poblenz, and L. He, *Calcium overload triggers rod photoreceptor apoptotic cell death in chemical-induced and inherited retinal degenerations.* Ann. N.Y. Acad. Sci., 1999. 893: p. 282-285.

Ogilvie, J. M., et al., *A reliable method for organ culture of neonatal mouse retina with long-term survival.* J. Neurosci. Methods, 1999. 87(1): p. 57-65.

It is to be understood that the invention is not limited to the particular embodiments of the invention described above, as variations of the particular embodiments may be made and still fall within the scope of the appended claims.

What is claimed is:

1. A compound, or a pharmaceutically acceptable salt thereof, wherein said compound is:
   3-hydroxy-5-methyl-1-(2,2,2-trifluoroethyl)-3-(3,4,5-trimethoxybenzyl)indolin-2-one;
   2-((3-hydroxy-5-methyl-1-(4-methylpentyl)-2-oxoindolin-3-yl)methyl)-5-methoxyphenyl isonicotinate;
   2-((3-hydroxy-5-methyl-1-(4-methylpentyl)-2-oxoindolin-3-yl)methyl)-5-methoxyphenyl acetate;
   2-((3-hydroxy-5-methyl-1-(4-methylpentyl)-2-oxoindolin-3-yl)methyl)-5-methoxyphenyl 2-methoxyacetate;
   5-chloro-1-ethyl-3-(2-hydroxy-3-methoxybenzyl)-2-oxoindolin-3-yl isonicotinate;
   5-chloro-1-ethyl-3-(2-hydroxy-3-methoxybenzyl)-2-oxoindolin-3-yl picolinate;
   5-chloro-1-ethyl-3-(2-hydroxy-3-methoxybenzyl)-2-oxoindolin-3-yl diethyl phosphate;
   2-((5-chloro-1-ethyl-3-hydroxy-2-oxoindolin-3-yl)methyl)-6-methoxyphenyl 2-methoxyacetate;

2-((5-chloro-1-ethyl-3-hydroxy-2-oxoindolin-3-yl)methyl)-6-methoxyphenyl butyrate;
5-chloro-1-ethyl-3-(2-hydroxy-3-methoxybenzyl)-2-oxoindolin-3-yl dimethylcarbamate;
(1,3-dioxolan-4-yl)methyl (5-chloro-1-ethyl-3-(2-hydroxy-3-methoxybenzyl)-2-oxoindolin-3-yl) carbonate;
5-chloro-1-ethyl-3-(2-(((2-(2-hydroxyethoxy)ethyl)carbamoyl)oxy)-3-methoxybenzyl)-2-oxoindolin-3-yl benzoate;
2-((5-chloro-1-ethyl-2-oxoindolin-3-yl)methyl)-6-methoxyphenyl dimethylcarbamate;
3-hydroxy-1,5-dimethyl-3-((1-methyl-1H-indazol-4-yl)methyl)indolin-2-one;
1-butyl-3-((1-methyl-1H-indazol-4-yl)methyl)-2-oxoindolin-3-yl benzoate;
3-(benzo[d][1,3]dioxol-4-ylmethyl)-5-chloro-2-oxo-1-propylindolin-3-yl benzoate;
3-(benzo[d][1,3]dioxol-4-ylmethyl)-1-ethyl-3-hydroxy-5-methylindolin-2-one;
3-(benzo[d][1,3]dioxol-4-ylmethyl)-1-butyl-3-hydroxyindolin-2-one;
3-(benzo[d][1,3]dioxol-4-ylmethyl)-3-hydroxy-1-isobutylindolin-2-one;
3-(benzo[d][1,3]dioxol-4-ylmethyl)-1-isopentyl-2-oxoindolin-3-yl benzoate;
3-(benzo[d][1,3]dioxol-4-ylmethyl)-1-isobutyl-5-methyl-2-oxoindolin-3-yl benzoate;
3-(benzo[d][1,3]dioxol-4-ylmethyl)-1-isopentyl-5-methyl-2-oxoindolin-3-yl benzoate;
3-((1H-benzo[d]imidazol-4-yl)methyl)-5-chloro-1-ethyl-3-hydroxyindolin-2-one,
1-ethyl-3-(2-hydroxy-3,4-dimethoxybenzyl)-5-methyl-2-oxoindolin-3-yl dimethylcarbamate;
3-((1-benzoyl-1H-indol-3-yl)methyl)-2-oxo-1-propylindolin-3-yl dimethylcarbamate;
3-((1H-benzo[d]imidazol-4-yl)methyl)-5-chloro-1-methyl-2-oxoindolin-3-yl dimethylcarbamate;
5-chloro-1-ethyl-3-(pyrimidin-4-ylmethyl)indolin-2-one;
5-methyl-1-ethyl-3-(pyrimidin-4-ylmethylene)indolin-2-one;
5-chloro-1-ethyl-3-hydroxy-3-(pyrazin-2-ylmethyl)indolin-2-one;
1-ethyl-5-methyl-3-(pyrazin-2-ylmethylene)indolin-2-one;
1-propyl-3-(pyridazin-3-ylmethyl)indolin-2-one;
N-(5-chloro-2-oxo-1-propyl-3-(pyridazin-3-ylmethyl)indolin-3-yl)nicotinamide;
3-((1H-benzo[d]imidazol-2-yl)methylene)-5-chloro-1-ethylindolin-2-one;
5-chloro-3-hydroxy-1-propyl-3-(pyrazin-2-ylmethyl)indolin-2-one;
5-chloro-3-hydroxy-1-methyl-3-(pyridin-4-ylmethyl)indolin-2-one;
5-chloro-3-hydroxy-1-propyl-3-(pyridazin-4-ylmethyl)indolin-2-one;
3-hydroxy-1-methyl-3-(pyridin-4-ylmethyl)indolin-2-one;
(E)-3-((11H-benzo[d]imidazol-2-yl)methylene)-5-chloro-1-methylindolin-2-one;
N-(3-((1H-benzo[d]imidazol-2-yl)methyl)-1-methyl-2-oxoindolin-3-yl)nicotinamide;
1-ethyl-3-hydroxy-3-(pyridazin-3-ylmethyl)indolin-2-one;
1-ethyl-5-methyl-3,3-bis(pyridazin-4-ylmethyl)indolin-2-one;
1-propyl-3,3-bis(pyridazin-4-ylmethyl)indolin-2-one;
1-ethyl-3-hydroxy-5-methyl-3-(pyridazin-3-ylmethyl)indolin-2-one;
N-(3-((1H-benzo[d]imidazol-2-yl)methyl)-5-chloro-1-ethyl-2-oxoindolin-3-yl)isonicotinamide;
3-(benzo[d]oxazol-2-ylmethylene)-5-chloro-1-methylindolin-2-one;
N-(3-((1H-benzo[d]imidazol-2-yl)methyl)-5-chloro-2-oxo-1-propylindolin-3-yl)benzamide;
1-methyl-3-(oxazolo[4,5-b]pyridin-2-ylmethylene)indolin-2-one;
5-chloro-2-oxo-1-(2-(piperidin-1-yl)ethyl)-3-(pyridin-2-ylmethyl)indolin-3-yl dimethylcarbamate;
N-(3-((3-methoxypyridin-2-yl)methyl)-2-oxo-1-propylindolin-3-yl)benzamide;
N-(5-chloro-1-ethyl-2-oxo-3-(pyridin-2-ylmethyl)indolin-3-yl)-4-methylbenzenesulfonamide;
3-(1-ethyl-5-methyl-3-((1-methyl-1H-indazol-4-yl)methyl)-2-oxoindolin-3-yl)-1,1-dimethylurea;
1,1-dimethyl-3-(3-((1-methyl-1H-indazol-4-yl)methyl)-2-oxo-1-propylindolin-3-yl)urea;
3-(3-(benzo[d][1,3]dioxol-4-ylmethyl)-2-oxo-1-propylindolin-3-yl)-1,1-dimethylurea;
3-(3-(benzo[d][1,3]dioxol-4-ylmethyl)-5-chloro-1-methyl-2-oxoindolin-3-yl)-1,1-dimethylurea;
3-(3-(benzo[d][1,3]dioxol-4-ylmethyl)-5-chloro-2-oxo-1-propylindolin-3-yl)-1,1-dimethylurea;
3-(1,5-dimethyl-2-oxo-3-(3,4,5-trimethoxybenzyl)indolin-3-yl)-1,1-dimethylurea;
3-(1-ethyl-2-oxo-3-(3,4,5-tri methoxybenzyl)indolin-3-yl)-1,1-dimethylurea;
3-(3-((1-benzoyl-1H-indol-3-yl)methyl)-1-ethyl-2-oxoindolin-3-yl)-1,1-dimethylurea;
3-(3-((1-benzoyl-1H-indol-3-yl)methyl)-1-methyl-2-oxoindolin-3-yl)-1,1-dimethylurea;
3-(3-((1-benzoyl-1H-indol-3-yl)methyl)-2-oxo-1-propylindolin-3-yl)-1,1-dimethylurea;
3-(3-((1-benzoyl-1H-indol-3-yl)methyl)-5-methyl-2-oxo-1-propylindolin-3-yl)-1,1-dimethylurea;
or
2-((5-chloro-1-ethyl-3-hydroxy-2-oxoindolin-3-yl)methyl)-6-methoxyphenyl dimethylsulfamate.

2. A pharmaceutical composition, comprising a therapeutically effective amount of a compound according to claim 1, or a pharmaceutically acceptable salt thereof, and a pharmaceutically acceptable carrier.

* * * * *